US007378244B2

(12) United States Patent
Morin et al.

(10) Patent No.: US 7,378,244 B2
(45) Date of Patent: May 27, 2008

(54) TELOMERASE PROMOTERS SEQUENCES FOR SCREENING TELOMERASE MODULATORS

(75) Inventors: Gregg B. Morin, Vancouver (CA); Serge Lichtsteiner, Encinitas, CA (US); Alain Vasserot, Carlsbad, CA (US); Robert Adams, Redwood City, CA (US); William H. Andrews, Reno, NV (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 11/411,604

(22) Filed: Apr. 25, 2006

(65) Prior Publication Data
US 2006/0281106 A1    Dec. 14, 2006

Related U.S. Application Data

(60) Division of application No. 09/615,039, filed on Jul. 11, 2000, now abandoned, which is a continuation of application No. PCT/US00/03104, filed on Feb. 4, 2000, which is a continuation-in-part of application No. 09/244,438, filed on Feb. 4, 1999, now Pat. No. 6,777,203, application No. 11/411,604, which is a continuation-in-part of application No. 10/325,810, filed on Dec. 20, 2002, now Pat. No. 7,199,234, which is a continuation of application No. 09/402,181, filed as application No. PCT/US97/17885 on Oct. 1, 1997, now Pat. No. 6,610,839.

(51) Int. Cl.
C12Q 1/68 (2006.01)
(52) U.S. Cl. .......................................... 435/6; 536/24.1
(58) Field of Classification Search .............. 435/6; 536/24.1
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis |
| 4,816,567 A | 3/1989 | Cabilly et al. |
| 4,965,188 A | 10/1990 | Mullis et al. |
| 5,416,017 A | 5/1995 | Burton et al. ............ 435/240.2 |
| 5,489,508 A | 2/1996 | West et al. |
| 5,583,016 A | 12/1996 | Villeponteau et al. |
| 5,631,236 A | 5/1997 | Woo et al. .................. 514/44 |
| 5,698,443 A | 12/1997 | Henderson et al. ....... 435/320.1 |
| 5,728,379 A | 3/1998 | Martuza et al. .......... 424/93.2 |
| 5,747,317 A | 5/1998 | Cao |
| 5,770,422 A | 6/1998 | Collins |
| 5,907,083 A | 5/1999 | Robert et al. |
| 5,919,656 A | 7/1999 | Harrington et al. |
| 5,998,205 A | 12/1999 | Hallenbeck et al. ........ 435/325 |
| 6,054,575 A | 4/2000 | Villeponteau et al. |
| 6,083,717 A | 7/2000 | Madzak et al. |
| 6,093,809 A | 7/2000 | Cech et al. |
| 6,166,178 A | 12/2000 | Cech et al. .................. 530/324 |
| 6,175,060 B1 | 1/2001 | Lefebvre et al. |
| 6,228,643 B1 | 5/2001 | Greenland et al. |
| 6,261,556 B1 | 7/2001 | Weinrich et al. |
| 6,261,836 B1 | 7/2001 | Cech et al. .................. 435/325 |
| 6,271,437 B1 | 8/2001 | Jessen et al. |
| 6,274,790 B1 | 8/2001 | Kunst et al. |
| 6,281,409 B1 | 8/2001 | Woodhead et al. |
| 6,300,095 B1 | 10/2001 | Barredo Fuente et al. |
| 6,306,656 B1 | 10/2001 | Liu et al. |
| 6,331,527 B1 | 12/2001 | Parmacek et al. |
| 6,610,839 B1 * | 8/2003 | Morin et al. ................ 536/24.1 |
| 6,627,190 B2 | 9/2003 | Wold et al. ................. 424/93.2 |
| 6,638,762 B1 | 10/2003 | Chang et al. ............... 435/325 |
| 6,686,159 B2 | 2/2004 | Andrews et al. |
| 6,777,203 B1 * | 8/2004 | Morin et al. ................ 435/69.1 |
| 6,916,642 B1 | 7/2005 | Kilian et al. |
| 7,199,234 B2 | 4/2007 | Morin et al. |

(Continued)

FOREIGN PATENT DOCUMENTS

CA    2362367 B1    8/2000

(Continued)

OTHER PUBLICATIONS

Alemany, R., et al., Complementary adenoviral vectors for oncolysis, Cancer Gene Therapy 6:21 (1999).

(Continued)

Primary Examiner—Michael C. Wilson
(74) Attorney, Agent, or Firm—Leslie A. Mooi; David J. Earp

(57) ABSTRACT

Telomerase reverse transcriptase is part of the telomerase complex responsible for maintaining telomere length and increasing the replicative capacity of progenitor cells. Telomerase activity is turned off in mature differentiated cells, but is turned back on again in hyperplastic diseases, including many cancers. This disclosure provides regulatory elements that promote transcription in cells that express telomerase reverse transcriptase (TERT). The disclosure also provides systems using TERT promoter sequences for identifying compounds that can be used to modulate telomerase expression.

4 Claims, 7 Drawing Sheets

U.S. PATENT DOCUMENTS

| | | |
|---|---|---|
| 2003/0050264 A1 | 3/2003 | Andrews et al. |
| 2003/0096732 A1 | 5/2003 | Andrews et al. |
| 2003/0099616 A1 | 5/2003 | Karpf et al. ............... 424/93.2 |
| 2003/0104420 A1 | 6/2003 | Andrews |
| 2003/0113760 A1 | 6/2003 | Andrews et al. |
| 2003/0171326 A1 | 9/2003 | Andrews et al. |
| 2003/0211965 A1 | 11/2003 | Andrews et al. |
| 2004/0072787 A1 | 4/2004 | Morin et al. |
| 2005/0214923 A1 | 9/2005 | DeChao et al. .......... 435/235.1 |
| 2007/0190561 A1 | 8/2007 | Morin et al. |

FOREIGN PATENT DOCUMENTS

| | | |
|---|---|---|
| EP | 1147181 B1 | 12/2004 |
| GB | 2 317 891 A | 4/1998 |
| GB | 2 321 642 B | 2/2000 |
| JP | 09-154575 A2 | 6/1997 |
| WO | WO 84/03564 A1 | 9/1984 |
| WO | WO 95/13382 A1 | 5/1995 |
| WO | WO 96/01835 A1 | 1/1996 |
| WO | WO 96/12811 A2 | 5/1996 |
| WO | WO 96/19580 A2 | 6/1996 |
| WO | WO 96/40868 A1 | 12/1996 |
| WO | WO 98/01542 A1 | 1/1998 |
| WO | WO 98/01543 A1 | 1/1998 |
| WO | WO 99/01560 | 1/1998 |
| WO | WO 98/07838 A1 | 2/1998 |
| WO | WO 98/08938 A1 | 3/1998 |
| WO | WO 98/14592 | 4/1998 |
| WO | WO 98/14593 | 4/1998 |
| WO | WO 98/21343 | 5/1998 |
| WO | WO 98/37181 | 8/1998 |
| WO | WO 98/45450 A1 | 10/1998 |
| WO | WO 98/59040 A2 | 12/1998 |
| WO | WO 99/33998 | 7/1999 |
| WO | WO 99/38964 | 8/1999 |
| WO | WO 00/46355 A2 | 8/2000 |
| WO | WO 01/23004 | 4/2001 |
| WO | WO 02/16657 A1 | 2/2002 |
| WO | WO 02/16658 A1 | 2/2002 |
| WO | WO 02/070668 A2 | 9/2002 |
| WO | WO 02/072787 A2 | 9/2002 |
| WO | WO 02/090570 A2 | 11/2002 |
| WO | WO 02/090571 A2 | 11/2002 |
| WO | WO 02/101010 A2 | 12/2002 |
| WO | WO 03/000916 A2 | 1/2003 |
| WO | WO 03/016474 A2 | 2/2003 |

OTHER PUBLICATIONS

Berenstein, M., et al., Different efficacy of in vivo herpes simplex virus thymidine kinase gene transduction and ganciclovir treatment on the inhibition of tumor growth of murine and human melanoma cells and rat glioblastoma cells, Cancer Gene Therapy 6:358 (1999).

Bi, W., et al., An HSVtk-mediated local and distant antitumor bystander effect in tumors of head and neck origin in athymic mice, Cancer Gene Therapy 4:246 (1997).

Blackburn, R.V., et al., Adenoviral-mediated Transfer of Heat-inducible Double Suicide Gene into Prostate Carcinoma Cells, Cancer Res. 58:1358 (Apr. 1, 1998).

Bouali-Benazzouz, R., et al., Therapeutic efficacy of the thymidine kinase/ganciclovir system on large experimental gliomas: a nuclear magnetic resonance imaging study, Gene Therapy 6:1030 (1999).

Breakman, E., et al., Ganciclovir-mediated in vivo elimination of myeloid leukemic cells expressing the HSVtk gene induces HSVtk loss variants, Gene Therapy 6:1139 (1999).

Brand, K., et al., Tumor cell-specific transgene expression prevents liver toxicity of the adeno-HSVtk/GCV approach, Gene Therapy 5:1363 (1998).

Cao, G., et al., Effective and safe gene therapy for colorectal carcinoma using the cytosine deaminase gene directed by the carcinoembryonic antigen promoter, Gene Therapy 6:83 (1999).

Chase, M., et al., An oncolytic viral mutant that delivers the CYP2B1 transgene and augments cyclophosphamide chemotherapy, Nature Biotech. 16:444 (1998).

Chen, J., et al., Targeted In Vivo Delivery of Therapeutic Gene into Experimental Squamous Cell Carcinomas Using Anti-Epidermal Growth Factor Receptor Antibody: Immunogene Approach, Human Gene Therapy 9:2673 (1998).

Coffey, M.C., et al., Reovirus Therapy of Tumors with Activated Ras Pathway, Science 282:1332 (1998).

Delaney, C.L., et al., Conditional ablation of cerebellar astrocytes in postnatal transgenic mice, J. Neurosci. 16:6908 (1996).

Devereux, T.R., et al., DNA Methylation Analysis of the Promoter Region of the Human Telomerase Reverse Transcriptase (*hTERT*) Gene, Cancer Res. 59:6087 (1999).

Elshami, A.A., et al., The effect of promoter strength in adenoviral vectors containing herpes simplex virus thymidine kinase on cancer gene therapy in vitro and in vivo, Cancer Gene Therapy 4:213 (1997).

Greenberg, R.A., et al., Telomerase reverse transcriptase gene is a direct target of o-Myc but is not functionally equivalent in cellular transformation, Oncogene 18:1219(1999).

Hallenbeck, P.L., et al., A Novel Tumor-Specific Replication-Restricted Adenoviral Vector for Gene Therapy of Hepatocellular Carcinoma, Human Gene Therapy10:1721 (1999).

Heise, C.C., et al., Efficacy of a replication-competent adenovirus (ONYX-015) following intratumoral injection: Intraturmoral spread and distribution effects, Cancer Gene Therapy 6:499 (1999).

Helse, C.C., et al., Intravenous Adminstration of ONYX-015, a Selectively Replicating Adenovirus, Induces Antitumoral Efficacy, Cancer Res. 59:2623 (1999).

Harman, J.R., et al., In Situ Gene Therapy for Adenocarcinoma of the Prostate: A Phase I Clinical Trial, Human Gene Therapy 10:1239 (1999).

Heyman, R.A., et al., Thymidine kinase obliteration: creation of transgenic mice with controlled immune deficiency, Proc. Natl. Acad. Sci. USA 86:2698 (1989).

Horikawa, I., et al., Cloning and Characterization of the Promoter Region of *Human Telomerase Reverse Transcriptase* Gene, Cancer Res. 59:826 (1999).

Kanai, F., et al., In Vivo Gene Therapy for α-Fetoprotein-producing Hepatocellular Carcinoma by Adenovirus-mediated Transfer of Cytosine Deaminase Gene, Cancer Res. 57:461 (1997).

Kasuya, H., et al., Intraperitoneal Delivery of hrR3 and Ganciclovir Prolongs Survival in Mice with Disseminated Pancreatic Cancer, J. Surgical Onc., 72:136 (1999).

Klatzmann, D., et al., A Phase I/II Dose-Escalation Study of Herpes Simplex Virsu Type I Thymidine Kinase "Suicide" Gene Therapy for Metastatic Melanoma, Human Gene Therapy 9:2565 (1998).

Klatzmann, D., et al., A Phase I/II Study of Herpes Simplex Virus Type 1 Thymidine Kinase "Suicide" Gene Therapy for Recurrent Glioblastoma, Human Gene Therapy 9:2595 (1998).

Kramm, C.M., et al., Therapeutic Efficiency and Safety of a Second-Generation Replication-Conditional HSV1 Vector for Brain Turmor Gene Therapy, Human Gene Therapy 8:2057 (1997).

Kyo, S., et al., Estrogen Activates Telomerase, Cancer Res. 59:5917 (1999).

Kyo, S., et al., Sp1 cooperates with c-Myc to activate transcription of the human telomerase reverse transcriptase gene (hTERT), Nuclic Acids Res. 28:669 (2000).

Li, P.-X., et al., Differential chemosensitivity of breast cancer cells to ganciclovir teatment following adenovirus-mediated herpes simplex virus thymidine kinase gene transfer, Cancer Gene Therapy 6:179 (1999).

Mawatari, F., et al., Retrovirus-mediated gene therapy for heptocellular carcinoma: Selective and enhanced suicide gene expression regulated by human α-fetoprotein enhancer directly linked to its promoter, Cancer Gene Therapy 5:301 (1998).

Miyatake, S.-I., et al., Hepatoma-specific antitumor activity of an albumin enhancer/promoter regulated herpes simplex virus in vivo, Gene Therapy 6:584 (1999).

Oh, S., et al., In Vivo and in Vitro Analyses of Myc for Differential Promoter Activities of the Human Telomerase (hTERT) Gene in Normal and Tumor Cells, Biochem. Biophys. Res. Comm. 263:361 (1999).

Oh, S., et al., The Wilms' Tumor 1 Tumor Suppressor Gene Repress Transcription of the Human Telomerase Reverse Transcriptase Gene, J. Biol. Chem. 274:37473 (1999).

Pan, C.-X., et al., A novel tumor-specific gene therapy for bladder cancer, Med. Hypotheses 53:130 (1999).

Princen, F., et al., Repeated cycles of retrovirus-mediated HSVtk gene transfer plus ganciclovir increase survival of rats with peritoneal carcinomatosis, Gene Therapy 5:1054 (1998).

Robertson, M.W., III, et al., Use of tissue-specific promoter for targeted expression of the herpes simplex virus thymidine kinase gene in cervical carcinoma cells, Cancer Gene Therapy 5:331 (1998).

Rodriguez, R., et al., Prostate Attenuated Replication Competent Adenovirus (ARCA) CN706: A SelectiveCytotoxic for Prostate-specific Antigen-positive Prostate Cancer Cells, Cancer Res. 57:2559 (1997).

Rogulski, K.R., et al., Double Suicide Gene Therapy Augments the Antitumor Activity of a Replication-Competent Lytic Adenovirus through Enhanced Cytotoxicity and Radiosensitization, Human Gene Therapy 11:67 (2000).

Rothmann, T., et al., Replication of ONYX-015, a Potential Anti-cancer Adenovirus, Is Independent of p53 Status in Tumor Cells, J. Virology 72:9470 (1998).

Shand, N., et al., A Phase 1-2 Clinical Trial of Gene Therapy for Recurrent Glioblastoma Multiforme by Tumor Transduction with the Herpes Simplex Thymidine Kinase Gene Followed by Ganciclovir, Human Gene Therapy 10:2325 (1999).

Siders, W.M., et al., Melanoma-specific cytotoxicity induced by a tyrosinase promoter-enhancer/herpes simplex virus thymidine kinase adenovirus, Cancer Gene Therapy 5:281 (1998).

Smiley, W.R., et al., Establishment of Parameters for Optimal Transduction Efficiency and Antitumor Effects with Purified High-Titer HSV-TK Retroviral Vector in Established Solid Tumors, Human Gene Therapy 8:985 (1997).

Starman, D.H., et al., Adenovirus-Mediated Herpes Simplex Virus Thymidine Kinase/Ganciclovir Gene Therapy in Patients with Localized Malignancy: Results of a Phase I Clinical Trial in Malignant Mesothelioma, Human Gene Therapy 9:1083 (1998).

Su, H., et al., Tissue-specific expression of herpes simplex virus thymidine kinase gene delivered by adeno-associated virus inhibits the growth of human hepatocellular carcinoma in athymic mice, Proc. Natl. Acad. Sci. USA 94:13891 (1997).

Takakura, M., et al., Cloning of Human Telomerase Catalytic Subunit (hTERT) Gene Promoter and Identification of Proximal Core Promoter Sequences Essential for Transcriptional Activation in Immortalized and Cancer Cells, Cancer Res. 59:551 (1999).

Tanaka, T., et al., Adenovirus-mediated Prodrug Gene Therapy for Carcinoembryonic Antigen-producing Human Gastric Carcinoma Cells in Vitro, Cancer Res. 56:1341 (1998).

Toda, M., et al., treatment of Human Breast Cancer in a Brain Metastatic Model by G207, a Replication-Competent Multimutated Herpes Simplex Virus 1, Human Gene Therapy 9:2177 (1998).

Tronik-Le Roux, D., et al., Suppression of Erythro-Megakaryocytopolesis and the Induction of Reversible Thromboctpania in Mice Transgenic for the Thymidine Kinase Gene Targeted by the Platelet Glycoprotein αIIb Promoter, J. Exp. Med. 181:2141 (1995).

Wei, M.X., et al., Suicide Gene Therapy of Chemically Induced Mammary Tumor in Rat: Efficacy and Distant Bystander Effect, Cancer Res. 58:3529 (1998).

Wick, M., et al., Genomic organization and promoter characterization of the gene encoding the human telomerase reverse transcriptase (hTERT), Gene 232:97 (1999).

Wildner, D., et al., Therapy of Colon Cancer with Oncolytic Adenovirus is Enhanced by the Addition of Herpes Simplex Virus-*thymidine kinase*, Cancer Res. 59:410 (1999).

Wildner, O., et al., Enzyme Prodrug Gene Therapy: Synergistic Use of the Herpes Simplex Virus-Cellular Thymidine Kinase/Ganciclovir System and Thymidylate Synthase Inhibitors for the Treatment of Colon Cancer, Cancer Res. 59:5233 (1999).

Wildner, O., et al., Adenoviral vectors capable of replication improve the efficacy of HSVtk/GCV suicide gene therapy of cancer,Gene Therapy 6:57 (1999).

Wu, K.-J., et al., Direct activation of *TERT* transcription by c-MYC, Nature Genetics 21:220 (1999).

Yang, L., et al., Intercellular Communication Mediates the Bystander Effect During Herpes Simplex Thymidine Kinase/Ganciclovir-Based Gene Therapy of Human Gastrointestinal Tumor Cells, Human Gene Therapy 9:719 (1998).

Yu, D.-C., et al., Identification of the Transcriptional Regulatory Sequences of Human Kallikrein 2 and Their Use in the Construction of Calydon Virus 764, an Attenuated Replication Competent Adenovirus for Prostate Cancer Therapy, Cancer Res. 59:1498 (1999).

Yu, D.-C., et al., The Addition of Adenovirus Type 5 Region E3 Enables Calydon Virus 787 to Eliminate Distant Prostate Tumor Xenografts, Cancer Res. 59:4200 (1999).

U.S. Appl. No. 08/974,549, filed Nov. 19, 1997, "Human Telomerase Catalytic Subunit".

U.S. Appl. No. 09/244,438, "Telomerase Reverse Transcriptase Transcriptional Regulatory Sequences and Methods of Using", filed Feb. 4, 1999.

Cong, YS., et al., The Human Telomerase Catalytic Subunit hTERT: Organization of the Gene and Characterization of the Promoter, Human Molecular Genetics 8:137 (1999).

Chiu CP et al., Replicative senescence and cell immortality: the role of telomeres and telomerase, Proc Soc Exp Biol Med, 214(2):99 (1997).

Cooper MJ, Noninfectious gene transfer and expression systems for cancer gene therapy, Semin Oncol, 23(1):172 Review (1996).

Dachs GU et al., Targeting gene therapy to cancer: a review, Oncol Res. 9(6-7):313 (1997).

Danet-Dasnoyers GA et al., Telomerase vaccination has no detectable effect on SCID-repopulating and colony-forming activities in the bone marrow of cancer patients, Exp Hematol, 33(11):1275 (2005).

Durrant LG, Cancer vaccines, Anticancer Drugs, 8(8):727 (1997).

Harley CB et al., Telomeres and telomerase in aging and cancer, Curr Opin Genet Dev, 5(2):249 (1995).

Haung et al., Telomerae-dependent oncolytic adenovirus for cancer treatment, Gene Ther, 10(15):1241 (2003).

Huang Q et al., A novel conditionally replicative adenovirus vector targeting telomerase-positive tumor cells, Clin Cancer Res, 10(4):1439 (2004).

Holt SE, et al, Multiple pathways for the regulation of telomerase activity, Eur J Cancer, 33(5):761 (1997).

Holt SE, et al., Lack of cycle regulation of telomerase activity in human cells, Proc Natl. Acad Sci USA, 94:10687 (1997).

Irving J, et al., Contitionally replicative adenovirus driven by the human telomerase promoter provides broad-spectrum antitumor activity without liver toxicity, Cancer Gene Ther, 11(3):174 (2004).

Ito H et al., Autophagic cell death of malignant glioma cells induced by a conditionally replicating adenoviru, J Natl Cancer Inst, 98(9):625 (2006).

Kawashima T et al., Telomerase-Specific Replication-Selective Virotherapy for Human Cancer, Clinical Cancer Res 10:285 (2004).

Kolquist KA, et al., Expression of TERT in early premalignant lesions and a subset of cells in normal tissues, Nat Gen, 19(2):182 (1998).

Kuppuswamy M et al., Oncolytic adenovirus that overproduces ADP and replicates selectively in tumors due to hTERT promoter-regulated E4 gene expression, Gene Ther, 12(22):1608 (2005).

Lanson NA Jr et al., Replication of an adenoviral vector controlled by the human telomerase reverse transcriptase promoter causes tumor-selective tumor lysis, Cancer Res. 63(22):7936 (2003).

Lee HW et al., Essential role of mouse telomerase in highly proliferative organs, Nature, 392(6676):569 (1998).

Li Y et al., Dual promoter-controlled oncolytic adenovirus CG5767 has strong tumor selectivity and significant antitumor efficacy in preclinical models, Clin Cancer Res.11(24 Pt 1):8845 (2005).

Morrison SJ, et al., Telomerase activity in hemotopoietic cells is associated with self-renewal potential, immunity, 5(3):207 (1996).

Norrback KF, et al., Telomerase and telomerase in normal and malignant haematopoietic cells, Eur J Cancer, 33(5):774 (1997).

Pan C, et al., Changes in telomerase activity and telomere length during human T lymphocyte senescence, Exp Cell Res, 231(2):346 (1997).

Patterson A. et al., Molecular chemotherapy for breast cancer, Drugs Aging, 14(2):75 (1999).

Prowse KR et al., Develomental and tissue-specific regulation of mouse telomerase and telomerase length, Proc Natl Acad Sci U S A, 92(11):4818 (1995).

Reid TR et al., Effects of Onyx-015 among metastatic colorectal cancer patients that have failed prior treatment with 5-FU/leucovorin, Cancer Gene Ther, 12(8):673 (2005).

Ritz JM et al., A novel transgenic mouse model reveals humanlike regulation of 8-kbp human TERT gene promoter fragment in normal and tumor tissues, Cancer Res, 65(4):1107 (2005).

Ryan PC et al., Antitumor efficacy and tumor-selective replication with a single intravenous injection of OAS403, an oncolytic adenovirus dependent on two prevalent alterations in human cancer, Cancer Gene Ther, 11(8):555 (2004).

Ryan PC et al., Antitumor Efficacy and Tumor-Selective Replication with a Single intravenous injection of OAS403, an Oncolytic Adenovirus Dependent on Two Prevalent Alterations in Human Cancer, Cancer Gene Therapy pp. 1-15 (2004).

Sakabe H et al., Human cord blood-derived primitive progenitors are enriched in CD34+c-kit- cells: correlation between long-term culture- initiating cells and telomerase expression, Leukemia, 12(5):728 (1998).

Su et al., Potent antitumoral efficiacy of a novel replicative adenovirus CNHK300 targeting telomerase-positive cancer cells, J Cancer Res Clin Oncol, 130(10):591 (2004).

Suresh MR, Classification of tumor markers, Anticancer Res, 16(4B):2273 (1996).

Tahara H., et al., Immuno- histochemical detection of human telomerase catalytic component, hTERT, in human colorectal tumor and non-tumor tissue sections, Oncogene, 18(8):1561 (1999).

Thomson JA, et al., Embryonic stem cell lines derived from human blastocysts, Science, 282(5391):1145 (1998).

Wirth T et al., A telomerase-dependent condtionally replicating adenovirus for selective treatment of cancer, Cancer Res, 63(12):3181, (2003).

Yui J, et al., Telomerase activity in candidate stem cells from fetal liver and adult bone marrow, Blodd 9(9):3255 (1998).

Zou W et al., A novel oncolytic adenovirus targeting to telomerase activity in tumor cells with potent. Oncogene, 23(2):457 (2004).

Kim et al., Science 266:2011-2015, 1994, (cited by examiner in parent U.S. Appl. No. 09/615,039).

Kanazawa et al., Biochem. Biophys. Res. Commun. 225:570-576, 1996. (cited by examiner in parent U.S. Appl. No. 09/615,039).

1994 Genome Issue of Science (265:1981f).

Anderson & Young, "Quantitiave Filter Hybridization," in: *Nucleic Acid Hybridisation*, pp. 73-111 (1985).

Ausubel et al., in: *Current Protocols in Molecular Biology*, John Wiley & Sons, New York, NY (1989).

Autexier & Greider, "Functional Reconstitution of wild-type and mutat *Tetrahymena* telomerase," *Genes Devolp.* 8:563 (1994).

Autexier et al., "Reconstitution of human telomerase activity and identification of a minimal functional region of the human telomerase RNA," *EMBO J.* 15:5928-35 (1996).

Berger & Kimmel, "Guide to Molecular Cloning Techniques," *Meth. Enzymol. 152*, Academic Press, San Diego, CA (1987).

Beissman et al., "Addition of Telomere-Associated HeT DNA Sequences 'Heals' Broken Chromosome Ends in *Drosophila,*" *Cell 61*:663 (1990).

Bitter et al., "Expression and secretion vectors for yeast," *Meth. Enzymol. 153*:516 (1987).

Blackburn & Chiou, "Non-nucleosomal packaging of a tandemly repeated DNA sequence at termini of extrachromosomal DNA coding for rRNA in Tetrahymena," *Proc. Natl. Acad. Sci. USA 78*:2263 (1981).

Blackburn & Gall, "A tandemly repeated sequence at the termini of the extrachomosomal ribosomal RNA genes in *Tetrahymena,*" *J. Mol. Biol. 120*:33 (1978).

Blackburn, E. "Telomerases," *Ann. Rev. Biochem. 61*:113 (1992).

Bodnar et al., "Extension of Life-Span by Introduction of Telomearse into Normal Human Cells," *Science 279*:349-52 (1998).

Bradford, "A Rapid and Sensitive method for the Quantitation of Microgram Quantities of Protein Utilizing the Microgram Quantities of Protein Utilizing the Principle of Protein-Dye Binding," *Anal. Biochem. 72*:248 (1976).

Brand, K. et al., "Tumor cell-specific transgene expression prevents liver toxicity of the adeno-HSVtk/GCV approach," *Gene Therapy 5*:1363-71 (1998).

Braunstein et al., "Transcriptional silencing in yeast is associated with reduced nucleosome actylation," *Genes Dev. 7*:592 (1993).

Calvio et al., "Identification of hnRNP P2 as TLS/FUS using electrospray mass spectrometry," *RNA 1*:724 (1995).

Caruthers et al., "New chemical methods for synthesizing polynucleotides," *Nucleic Acids Res. Symp. Ser. 215*:223 (1990).

Chan & Tye, "Organization of DNA sequences and replication origins at yeast telomeres," *Cell 33*:563 (1983).

Colberge-Garapin et al., " A new dominant hybrid selective marker for higher eukaryotic cells," *J. Mol. Biol. 150*:1 (1981).

Cole et al., "The EBV-hybridoma technique and its application to human lung cancer," *Monoclonal Antibodies and Cancer Therapy*, Alan R. Liss Inc., New York, NY, pp. 77-96 (1985).

Collins et al., "Purification of Tetrahymena telomerase and cloning of genes encoding the two protein components of the enzyme," *Cell 81*:677 (1995).

Conrad et al., "RAP1 protein interacts with yeast telomers in vivo: overproduction alters telomere structure and decreases chromosome stability," *Cell 63*:739 (1990).

Coombs, *Dictionary of Biotechnology*, Stockton Press, New York, NY (1994).

Cote et al., "Generation of human monoclonal antibodies reactive with cellular antigens," *Proc. Natl. Acad. Sci. USA 80*:2026-30 (1983).

Counter et al., "The catalytic subunit of yeast telomerase." *Proc. Nat'l Acad Sci. U.S.A. 94*:9202-9207 (1997).

Creighton, *Proteins, Structures and Molecular Principles*, WH Freeman and Co, New York, NY (1983).

Dieffenbach & Dveksler, *PCR Primer, a Laboratory Manual*, Cold Spring Harbor Press, Plainview, NY (1995).

Duplaa et al., "Quantitative analysis of polymerase chain reaction products using biotinylated dUTP incorporation," *Anal. Biochem. 232*:229 (1993).

Fang et al., "Oxytricha telomere-binding protein: separable DNA-binding and dimerization domains of the α-subunit," *Genes Dev. 7*:870 (1993).

Feng et al., "The RNA Component of Human Telomerase," *Science 269*:1236 (1995).

GenBank AA281296, EST (Apr. 2, 1997).

GenBank accession No. AA299878 (1997).

GenBank accession No. AA311750 (1997).

Geron Corporation Press Release. Geron Corporation and Genetic Therapy, Inc. partner to develop cancer therapy (Jan. 7, 2002).

Gilley et al., "Altering specific telomerase RNA template residues affects active site function," *Genes Dev. 9*:2214 (1995).

Gottschling & Cech, "Chromatin Structure of the Molecular Ends of Oxytricha Macronuclear DNA: Phased Nucleosomes and a Telomeric Complex," *Cell 38*:501 (1984).

Gottschling & Zakian, "Telomere proteins: specific recognition and protection of the natural termini of Oxytricha macronuclear DNA," *Cell 47*:195 (1986).

Greenberg, R. et al., "Expression of mouse telomerase reverse transcriptase during development, differentiation and proliferation," *Oncogene 16*:1723-30 (1998).

Greenwood et al., "Phylogenetic relationships within the class oligohymenophorea, phylum ciliophora, inferred from the complete small subunit tRNA gene sequences of *Colpidium campylum, Glaucoma chattoni*, and *Opisthonecta henneguyi,*" *J. Mol. Evol. 3*:163 (1991).

Greider & Blackburn, "A telomeric sequence in the RNA of *Tetrahymena* telomere required for telomere repeat synthesis," *Nature* 337:331 (1989).

Greider & Blackburn, "Identification of a specific telomere terminal transferase activity in *Tetrahymena* extracts," *Cell* 43:405 (1985).

Greider, "Telomerase is processive," *Mol. Cell Biol.* 11:4572 (1991).

Greider, "Telomerase Length Regulation," *Ann. Rev. Biochem.* 65:337 (1996).

Gu et al., "Tumor-specific transgene expression from the human telomerase reverse transcriptase promoter enables targeting of the therapeutic effects of the Bax gene to cancers," *Cancer Res.* 60:5339 (2000).

Hampton et al., *Serological Methods a Laboratory Manual*, APS Press, St Paul, MN (1990).

Harrington et al., "A Mammalian Telomerase-Associated Protein", *Science* 275: 973-77 (1997).

Harrington et al., "Human telomerase contains evolutionarily conserved catalytic and structural subunits," *Genes Dev.* 11:3109-15 (1997).

Hartman & Mulligan, "Two dominant-acting selectable markers for gene transfer studies in mammalian cells," *Proc. Natl. Acad. Sci. USA* 85:8047 (1988).

Henderson & Blackburn, "An overhanging 3' terminus is a conserved feature of telomeres," *Mol. Cell. Biol.* 9:345 (1989).

Horn et al., "Synthesis of oligonucleotides on cellulose. Part II. Design and synthetic strategy to the synthesis of 22 oligodeoxynucleotides coding for gastric inhibitory polypeptide (GIP)," *Nucleic Acids Res. Symp. Ser.*, pp. 225-232 (1980).

Hudson et al., "An STS-based map of the human genome," *Science* 270:1945 (1995).

Huse et al., "Generation of a large combinatorial library of the immunoglobulin repertoire in phage lambda," *Science* 246:1275 (1989).

Kilian et al., "Isolation of a candidate human telomerase catlytic subunit gene, which reveals comlex splicing patterns in different cell types," *Hum. Mol. Genet.* 6:2011-19 (1997).

Kipling & Cooke, "Hypervariable ultra-long telomeres in mice," *Nature* 347:400 (1990).

Klobutcher et al., "All gene-sized DNA molecules in four species of hypotrichs have the same terminal sequence and an unusual 3'terminus," *Proc. Natl. Acad. Sci. USA* 78:3015 (1981).

Koehler & Milstein, "Continuous cultures of fused cells secreting antibody of predefined specificity," *Nature* 256:495-97 (1975).

Koga et al., "A Novel telomerase-specific gene therapy: Gene transfer of caspase-8 utilizing the human telomerase catalytic subunit gene promoter," *Hum. Gene Ther.* 11:1397- (2000).

Komata et al., "Treatment of malignant glioma cells with the transfer of constitutively active Caspase-6 using the human telomerase catalytic subunit (human telomerase reverse transcriptase) gene promoter," *Cancer Res.* 61:5796 (2001).

Kosbor et al., "The production of monoclonal antibodies from human lymphocytes," *Immunol. Today* 4:72 (1983).

Lamond & Sproat, "Isolation and characterization of ribonucleoprotein complexes," in: *RNA Processing, A Practical Approach*, pp. 103-140 Oxford University Press (1994).

Lamond et al., "Probing the structure and function of U2 snRNP with antisense oligonucleotides made of 2'-OMe RNA," *Cell* 58:383 (1989).

Lendvay et al., "Senescence mutants of *Saccharomyces cerevisiae* with a defect in telomere replication identify three additional EST genes," *Genetics* 144 (1996).

Lingner et al., "Purification of telomerase from *Euplotes aediculatus*: requirement of a primer 3' overhang" *Proc. Natl. Acad. Sci. USA* 93:10712 (1996).

Lingner et al., "Reverse transcriptase motifs in the catalytic subunit of telomerase," *Science* 276:561 (1997).

Lingner et al., "Telomerase and DNA End Replication: No Longer a Lagging Strand Problem?" *Science* 269:1533 (1995).

Ligner et al., "Telomerase RNAs of different ciliates have a common secondary structure and permuted template," *Genes Dev.* 8:1984 (1994).

Lowy et al., "Isolation of transforming DNA: Cloning the hamster aprt gene," *Cell* 22:817 (1980).

Lustig & Petes, "Identification of yeast mutants with altered telomere structure," *Proc. Natl. Acad. Sci. USA* 83:1398 (1986).

Maddox et al., "Elevated serum levels in human pregnancy of a molecule immunochemically similar to eosinophil granule major basic protein," *J. Exp. Med.* 158:1211 (1983).

Majumdar, A. et al., "Telomerase reverse transcriptase promoter drives efficacious tumor suicide gene therapy while preventing hepatoxicity encountered with constitutive promoters," *Gene Ther.* 8:568 (2001).

Makarov et al., "Nucleosomal Organization of Telomere-Specific Chromatin in Rat," *Cell* 73:775 (1993).

Martín-Rivera, L. et al., "Expression of mouse telomerase catalytic subunit in embryos and adult tissues," *Proc. Natl. Acad. Sci. USA* 95:10471-6 (1998).

McEachern & Blackburn, "Runaway telomere elongation caused by telomerase RNA gene mutation," *Nature* 376 :403 (1995).

Melby et al., "Quantitative measurement of human cytokine gene expression by polymerase chain reaction," *J. Immunol. Meth.* 159:235 (1993).

Merrifield, "Solid phase peptide synthesis. I. The synthesis of tetrapeptide," *J. Am Chem. Soc.* 85:2149 (1963).

Meyerson et al., "hEST2, the Putative Human Telomerase Catalytic Subunit Gene, Is Up-Regulated in Tumor Cells and during Immortalization," *Cell* 90:785-95 (1997).

Morris, K. et al., "Small Interfering RNA-Induced Transcriptional Gene Silencing in Human Cells," *Science* 305:1289 (2004).

Murry, *McGraw Hill Yearbook of Science and Technology*, McGraw Hill, New York, NY, pp. 191-196 (1992).

Nakamura et al., "Telomerase Catalytic Subunit Homologs from Fission Yeast and Human," *Science* 277:955 (1997).

Nakayama et al., "ATLP1: A Gene Encoding a Protein Component of Mammalian Telomerase Is a Novel Member of WD Repeats Family," *Cell* 88:875-84 (1997).

Nielsen et al., "Peptide nucleic acids (PNAs): Potential antisense and anti-gene agents," *Anticancer Drug Des.* 8:53-63 (1993).

Oka et al., "Inverted terminal repeat sequence in the macronuclear DNA of *Stylonychia pustulata,*" *Gene* 10:301 (1980).

Olovnikov, J., "A theory of marginotomy: The incomplete copying of template margin in enzymic synthesis of polynucleotides and biological significance of the phenomenon," *J. Theor. Biol.* 41:181 (1973).

Orlandi et al., "Cloning immunoglobulin variable domains for expression by the polymerase chain reaction," *Proc. Natl. Acad. Sci. USA* 86:3833 (1989).

Prescott, "The DNA of ciliated protozoa," *Microbiol. Rev.* 58:233 (1994).

Price, C. "Fluorescence in situ hybridization," *Blood Rev.* 7:127-34 (1993).

Rhodes et al., "Transformation of maize by electroporation of embryos," *Meth. Mol. Biol.* 55:121 (1995).

Roberge, et al., "A strategy for a convergent synthesis of N-linked glycopeptides on a solid support," *Science* 269:202 (1995).

Romero & Blackburn, "A conserved secondary structure for telomerase RNA," *Cell* 67:343 (1991).

Sambrook et al., *Molecular Cloning, A Laboratory Manual*, Cold Spring Harbor Press, Plainview, NY (1989).

Sandell et al., "Transcription of yeast telomere alleviates telomere position effect without affecting chromosome stability," *Proc. Natl. Acad. Sci. USA* 91:12061 (1994).

Sanger et al., "DNA sequencing with chain-terminating inhibitors," *Proc. Natl. Acad. Sci. USA* 74:5463 (1997).

Scharf, D. et al., "Heat stress promoters and transcription factors," *Results Probl. Cell Differ.* 20:125 (1994).

Shampay & Blackburn, "Generation of telomere-length heterogeneity in *Saccharomyces cerevisiae,*" *Proc. Nat. Acad. Sci. USA* 85:534 (1988).

Sheen & Levis, "Transposition of the LINE-like retrotransposon TART to Drosophila chromosome termini," *Proc. Natl. Acad. Sci. USA* 91:12510 (1994).

Shore, D., "Telomerase and telomere-binding proteins: controlling the endgame," *TIBS* 22:233-5 (1997).

Singer & Gottschling, "TLC1: Template RNA Component of *Saccharomyces cerevisiae* Telomerase," *Science* 266:404 (1994).

Starling et al., "Extensive telomere repeat arrays in mouse are hypervariable," *Nucleic Acids Res.* 18:6881 (1990).

Swanton et al., "Arrangement of Coding and Non-coding Sequences in the DNA Molecules Coding for rRNAs in *Oxytricha* sp.," *Chromosoma* 77:203 (1980).

Tommerup et al., "Unusual chromatin in human telomeres," *Mol. Cell. Biol.* 14:5777 (1994).

Trask, "Fluorescence in situ hybridization: applications in cytogenetics and gene mapping," *Trends Genet.* 7:149 (1991).

Verma et al., *Human Chromosomes: A Manual of Basic Techniques*, Pergamon Press, New York, NY (1988).

Watson, "Origin of concatemeric T7 DNA," *Nature New Biol.* 239:197 (1972).

Weinrich et al., "Reconstitution of human telomerase with the template RNA component hTR and the catalytic protien subunit hTRT," *Nat. Genet.* 17(4):498-502 (1997).

Wellinger et al., "Origin activation and formation of single-strand $TG_{1-3}$ tails occur sequentially in late S phase on a Yeast linear plasmid" *Mol. Cell. Biol.* 13:4057 (1993).

Wellinger et al., "*Saccharomyces* Telomeres Acquire Single-Strand $TG_{1-3}$ tails occur sequentially in late S phase on a Yeast linear plasmid" *Cell* 72:51 (1993).

Whitehead Institute/MIT Center for Genome Research, Genetic Map of the Mouse, Database Release 10 (Apr. 28, 1995).

Wigler et al., "Transfer of purified herpes virus thymidine kinase gene to cultured mouse cells," *Cell* 11:223-32 (1977).

Wigler et al., "Transformation of mammalian cells with an amplifiable dominant-acting gene," *Proc. Natl. Acad. Sci. USA* 77:3567 (1980).

Winter & Milstein, "Man-made antibodies," *Nature* 349:293 (1991).

Wright et al., "*Saccharomyces* telomeres assume a non-nucleosomal chromatin structure," *Genes Dev.* 6:197 (1992).

Yu et al., "In vivo alteration of telomere sequences and senescence caused by mutated Tetrahymena telomerase RNAs," *Nature* 344:126 (1990).

Zahler & Prescott, "Telomere terminal transferase activity in the hypotrichous ciliate Oxytricha nova and a model for replication of the ends of linear DNA molecules," *Nucleic Acids Res.* 16:6953 (1988).

Zakian, "Telomeres: Beginning to Understand the End," *Science* 270:1601 (1995).

Zaug et al., "Catalysis of RNA Cleavage by a Ribozyme Derived from the Group I Intron of Anabaena Pre-$tRNA^{Leu}$," *Biochemistry* 33:14935 (1994).

\* cited by examiner

Figure 3A

```
                        -290         -280         -270         -260         -250         -240         -230         -220         -210         -200
Human           CAGGCCGGCTCCCAGTGGATTCGCGGGCACAGACGCCCAGGACCGCGCTTCCCACGTGGCGGAGGGACTGGGGACCCCGTCCTGCCCCTTCA
                    ||                ||||   ||  |     || |  || | |  | ||||||  |    | |  |||   | |  |||  |  | |
Mouse           CA......GCAACCACTGAACTTGGCCGGGAACACACACCTGGTCCTCATGCAGCATTGTGACCATCAACGCAAAAGTACTATTGCTGCGACCCCGCC
                        -250         -240         -230         -220         -210         -200         -190         -180         -170

-190         -180         -170         -160         -150         -140         -130         -120         -110         -100
Human           CCTTTC..CAGCTCCGCCTCTCCGGCGGACCCCGCGGGTCCCCGACCCTCCCCGGCCCCCCAGCCCCTCCCGGGCCCCTCCCAGCCCCTCCCCTT
                   |||   |  ||  ||  ||         |||  | ||| |||        ||||    |||||||
Mouse           CCTTTCCCGCTACAACGCTTGGTCCGCTGCCTGAATCCCGCCCCTT.........TCCGTTCCCAGCCCCTCATCTTTTTCGTCGTGGACTCTCAGTGG
                        -160         -150         -140         -130         -120         -110         -100         -90

-90          -80          -70          -60          -50          -40          -30          -20          -10         +1
Human           CCTTTCCGGCGGCCCCGCCCTCTCCGCGGCGGAGTTTCAGGCAGCGCTGCGTCCTGCGCGTGTGGGAAAGCCCTGGCCCCGGCCACCCCCGCGATG-> hTERT ORF
                   |||      | ||| | |   |  | | |  |||||||||||  |||| ||||||||    |||   | ||||||  ||  ||||||||||||
Mouse           CCT......GGGTCCCTGGCTGTTTTCTAAGCACACACCCTTGCATCTTGGTTCC........ATCCCGGCCTTGAGCACAACAATG-> mTERT ORF
                        -80          -70          -60          -50          -40          -30          -20          -10         +1

Promoter/reporter constructs:
                                                                             -70          -60          -50          -40          -30          -20          -10          +1
hTERT sequence       ...CTCGCGGCGGAGTTTCAGGCAGCGCTGCGTCCTGCGCGTGTGGGAAAGCCCTGGCCCCGGCCACCCCCGCGATG-> hTERT ORF
                        |||||||||||||||||||||||||||||||||||||||||||||||||||||||||||||||||||||||||||
2.4 Kb reporter      ...CTCGCGGCGGAGTTTCAGGCAGCGCTGCGTCCTGCGCGTGTGGGAAAGCCCTGGCCCCGGCCACCCCCGAATTCGCCCACCATG-> SEAP ORF
                        |||||||||||||||||||||||||||||||||||||||||||| ||||||  |||||||||
ΔE reporter          ...CTCGCGGCGGAGTTTCAGGCAGCGCTGCGTCCTGCTGCGCACGTGGCAGTGGGAAGCCTGGAAGCCCTGGCCCCGGCCACCCCCGAATTCGCCCACCATG-> SEAP ORF
                        |||||||||||||||||||||||||||||||||||||
                                                              CGAATTCGCCCACCATG-> SEAP ORF
```

Day 7 Post Infection

Day 7 Post Infection

Figure 5

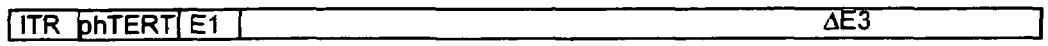

ITR = 1-356 of Ad2
E1 region begins at nt 549 of Ad2
ΔE3 = nt 27971-30937 of Ad2
phTERT = -36 to -239 "medium promoter"

ITR = 1-356 of Ad2
phTERT = -36 to -239 "medium promoter"
HI = truncated tripartite leader and splice donor site from adenovirus and a splice acceptor site from a mouse immunoglobulin
ΔE3 = nt 27971-30937 of Ad2
E1 region begins at nt 549 of Ad2

ITR = 1-356 of Ad2
phTERT = -36 to -239 "medium promoter"
HI = truncated tripartite leader and splice donor site from adenovirus and a splice acceptor site from a mouse immunoglobulin
ΔE3 = nt 27971-30937 of Ad2
E1 region begins at nt __498__ of Ad2

SEQUENCE LISTING

<160> NUMBER OF SEQ ID NOS: 23

<210> SEQ ID NO 1
<211> LENGTH: 15418
<212> TYPE: DNA
<213> ORGANISM: Homo sapiens
<220> FEATURE:
<223> OTHER INFORMATION: Human TERT promoter

<400> SEQUENCE: 1

| | | | | | | |
|---|---|---|---|---|---|---|
| gcggccgcga | gctctaatac | gactcactat | agggcgtcga | ctcgatcaat | ggaagatgag | 60 |
| gcattgccga | agaaaagatt | aatggatttg | aacacacagc | aacagaaact | acatgaagtg | 120 |
| aaacacagga | aaaaaagat | aagaaacga | aagaaaagg | gcatcagtga | gcttcagcag | 180 |
| aagttccatc | ggccttacat | atgtgtaagc | agaggccctg | taggagcaga | ggcaggggga | 240 |
| aaatacttta | agaataatg | tctaaaagtt | tttcaaatat | gaggaaaaac | ataaaaccac | 300 |
| agatccaaga | agctcaacaa | aacaaagcac | aagaaacagg | aagaaattaa | aagttatatc | 360 |
| acagtcaaat | tgctgaaaac | cagcaacaaa | gagaatatct | taagagtatc | agaggaaaag | 420 |
| agattaatga | caggccaaga | aacaatgaaa | acaatacaga | tttcttgtag | gaaacacaag | 480 |
| acaaaagaca | tttttttaaaa | ccaaaaggaa | aaaaatgct | acattaaaat | gtttttacc | 540 |
| cactgaaagt | atatttcaaa | acatatttta | ggccaggctt | ggtggctcac | acctgtaatc | 600 |
| ccagcactt | gggaggccaa | ggtgggtgga | tcgcttaagg | tcaggagttc | gagaccagcc | 660 |
| tggccaatat | agcgaaaccc | catctgtact | aaaaacacaa | aattagctg | ggtgtggtga | 720 |
| cacatgcctg | taatcccagg | tactcaggag | gctaaggcag | gagaattgct | tgaactggga | 780 |
| ggcagaggtg | gtgagccaag | attgcaccag | tgcactccag | ccttggtgac | agagtgaaac | 840 |
| tccatctcaa | aaacaaacaa | acaaaataca | tatacataaa | tatatatgca | catatatata | 900 |
| catatataaa | tatatataca | catatataaa | tctatataca | tatatacata | tatacacata | 960 |
| tataaatcta | tatacatata | tatacatata | taatatattt | acatatataa | atatatacat | 1020 |
| ataaaatat | acatatataa | atacatatat | aaatatacat | atataaatat | acatatataa | 1080 |
| atatacatat | ataaatatat | acatatataa | atatacatat | ataaatatat | atacatatat | 1140 |
| aaatatataa | atatacaagt | atatacaaat | atatacatat | ataaatgtat | atacgtatat | 1200 |
| acatatatat | ataaatatat | aaaaaaactt | ttggctgggc | acctttccaa | atctcatggc | 1260 |
| acatataagt | ctcatggtaa | cctcaaataa | aaaacatat | aacagataca | ccaaaaataa | 1320 |
| aaaccaataa | attaaatcat | gccaccagaa | gaaattacct | tcactaaaag | gaacacagga | 1380 |
| aggaaagaaa | gaaggaagag | aagaccatga | acaaccaga | aaacaaacaa | caaaacagca | 1440 |
| ggagtaattc | ctgacttatc | aataataatg | ctgggtgtaa | atggactaaa | ctctccaatc | 1500 |
| aaaagacata | gagtggctga | atggacgaaa | aaaacaagac | tcaataatct | gttgcctaca | 1560 |
| agaatatact | tcacctataa | agggacacat | agactgaaaa | taaaggaag | gaaaaatatt | 1620 |
| ctatgcaaat | ggaaaccaaa | aaagaacag | aactagctac | acttatatca | gacaaaaatag | 1680 |
| atttcaagac | aaaaagtaca | aaaagagaca | aagtaattat | ataataataa | agcaaaaaga | 1740 |
| tataacaatt | gtgaatttat | atgcgcccaa | cactgggaca | cccagatata | tacagcaaat | 1800 |
| attattagaa | ctaaggagag | agagagatcc | ccatacaata | atagctggag | acttcaccccc | 1860 |
| gcttttagca | ttggacagat | catccagaca | gaaaatcaac | caaaaaattg | gacttaatct | 1920 |
| ataatataga | acaaatgtac | ctaattgatg | tttacaagac | atttcatcca | gtagttgcag | 1980 |

-continued

```
aatatgcatt ttttcctcag catatggatc attctcaagg atagaccata tattaggcca   2040
cagaacaagc cattaaaaat tcaaaaaaat tgagccaggc atgatggctt atgcttgtaa   2100
ttacagcact ttggggaggg tgaggtggga ggatgtcttg agtacaggag tttgagacca   2160
gcctgggcaa aatagtgaga ccctgtctct acaaactttt ttttttaatt agccaggcat   2220
agtggtgtgt gcctgtagtc ccagctactt aggaggctga agtgggagga tcacttgagc   2280
ccaagagttc aaggctacgg tgagccatga ttgcaacacc acacaccagc cttggtgaca   2340
gaatgagacc ctgtctcaaa aaaaaaaaaa aaaattgaaa taatataaag catcttctct   2400
ggccacagtg gaacaaaacc agaaatcaac aacaagagga attttgaaaa ctatacaaac   2460
acatgaaaat taaacaatat acttctgaat aaccagtgag tcaatgaaga aattaaaaag   2520
gaaattgaaa aatttattta agcaaatgat aacggaaaca taacctctca aaacccacgg   2580
tatacagcaa aagcagtgct aagaaggaag tttatagcta taagcagcta catcaaaaaa   2640
gtagaaaagc caggcgcagt ggctcatgcc tgtaatccca gcactttggg aggccaaggc   2700
gggcagatcg cctgaggtca ggagttcgag accagcctga ccaacacaga gaaaccttgt   2760
cgctactaaa aatacaaaat tagctgggca tggtggcaca tgcctgtaat cccagctact   2820
cgggaggctg aggcaggata accgcttgaa cccaggaggt ggaggttgcg gtgagccggg   2880
attgcgccat tggactccag cctgggtaac aagagtgaaa ccctgtctca agaaaaaaaa   2940
aaaagtagaa aaacttaaaa atacaaccta atgatgcacc ttaaagaact agaaaagcaa   3000
gagcaaacta aacctaaaat tggtaaaaga aaagaaataa taaagatcag agcagaaata   3060
aatgaaactg aaagataaca atacaaaaga tcaacaaaat taaaagttgg tttttgaaa    3120
agataaacaa aattgacaaa cctttgccca gactaagaaa aaaggaaaga agacctaaat   3180
aaataaagtc agagatgaaa aaagagacat tacaactgat accacagaaa ttcaaaggat   3240
cactagaggc tactatgagc aactgtacac taataaattg aaaaacctag aaaaaataga   3300
taaattccta gatgcataca acctaccaag attgaaccat gaagaaatcc aaagcccaaa   3360
cagaccaata acaataatgg gattaaagcc ataataaaaa gtctcctagc aaagagaagc   3420
ccaggaccca atggcttccc tgctggattt taccaatcat ttaaagaaga atgaattcca   3480
atcctactca aactattctg aaaaatagag gaaagaatac ttccaaactc attctacatg   3540
gccagtatta ccctgattcc aaaaccagac aaaaacacat caaaaacaaa caaacaaaaa   3600
aacagaaaga aagaaaacta caggccaata tccctgatga atactgatac aaaaatcctc   3660
aacaaaacac tagcaaacca aattaaacaa caccttcgaa agatcattca ttgtgatcaa   3720
gtgggattta ttccagggat ggaaggatgg ttcaacatat gcaaatcaat caatgtgata   3780
catcatccca acaaaatgaa gtacaaaaac tatatgatta tttcacttta tgcagaaaaa   3840
gcatttgata aaattctgca cccttcatga taaaaaccct caaaaaacca ggtatacaag   3900
aaacatacag gccaggcaca gtggctcaca cctgcgatcc cagcactctg ggaggccaag   3960
gtgggatgat tgcttgggcc caggagtttg agactagcct gggcaacaaa atgagacctg   4020
gtctacaaaa aactttttta aaaaattagc caggcatgat ggcatatgcc tgtagtccca   4080
gctagtctgg aggctgaggt gggagaatca cttaagccta ggaggtcgag gctgcagtga   4140
gccatgaaca tgtcactgta ctccagccta gacaacagaa caagacccca ctgaataaga   4200
agaaggagaa ggagaaggga gaaaggaggg agaagggagg aggaggagaa ggaggaggtg   4260
gaggagaagt ggaaggggaa ggggaaggga aagaggaaga agaagaaaca tatttcaaca   4320
```

```
taataaaagc cctatatgac agaccgaggt agtattatga ggaaaaactg aaagcctttc    4380
ctctaagatc tggaaaatga caagggccca cttccaccac tgtgattcaa catagtacta    4440
gaagtcctag ctagagcaat cagataagag aaagaaataa aaggcatcca aactggaaag    4500
gaagaagtca aattatcctg tttgcagatg atatgatctt atatctggaa aagacttaag    4560
acaccactaa aaaactatta gagctgaaat ttggtacagc aggatacaaa atcaatgtac    4620
aaaaatcagt agtatttcta tattccaaca gcaaacaatc tgaaaagaa accaaaaaag    4680 cagctacaaa taaattaaa cagctaggaa ttaaccaaag aagtgaaaga tctctacaat    4740
gaaaactata aatatttgat aaagaaatt gaagagggca caaaaaaaga aaagatattc    4800
catgttcata gattggaaga ataaatactg ttaaaatgtc catactaccc aaagcaattt    4860
acaaattcaa tgcaatccct attaaaatac taatgacgtt cttcacagaa atagaagaaa    4920
caattctaag atttgtacag aaccacaaaa gacccagaat agccaaagct atcctgacca    4980
aaaagaacaa aactggaagc atcacattac ctgacttcaa attatactac aaagctatag    5040
taacccaaac tacatggtac tggcataaaa acagatgaga catggaccag aggaacagaa    5100
tagagaatcc agaaacaaat ccatgcatct acagtgaact cattttgac aaaggtgcca    5160 agaacatact ttggggaaaa gataatctct tcaataaatg gtgctggagg aactggatat    5220
ccatatgcaa ataacaata ctagaactct gtctctcacc atatacaaaa gcaaatcaaa    5280
atggatgaaa ggcttaaatc taaaaacctca aactttgcaa ctactaaaag aaaacaccgg    5340
agaaactctc caggacattg gagtgggcaa agacttcttg agtaattccc tgcaggcaca    5400
ggcaaccaaa gcaaaaacag acaaatggga tcatatcaag ttaaaaagct tctgcccagc    5460
aaaggaaaca atcaacaaag agaagagaca acccacagaa tgggagaata tatttgcaaa    5520
ctattcatct aacaaggaat taataaccag tatatataag gagctcaaac tactctataa    5580
gaaaaacacc taataagctg attttcaaaa ataagcaaaa gatctgggta gacatttctc    5640
aaaataagtc atacaaatgg caaacaggca tctgaaaatg tgctcaacac cactgatcat    5700
cagagaaatg caaatcaaaa ctactatgag agatcatctc accccagtta aaatggcttt    5760
tattcaaaag acaggcaata acaaatgcca gtgaggatgt ggataaaagg aaacccttgg    5820
acactgttgg tgggaatgga aattgctacc actatggaga acagtttgaa agttcctcaa    5880
aaaactaaaa ataaagctac catacagcaa tcccattgct aggtatatac tccaaaaaag    5940
ggaatcagtg tatcaacaag ctatctccac tcccacattt actgcagcac tgttcatagc    6000
agccaaggtt tggaagcaac ctcagtgtcc atcaacagac gaatggaaaa agaaaatgtg    6060
gtgcacatac acaatggagt actacgcagc cataaaaaag aatgagatcc tgtcagttgc    6120
aacagcatgg ggggcactgg tcagtatgtt aagtgaaata agccaggcac agaaagacaa    6180
acttttcatg ttctcccctta cttgtgggag caaaaattaa acaattgac atagaaatag    6240 aggagaatgg tggttctaga ggggtggggg acagggtgac tagagtcaac aataatttat    6300
tgtatgtttt aaaataacta aaagagtata attgggttgt tgtaacaca aagaaaggat    6360 aaatgcttga aggtgacaga taccccattt accctgatgt gattattaca cattgtatgc    6420
ctgtatcaaa atatctcatg tatgctatag atataaaccc tactatatta aaaattaaaa    6480
ttttaatggc caggcacggt ggctcatgtc cataatccca gcactttggg aggccgaggc    6540
ggtggatcac ctgaggtcag gagtttgaaa ccagtctggc caccatgatg aaaccctgtc    6600
tctactaaag atacaaaaat tagccaggcg tggtggcaca tacctgtagt cccaactact    6660
caggaggctg agacaggaga attgcttgaa cctgggaggc ggaggttgca gtgagccgag    6720
```

```
atcatgccac tgcactgcag cctgggtgac agagcaagac tccatctcaa aacaaaaaca   6780
aaaaaagaa gattaaaatt gtaatttta tgtaccgtat aaatatatac tctactatat    6840
tagaagttaa aaattaaaac aattataaaa ggtaattaac cacttaatct aaaataagaa   6900
caatgtatgt ggggtttcta gcttctgaag aagtaaaagt tatggccacg atggcagaaa   6960
tgtgaggagg gaacagtgga agttactgtt gttagacgct catactctct gtaagtgact   7020
taattttaac caaagacagg ctgggagaag ttaaagaggc attctataag ccctaaaaca   7080
actgctaata atggtgaaag gtaatctcta ttaattacca ataattacag atatctctaa   7140
aatcgagctg cagaattggc acgtctgatc acaccgtcct ctcattcacg gtgcttttt    7200
tcttgtgtgc ttggagattt tcgattgtgt gttcgtgttt ggttaaactt aatctgtatg   7260
aatcctgaaa cgaaaaatgg tggtgatttc ctccagaaga attagagtac ctggcaggaa   7320
gcaggtggct ctgtggacct gagccacttc aatcttcaag ggtctctggc caagacccag   7380
gtgcaaggca gaggcctgat gacccgagga caggaaagct cggatgggaa ggggcgatga   7440
gaagcctgcc tcgttggtga gcagcgcatg aagtgccctt atttacgctt tgcaaagatt   7500
gctctggata ccatctggaa aaggcggcca gcgggaatgc aaggagtcag aagcctcctg   7560
ctcaaaccca ggccagcagc tatgcgcccc acccgggcgt gtgccagagg gagaggagtc   7620
aaggcacctc gaagtatggc ttaaatcttt ttttcacctg aagcagtgac caaggtgtat   7680
tctgagggaa gcttgagtta ggtgccttct ttaaaacaga aagtcatgga agcacccttc   7740
tcaagggaaa accagacgcc cgctctgcgg tcatttacct ctttcctctc tccctctctt   7800
gccctcgcgg tttctgatcg ggacagagtg accccgtgg agcttctccg agcccgtgct    7860
gaggaccctc ttgcaaaggg ctccacagac ccccgccctg gagagaggag tctgagcctg   7920
gcttaataac aaactgggat gtggctgggg gcggacagcg acggcgggat tcaaagactt   7980
aattccatga gtaaattcaa cctttccaca tccgaatgga tttggatttt atcttaatat   8040
tttcttaaat ttcatcaaat aacattcagg agtgcagaaa tccaaaggcg taaaacagga   8100
actgagctat gtttgccaag gtccaaggac ttaataacca tgttcagagg gattttttcgc  8160
cctaagtact ttttattggt tttcataagg tggcttaggg tgcaagggaa agtacacgag   8220
gagaggactg ggcggcaggg ctatgagcac ggcaaggcca ccggggagag agtccccggc   8280
ctgggaggct gacagcagga ccactgaccg tcctccctgg gagctgccac attgggcaac   8340
gcgaaggcgg ccacgctgcg tgtgactcag gaccccatac cggcttcctg ggcccaccca   8400
cactaaccca ggaagtcacg gagctctgaa cccgtggaaa cgaacatgac ccttgcctgc   8460
ctgcttccct gggtgggtca agggtaatga agtggtgtgc aggaaatggc catgtaaatt   8520
acacgactct gctgatgggg accgttcctt ccatcattat tcatcttcac ccccaaggac   8580
tgaatgattc cagcaacttc ttcgggtgtg acaagccatg acaacactca gtacaaacac   8640
cactctttta ctaggcccac agagcacggc ccacacccct gatatattaa gagtccagga   8700
gagatgaggc tgctttcagc caccaggctg gggtgacaac agcggctgaa cagtctgttc   8760
ctctagacta gtagaccctg gcaggcactc ccccagattc tagggcctgg ttgctgcttc   8820
ccgagggcgc catctgccct ggagactcag cctgggtgc cacactgagg ccagccctgt    8880
ctccacaccc tccgcctcca ggcctcagct tctccagcag cttcctaaac cctgggtggg   8940
ccgtgttcca gcgctactgt ctcacctgtc ccactgtgtc ttgtctcagc gacgtagctc   9000
gcacggttcc tcctcacatg gggtgtctgt ctccttcccc aacactcaca tgcgttgaag   9060
```

```
ggaggagatt ctgcgcctcc cagactggct cctctgagcc tgaacctggc tcgtggcccc    9120
cgatgcaggt tcctggcgtc cggctgcacg ctgacctcca tttccaggcg ctccccgtct    9180
cctgtcatct gccggggcct gccggtgtgt tcttctgttt ctgtgctcct ttccacgtcc    9240
agctgcgtgt gtctctgtcc gctagggtct cggggttttt ataggcatag gacggggggcg   9300
tggtgggcca gggcgctctt gggaaatgca acatttgggt gtgaaagtag gagtgcctgt    9360
cctcacctag gtccacgggc acaggcctgg ggatggagcc cccgcagggg acccgcccctt   9420
ctctgcccag cacttttctg ccccccctccc tctggaacac agagtggcag tttccacaag   9480
cactaagcat cctcttccca aaagacccag cattggcacc cctggacatt tgccccacag    9540
ccctgggaat tcacgtgact acgcacatca tgtacacact cccgtccacg accgaccccc    9600
gctgttttat tttaatagct acaaagcagg gaaatccctg ctaaaatgtc ctttaacaaa    9660
ctggttaaac aaacgggtcc atccgcacgg tggacagttc ctcacagtga agaggaacat    9720
gccgtttata aagcctgcag gcatctcaag ggaattacgc tgagtcaaaa ctgccacctc    9780
catgggatac gtacgcaaca tgctcaaaaa gaaagaattt caccccatgg caggggagtg    9840
gttgggggggt taaggacggt gggggcagca gctgggggct actgcacgca ccttttacta   9900
aagccagttt cctggttctg atggtattgg ctcagttatg ggagactaac cataggggag    9960
tggggatggg ggaacccgga ggctgtgcca tctttgccat gcccgagtgt cctgggcagg   10020
ataatgctct agagatgccc acgtcctgat tcccccaaac ctgtggacag aacccgcccg   10080
gccccagggc ctttgcaggt gtgatctccg tgaggaccct gaggtctggg atccttcggg   10140
actacctgca ggcccgaaaa gtaatccagg ggttctggga agaggcgggc aggagggtca   10200
gagggggggca gcctcaggac gatggaggca gtcagtctga ggctgaaaag ggagggaggg   10260
cctcgagccc aggcctgcaa gcgcctccag aagctggaaa aagcggggaa gggaccctcc   10320
acggagcctg cagcaggaag gcacggctgg cccttagccc accagggccc atcgtggacc   10380
tccggcctcc gtgccatagg agggcactcg cgctgcccctt ctagcatgaa gtgtgtgggg   10440
atttgcagaa gcaacaggaa acccatgcac tgtgaatcta ggattatttc aaaacaaagg   10500
tttacagaaa catccaagga cagggctgaa gtgcctccgg gcaagggcag ggcaggcacg   10560
agtgattttaa tttagctatt ttattttatt tacttacttt ctgagacaga gttatgctct   10620
tgttgcccag gctggagtgc agcggcatga tcttggctca ctgcaacctc cgtctcctgg   10680
gttcaagcaa ttctcgtgcc tcagcctccc aagtagctgg gatttcaggc gtgcaccacc   10740
acacccggct aattttgtat ttttagtaga gatgggcttt caccatgttg gtcaggctga   10800
tctcaaaatc ctgacctcag gtgatccgcc cacctcagcc tcccaaagtg ctgggattac   10860
aggcatgagc cactgcacct ggcctatta accatttaaa aacttccctg gctcaagtc    10920
acacccactg gtaaggagtt catggagttc aatttcccct ttactcagga gttaccctcc   10980
tttgatattt tctgtaattc ttcgtagact ggggatacac cgtctcttga catattcaca   11040
gtttctgtga ccacctgtta tcccatggga cccactgcag gggcagctgg gaggctgcag   11100
gcttcaggtc ccagtggggt tgccatctgc cagtagaaac ctgatgtaga atcagggcgc   11160
gagtgtggac actgtcctga atctcaatgt ctcagtgtgt gctgaaacat gtagaaatta   11220
aagtccatcc ctcctactct actgggattg agcccctttcc ctatcccccc caggggcag   11280
aggagttcct ctcactcctg tggaggaagg aatgatactt tgttatttt cactgctggt    11340
actgaatcca ctgtttcatt tgttggtttg tttgttttgt tttgagaggc ggtttcactc   11400
ttgttgctca ggctggaggg agtgcaatgg cgcgatcttg gcttactgca gcctctgcct   11460
```

```
cccaggttca agtgattctc ctgcttccgc ctcccatttg gctgggatta caggcacccg    11520
ccaccatgcc cagctaattt tttgtatttt tagtagagac ggggggtgggg gtggggttca    11580 ccatgttggc caggctggtc tcgaacttct gacctcagat gatccacctg cctctgcctc    11640
ctaaagtgct gggattacag gtgtgagcca ccatgcccag ctcagaattt actctgttta    11700
gaaacatctg ggtctgaggt aggaagctca ccccactcaa gtgttgtggt gttttaagcc    11760
aatgatagaa ttttttttatt gttgttagaa cactcttgat gttttacact gtgatgacta    11820
agacatcatc agcttttcaa agacacacta actgcaccca taatactggg gtgtcttctg    11880
ggtatcagcg atcttcattg aatgccggga ggcgtttcct cgccatgcac atggtgttaa    11940
ttactccagc ataatcttct gcttccattt cttctcttcc ctcttttaaa attgtgtttt    12000
ctatgttggc ttctctgcag agaaccagtg taagctacaa cttaactttt gttggaacaa    12060
attttccaaa ccgcccctttt gccctagtgg cagagacaat tcacaaacac agccctttaa    12120
aaaggcttag ggatcactaa ggggatttct agaagagcga cccgtaatcc taagtattta    12180
caagacgagg ctaacctcca gcgagcgtga cagcccaggg agggtgcgag gcctgttcaa    12240
atgctagctc cataaataaa gcaatttcct ccggcagttt ctgaaagtag gaaaggttac    12300
atttaaggtt gcgtttgtta gcatttcagt gtttgccgac ctcagctaca gcatccctgc    12360
aaggcctcgg gagacccaga agtttctcgc cccttagatc caaacttgag caacccggag    12420
tctggattcc tgggaagtcc tcagctgtcc tgcggttgtg ccggggcccc aggtctggag    12480
gggaccagtg gccgtgtggc ttctactgct gggctggaag tcgggcctcc tagctctgca    12540
gtccgaggct tggagccagg tgcctggacc ccgaggctgc cctccaccct gtgcgggcgg    12600
gatgtgacca gatgttggcc tcatctgcca gacagagtgc cggggcccag ggtcaaggcc    12660
gttgtggctg gtgtgaggcg cccggtgcgc ggccagcagg agcgcctggc tccatttccc    12720 acccttctc gacgggaccg ccccgtgggg tgattaacag atttgggtg gtttgctcat    12780 ggtggggacc cctcgccgcc tgagaacctg caaagagaaa tgacgggcct gtgtcaagga    12840
gcccaagtcg cggggaagtg ttgcaggag gcactccggg aggtcccgcg tgcccgtcca    12900
gggagcaatg cgtcctcggg ttcgtcccca gccgcgtcta cgcgcctccg tcctccccttt    12960 cacgtccggc attcgtggtg cccggagccc gacgccccgc gtccggacct ggaggcagcc    13020
ctgggtctcc ggatcaggcc agcggccaaa gggtcgccgc acgcacctgt tcccagggcc    13080
tccacatcat ggcccctccc tcgggttacc ccacagccta ggccgattcg acctctctcc    13140 gctgggccc tcgctggcgt ccctgcaccc tgggagcgcg agcggcgcgc gggcggggaa    13200
gcgcggccca gaccccggg tccgcccgga gcagctgcgc tgtcggggcc aggccgggct    13260
cccagtggat tcgcgggcac agacgcccag gaccgcgctt cccacgtggc ggagggactg    13320
gggacccggg cacccgtcct gcccctthcac cttccagctc cgcctcctcc gcgcggaccc    13380
cgccccgtcc cgacccctcc cgggtccccg gcccagcccc ctccgggccc tcccagcccc    13440
tccccttcct ttccgcggcc ccgccctctc ctcgcggcgc gagtttcagg cagcgctgcg    13500
tcctgctgcg cacgtgggaa gccctggccc cggccacccc cgcgatgccg cgcgctcccc    13560
gctgccgagc cgtgcgctcc ctgctgcgca gccactaccg cgaggtgctg ccgctggcca    13620
cgttcgtgcg gcgcctgggg ccccagggct ggcggctggt gcagcgcggg gacccggcgg    13680 cttttccgcgc gctggtggcc cagtgcctgg tgtgcgtgcc ctgggacgca cggccgcccc    13740
ccgccgcccc ctccttccgc caggtgggcc tccccgggggt cggcgtccgg ctggggttga    13800
```

```
gggcggccgg ggggaaccag cgacatgcgg agagcagcgc aggcgactca gggcgcttcc    13860
cccgcaggtg tcctgcctga aggagctggt ggcccgagtg ctgcagaggc tgtgcgagcg    13920
cggcgcgaag aacgtgctgg ccttcggctt cgcgctgctg acggggccc  gcggggccc     13980 ccccgaggcc ttcaccacca gcgtgcgcag ctacctgccc aacacggtga ccgacgcact    14040 gcggggagc  ggggcgtggg ggctgctgct gcgccgcgtg ggcgacgacg tgctggttca    14100
cctgctggca cgctgcgcgc tctttgtgct ggtggctccc agctgcgcct accaggtgtg    14160
cgggccgccg ctgtaccagc tcggcgctgc cactcaggcc cggccccgc  cacacgctag    14220 tggaccccga aggcgtctgg gatgcgaacg ggcctgaaac catagcgtca gggaggccgg    14280 ggtcccctg  ggcctgccag ccccgggtgc gaggaggcgc ggggcagtg  ccagccgaag    14340 tctgccgttg cccaagaggc ccaggcgtgg cgctgcccct gagccggagc ggacgcccgt    14400
tgggcagggg tcctgggccc acccgggcag gacgcgtgga ccgagtgacc gtggtttctg    14460
tgtggtgtca cctgccagac ccgccgaaga agccacctct ttggagggtg cgctctctgg    14520
cacgcgccac tcccacccat ccgtgggccg ccagcaccac gcgggccccc catccacatc    14580
gcggccacca cgtccctggg acacgccttg tccccggtg  tacgccgaga ccaagcactt    14640
cctctactcc tcaggcgaca aggagcagct gcggccctcc ttcctactca gctctctgag    14700
gcccagcctg actggcgctc ggaggctcgt ggagaccatc tttctgggtt ccaggccctg    14760
gatgccaggg actccccgca ggttgccccg cctgccccag cgctactggc aaatgcggcc    14820
cctgtttctg gagctgcttg gaaccacgc  gcagtgcccc tacggggtgc tcctcaagac    14880
gcactgcccg ctgcgagctg cggtcacccc agcagccggt gtctgtgccc gggagaagcc    14940
ccagggctct gtggcggccc ccgaggagga ggacacagac ccccgtcgcc tggtgcagct    15000
gctccgccag cacagcagcc cctggcaggt gtacggcttc gtgcgggcct gcctgcgccg    15060
gctggtgccc ccaggcctct ggggctccag gcacaacgaa cgccgcttcc tcaggaacac    15120
caagaagttc atctccctgg ggaagcatgc caagctctcg ctgcaggagc tgacgtggaa    15180
gatgagcgtg cgggactgcg cttggctgcg caggagccca ggtgaggagg tggtggccgt    15240
cgagggccca ggccccagag ctgaatgcag taggggctca gaaaagggg  caggcagagc    15300 cctggtcctc ctgtctccat cgtcacgtgg gcacacgtgg cttttcgctc aggacgtcga    15360
gtggacacgg tgatcgagtc gactcccttt agtgagggtt aattgagctc gcggccgc     15418
```

<210> SEQ ID NO 2
<211> LENGTH: 7498
<212> TYPE: DNA
<213> ORGANISM: Mus sp.
<220> FEATURE:
<223> OTHER INFORMATION: Mouse TERT promoter

<400> SEQUENCE: 2

```
aagcttccag caaaccagtt agagctgagt tgatgctctg aagaagagaa aatgtagaga      60
cggtactgaa caaataatgt ctgggcaaac ctcagacatg aaaatggaag acgtggaaat     120
ccagagaact ctgagggaaa ataaaacaca actccaggtc atcacgggac tcatcaaact     180
gctgaggtgc agccacagag aaaaatctta aaatagccta gaacgatgca tgacacataa     240
agcacagaga agacgaagct gagtctgtct tgtaggaaca acttgagaag acctaaacca     300
ctgcaatgag tgcattctgc taacttagaa tttgctaccc agttcagatc caaaagggt     360 ttcacaaagt tcaacacaaa acagtagcag gagtggctaa ggggacaca  ctgataggaa     420 ttcagagaag tagggaatgc tcatatgggg acattacaaa atgtactttc atgttgctta     480
```

-continued

```
aatcatttta attgtcaacc acatcaagct aaataatgct ttgaggttca taacatttgg    540
agattatgtc tacactagca gagaaggcac caataacatc ccaattgcta gattctcata    600
gaatcatgag tcacaatggc agagacaggt tctgagagtg tgtccttgtt gtaaacagta    660
tgctctacaa actaagttgg ctgcaatatc actaggcagt gttgtcccat aagacaacta    720
tcacatatgt ggtccagtga tgaccaaagc atcttttagc attttgcaaa tgaagctcaa    780
atcgaatatg actaagctca tgcagtacaa atcaaggta cactgggata gtttaaaaga    840
tacatacttg tactggttag ttttgtgtca gcttgacaca gctggagtta tcacagagaa    900
aagagcttca gttgaggaaa ttcctccatg agatccagct atagggcatt ttctcaatta    960
gtgatcaagg ggggaaggcc ccttgtgggt gggaccatct ctgggctggt agtcttggtt   1020
ctataagaga gcaggctgag caagccagga gaagcaagcc agtaaagaac atccctccat   1080
ggcttctgca tcagctcctg ctccctgacc tgcttgagtt ccagttctaa cttctttcag   1140
tgatgaacag caatgtggaa atgaaagctg aataaaccct ttcctcccca ttttgcttct   1200
tggtcatgat gtttgtgcag gaatagaaac cctgactaag acaatactat aaaccctaaa   1260
agttgtaaac caaacacatg tgtttccatt aagccatcgt agaacaataa gtactcaacc   1320
ccaagtcaca taactataat cccagccttt gaaaaccggg atcaggaatt caaggctagc   1380
ctcatctata tgtaagatta aagcctgttt gggctgcatg agactttgtt tcaaaaaaaa   1440 aaaaaaaaa gcaaacaggc aaaaacaaac acaagacaag acagatgtaa aatgaaggag   1500
gggtagatgg gtcaagtaga aaatagcata ggaaacgagt caagtataga agaggtggta   1560
gtaaccagat catgcagaag gactcaaggc catctcctca cagtggctta ggtaggcctt   1620
cctctgctct tgagcagggg cagagttgcc gctttaagga ggggatcagt caccctttaag   1680 aactgaaaag ctgaacagtc ttctcaagtc agaagccagt ggcttcatct tacacctctc   1740
ttccttccct tgctactcat attggatctg atgatttgcc caacttggaa gaaacatctc   1800
ttctgaaggg tttcacagac accccatctt tccgagaaag gaccgcatag gctggccatc   1860
cctgtgctta caaaggaat aattaagaaa cttaattcca taagcaaata caacctttcc    1920
aagccccaag tggatgattt tatcttactg ttttttttata tctcatcaaa taacttccaa   1980
gggctcaaaa atccaaagat gtaaaaaagg aactgagctc tgtttgccaa gccatgagga   2040
ttaaataatg acattcaaag agattttgt gccctaagta ctttttattg gttttcatag    2100
atggtttaat gtgcaagatg aagcaaacag agatgggagt ggtatcagca tggattaagg   2160
tggcagttgt gagggagggg tactgagaga acaggacaag gtaacctatc taaggagagg   2220
ccaagttggc aagtgccagg gacttctaag cccagaacta gtacacattc cttaggtgct   2280
gtttgggaag tcagggagtc accagccttg ggatctataa aagtgcatgg tggcattcac   2340
tcacatactt cctgagctgt tcgatgttga tgaagtcgtg ggtatgagac tgttgtgtca   2400
gtgacaaact atgtaaatga gaatgattgt ttccatcttg accactaaga cgtaaaccgg   2460
ttccagtgat ctccaaacat ggcaagctac agcagagcag cagccccatc cagagccttg   2520
ccctggttct gaatggggga gaatccagtg ggagtcggtt gctgccagca tgttgggta    2580 gaaggctgga gcatgacagg tccccgagga tttcctgctt cctatatggg tagggatact   2640
tgaggtcctc tcttctacct ccttccctgc agggtttata acctctacca ctgtctgtct   2700
ctgggatagc tcctagggtg cagccccctcc ccaaaaaggc ctctccctgg cctcatgtct   2760
ctaagaacag ctttctaaag caggcctgtt acacaaaggc tccctttttcc tggcttcatc   2820
```

```
gttgctggta gacaacttcc actcgttttc cacttcagtt tcttctactc tgttgttatt    2880
tgattctgat gcttgaaccc agggttgtgt agtcagcaag tgctaccccc tccctcctct    2940
tctttgtttt tttgaggcag ggtctcattt tgcccaagtg gacctaaatt tcagcatgta    3000
gctggcctgg ttttgaatgc cttctcatcc tgcctctact tcccaagagt agcttacaag    3060
tgtgcaccac catgccccgc gatattctta ttttttgagac tgttttctat gctggtttct    3120
ttggggaact acactaaggt agcttacaag tgtgcaccac catgccccgc gatattctta    3180
ttttttgagac tgttttctat gctggtttct ttggggaact acactaaggt agcttcattg    3240
ttggcataaa tttctcagtt caggcccata tctcctaagt agcagaacta agcaaatctc    3300
aaacaaaccc ctcaaaaaga ctgatgtcca ctaaacggac ttctaaaata gctcctgtaa    3360
tcctgagcat ttacaaggcg gcagacctcc tataagggga taaatatgaa aacgcgcctg    3420
ttcaaatgct aggtcggtgg atagaagcaa tttcctcaga agctgaagg caccaaaggt     3480
tatatttgtt agcatttcag tgtttgccaa actcagctac agtagagatc acagattccc    3540
tatttcccag agattcaaaa ttcagcagcc cctctctaac tatggctcag agtcgtgtca    3600
ttacatatgc cccaacaaca accccacccc ctatcctacc cccgcctcac acgtgcaagt    3660
actatcacag ttgccaacct agcagagctg ccatcctaag gtcgaggtcg ccgctttggc    3720
tgtgtgcaca gcaagcgcc ctcacccaat ggccctggcc ttgctatggg tgcgtgagtt      3780
gagatgatgc tctggactct gaggtgaagg ccactggaac agtgaaaaaa gctaacgcag    3840
ggcttttacc tagtccccctt cctttggtgg tgggtgttta cggaacatat ttgggatctg    3900
agtgtatggt cgcaccacaa taaagcctta acctatatag tagaatttca gctgtaatca    3960
ttaagaactg agattgccac cacccaccctc actgtctgtg tcaaccacag caggctggag    4020
cagtcagctc aggaacaggc aaaaccttag gtccctccgc ctacctaacc ttcaatacat    4080
caaggatagg cttctttgct tgcccaaacc tcgccccagt ctagaccacc tgggattcc     4140
cagctcaggg cgaaaaggaa gcccgagaag cattctgtag agggaaatcc tgcatgagtg    4200
cgcccccttt cgttactcca acacatccag caaccactga acttggccgg ggaacacacc    4260
tggtcctcat gcaccagcat tgtgaccatc aacggaaaag tactattgct gcgacccccgc    4320
cccttccgct acaacgcttg gtccgcctga atcccgcccc ttcctccgtt cccagcctca    4380
tcttttcgt cgtggactct cagtggcctg ggtcctggct gttttctaag cacacccttg     4440
catcttggtt cccgcacgtg ggaggcccat cccggccttg agcacaatga cccgcgctcc    4500
tcgttgcccc gcggtgcgct ctctgctgcg cagccgatac cggaggtgt ggccgctggc     4560
aaccttgtg cggcgcctgg ggcccgaggg caggcggctt gtgcaacccg gggacccgaa     4620
gatctaccgc actttggttg cccaatgcct agtgtgcatg cactgggct cacagcctcc     4680
acctgccgac cttccttcc accaggtggg cctccaggcg ggatccccat gggtcagggg     4740
cggaaagccg ggaggacgtg ggatagtgcg tctagctcat gtgtcaagac cctcttctcc    4800
ttaccaggtg tcatccctga aagagctggt ggccagggtt gtgcagagac tctgcgagcg    4860
caacgagaga aacgtgctgg cttttggctt tgagctgctt aacgaggcca gaggcgggcc    4920
tcccatggcc ttcactagta gcgtgcgtag ctacttgccc aacactgtta ttgagaccct    4980
gcgtgtcagt ggtgcatgga tgctactgtt gagccgagtg ggcgacgacc tgctggtcta    5040
cctgctggca cactgtgctc tttatcttct ggtgccccccc agctgtgcct accaggtgtg    5100
tgggtctccc ctgtaccaaa tttgtgccac cacggatatc tggccctctg tgtccgctag    5160
ttacaggccc acccgacccg tgggcaggaa tttcactaac cttaggttct tacaacagat    5220
```

```
caagagcagt agtcgccagg aagcaccgaa acccctggcc ttgccatctc gaggtacaaa    5280
gaggcatctg agtctcacca gtacaagtgt gccttcagct aagaaggcca gatgctatcc    5340
tgtcccgaga gtggaggagg accccacag gcaggtgcta ccaaccccat caggcaaatc    5400
atgggtgcca agtcctgctc ggtcccccga ggtgcctact gcagagaaag atttgtcttc    5460
taaaggaaag gtgtctgacc tgagtctctc tgggtcggtg tgctgtaaac acaagcccag    5520
ctccacatct ctgctgtcac caccccgcca aaatgccttt cagctcaggc catttattga    5580
gaccagacat ttcctttact caggggaga tggccaagag cgtctaaacc cctcattcct    5640
actcagcaac ctccagccta acttgactgg ggccaggaga ctggtggaga tcatctttct    5700
gggctcaagg cctaggacat caggaccact ctgcaggaca caccgtctat cgcgtcgata    5760
ctggcagatg cggcccctgt ccaacagct gctggtgaac catgcagagt gccaatatgt    5820
cagactcctc aggtcacatt gcaggtttcg aacagcaaac caacaggtga cagatgcctt    5880
gaacaccagc ccaccgcacc tcatggattt gctccgcctg cacagcagtc cctggcaggt    5940
atatggtttt cttcgggcct gtctctgcaa ggtggtgtct gctagtctct ggggtaccag    6000
gcacaatgag cgccgcttct ttaagaactt aaagaagttc atctcgttgg ggaaatacgg    6060
caagctatca ctgcaggaac tgatgtggaa gatgaaagta gaggattgcc actggctccg    6120
cagcagcccg ggtgagcatg gctggtctcc agctgaatgc attaggggcc cagaaaaggg    6180
agacaatggg tggcagtaac ccaggtcccc agtggtgtgg tggctttatg cagtccgtgg    6240
ttggatgagt tccatcttat ggtctctgac tccaagctcc ctccagctcg ccttgcacaa    6300
actaagattc ttgtccaagc cctgggcagg ttctcagggc tggggacatt gtggtgaaca    6360
gataagcaga cggggagcat ggtggatagg agttctggca cagtgcacca gagagagtct    6420
ggaagcgcta gtgagagcta atgtaagggc ccgtggttcg ccaaagaatg ataaccccgg    6480
actcaaatag tatgccaaag caaggagcat tcattctgc agaaatcaag catgcaggtg    6540 ggggggggg gttgctctca ttccaagatg gagagacaac caagtataga ttttaagggg    6600 atcggggcc tttatcttac tccatctcta ggggcattcc attactgggg catgggttg    6660 gaggttggaa actgttaatg gggaggtctg gaaacttgct gccccattgt ccttgcttca    6720
ggctaggtag ctgagtagct tctaatggca ggatagtttc tgactagctg tctaaagtct    6780
ggggtgtttg tttttttgtt ttttctagta acttacttgc ctgaacttgc tcagtttta    6840 ggcctggtct cctggactgc caatttgaag cctattaagg agtcagcctg tctcactact    6900
ccaggttatc tataatcccc ctgtagaacg gtacctcact gataacaatg acagaccaac    6960
ataggaaccc actatccttg tggtgcatga gtttcaaagg ttcttctggt cctcccagtg    7020
tgcagatcca tgcttaagct atggtcctcc cagtgtgcag atccgtgctt aagctatggt    7080
cttgcagctg ctcgatctac aaagggtagg gtgaacgaag gaaagataaa tgaaaaaaaa    7140
aaaactgttt cctacagtga agatcgctgc cccatcttag ctatgagaag ggactgggga    7200
gtggagcctg gtgcataaaa gaggattgtg ttacttggaa ggctgcagag cctggactcc    7260
tgtgccctcc ttgcctggtt ttctgggttt aatgttgagg ttggccctct gtagtcacta    7320 cctgaccccct tcccttttcag ccaacccctcc ggttacaccc tgtgcatgta tggaaggggc    7380
caaacgccct atcctgctct cccttcccca aaattcttag gatattaaca acttatgggg    7440
aaaagatggt agagctatgt ttacccacca tgtacttggg aagctccgaa gtaagctt      7498
```

<210> SEQ ID NO 3

```
<211> LENGTH: 144
<212> TYPE: DNA
<213> ORGANISM: Artificial Sequence
<220> FEATURE:
<223> OTHER INFORMATION: NCO1 fragment containing hTERT upstream
      sequences and the first intron of hTERT from lambdaGPhi5
      into the NCO1 site of a pBBS167 (variant of pUC
      cloning vector with MCS)

<400> SEQUENCE: 3
atgaccatga ttacgaattc gagctcggta cccggggatc ctctagagtc gacctgcagg      60
catgcccatg gcaggcctcg cgcgcgagat ctcgggccca atcgatgccg cggcgatatc     120
gctcgaggaa gcttggcact ggcc                                            144

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: RA94

<400> SEQUENCE: 4
cccggccacc cccgcgaatt cgcgcgctcc ccgctgc                               37

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: RA91

<400> SEQUENCE: 5
ttgtactgag agtgcaccat atgcggtgtg catgctacgt aagaggttcc aactttcacc      60
ataat                                                                  65

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: RA96

<400> SEQUENCE: 6
aattgcgaag cttacg                                                      16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: RA97

<400> SEQUENCE: 7
aattcgtaag cttcgc                                                      16

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: oligo RA101

<400> SEQUENCE: 8
taggtaccga gctcttacgc gtgctagccc cacgtggcgg agggactggg gacccgggca      60
```

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: oligo RA100

<400> SEQUENCE: 9
taggtaccga gctcttacgc gtgctagccc ctcgctggcg tccctgcacc ctgggagc         58

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: RA107

<400> SEQUENCE: 10
cgtcctgctg cgcactcagg aagccctggc ccc                                    33

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: 'B' class
      E-Box just proximal to the hTERT initiating Met in
      pGRN262

<400> SEQUENCE: 11 cacgtg                                                                  6

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: changed
      'B' class E-Box just proximal to the hTERT initiating Met in
      pGRN262

<400> SEQUENCE: 12 cactca                                                                  6

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: COD1941

<400> SEQUENCE: 13
gatgaatgct catgattccg tatgg                                             25

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: COD2866

<400> SEQUENCE: 14
cagcatcttt tactttcacc agcgtttctg ggtgcgcaaa acaggaagg caaaatg           57

<210> SEQ ID NO 15
<211> LENGTH: 58

```
<212> TYPE: DNA
<213> ORGANISM: Artificial Sequence
<220> FEATURE:
<223> OTHER INFORMATION: Description of Artificial Sequence: RA104

<400> SEQUENCE: 15
taggtaccga gctcttacgc gtgctagccc ctcccagccc ctccccttcc tttccgcg        58

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: RA122

<400> SEQUENCE: 16
gaccgcgctt cccactcagc ggagggactg ggg                                   33

<210> SEQ ID NO 17
<211> LENGTH: 298
<212> TYPE: DNA
<213> ORGANISM: Homo sapiens
<220> FEATURE:
<223> OTHER INFORMATION: Human TERT promoter

<400> SEQUENCE: 17
caggccgggc tcccagtgga ttcgcgggca cagacgccca ggaccgcgct tcccacgtgg       60
cggagggact ggggacccgg gcacccgtcc tgccccttca ccttccagct ccgcctcctc     120
cgcgcggacc ccgccccgtc ccgacccctc ccgggtcccc ggcccagccc cctccgggcc     180
ctcccagccc ctcccctcc tttccgcggc cccgccctct cctcgcggcg cgagtttcag     240
gcagcgctgc gtcctgctgc gcacgtggga agccctggcc ccggccaccc ccgcgatg      298

<210> SEQ ID NO 18
<211> LENGTH: 262
<212> TYPE: DNA
<213> ORGANISM: Mus sp.
<220> FEATURE:
<223> OTHER INFORMATION: Mouse TERT promoter

<400> SEQUENCE: 18
cagcaaccac tgaacttggc cggggaacac acctggtcct catgcaccag cattgtgacc       60
atcaacggaa aagtactatt gctgcgaccc cgccccttcc gctacaacgc ttggtccgcc     120
tgaatcccgc cccttcctcc gttcccagcc tcatcttttt cgtcgtggac tctcagtggc     180
ctgggtcctg gctgttttct aagcacaccc ttgcatcttg gttcccgcac gtgggaggcc     240
catcccggcc ttgagcacaa tg                                               262

<210> SEQ ID NO 19
<211> LENGTH: 77
<212> TYPE: DNA
<213> ORGANISM: Homo sapiens
<220> FEATURE:
<223> OTHER INFORMATION: Human TERT promoter

<400> SEQUENCE: 19
ctcgcggcgc gagtttcagg cagcgctgcg tcctgctgcg cacgtgggaa gccctggccc       60
cggccacccc cgcgatg                                                     77

<210> SEQ ID NO 20
<211> LENGTH: 89
<212> TYPE: DNA
```

```
<213> ORGANISM: Artificial Sequence
<220> FEATURE:
<223> OTHER INFORMATION: Description of Artificial Sequence: E-box
      reporter construct

<400> SEQUENCE: 20
ctcgcggcgc gagtttcagg cagcgctgcg tcctgctgcg cacgtgggaa gccctggccc      60
cggccacccc cgcgaattcg cccaccatg                                         89

<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence: E-box
      reporter construct (with portion deleted)

<400> SEQUENCE: 21
ctcgcggcgc gagtttcagg cagcgctgcg tcctgctgcc gaattcgccc accatg           56

<210> SEQ ID NO 22
<211> LENGTH: 497
<212> TYPE: DNA
<213> ORGANISM: Homo sapiens
<220> FEATURE:
<223> OTHER INFORMATION: Human TERT promoter

<400> SEQUENCE: 22
actccagcat aatcttctgc ttccatttct tctcttccct cttttaaaat tgtgttttct      60
atgttggctt ctctgcagag aaccagtgta agctacaact taacttttgt tggaacaaat    120
tttccaaacc gccccttttgc cctagtggca gagacaattc acaaacacag ccctttaaaa   180
aggcttaggg atcactaagg ggatttctag aagagcgacc cgtaatccta agtatttaca    240
agacgaggct aacctccagc gagcgtgaca gcccagggag ggtgcgaggc ctgttcaaat    300
gctagctcca taaataaagc aatttcctcc ggcagtttct gaaagtagga aaggttacat    360
ttaaggttgc gtttgttagc atttcagtgt ttgccgacct cagctacagc atccctgcaa    420
ggcctcggga gacccagaag tttctcgccc cttagatcca aacttgagca acccggagtc    480
tggattcctg ggaagtc                                                    497

<210> SEQ ID NO 23
<211> LENGTH: 425
<212> TYPE: DNA
<213> ORGANISM: Mus sp.
<220> FEATURE:
<223> OTHER INFORMATION: Mouse TERT promoter

<400> SEQUENCE: 23
caagtgtgca ccaccatgcc ccgcgatatt cttattttttg agactgtttt ctatgctggt   60
ttctttgggg aactacacta aggtagcttc attgttggca taaatttctc agttcaggcc    120
catatctcct aagtagcaga actaagcaaa tctcaaacaa acccctcaaa aagactgatg    180
tccactaaac ggacttctaa aatagctcct gtaatcctga gcatttacaa ggcggcagac    240
ctcctataag ggagtaaata tgaaaacgcg cctgttcaaa tgctaggtcg gtggatagaa    300
gcaatttcct cagaaagctg aaggcaccaa aggttatatt tgttagcatt tcagtgtttg    360
ccaaactcag ctacagtaga gatcacagat tccctatttc ccagagattc aaaattcagc   420
agccc                                                                 425
```

TELOMERASE PROMOTERS SEQUENCES FOR SCREENING TELOMERASE MODULATORS

RELATED APPLICATIONS

This application is a divisional of U.S. Ser. No. 09/615,039, filed Jul. 11, 2000 now abandoned; which is a continuation of PCT/US00/03104 filed Feb. 4, 2000 designating the U.S. and published on Aug. 10, 2000 as WO 00/46355; which is a continuation-in-part of U.S. Ser. No. 09/244,438, filed Feb. 4, 1999 (now U.S. Pat. No. 6,777,203). This application is also a continuation-in-part of U.S. Ser. No. 10/325,810, filed Dec. 20, 2002 now U.S. Pat. No. 7,199,234 which is a continuation of U.S. Ser. No. 09/402,181 (now U.S. Pat. No. 6,610,839); which was the U.S. National Stage of PCT/US97/17885, filed Oct. 1, 1997, and published as WO 98/14593 on Apr. 9, 1998.

The afore-listed priority applications are hereby incorporated herein by reference in their entirety.

BACKGROUND

It has long been recognized that complete replication of the ends of eukaryotic chromosomes requires specialized cell components (Watson (1972) Nature New Biol. 239:197; Olovnikov (1973) J. Theor. Biol. 41:181). Replication of a linear DNA strand by conventional DNA polymerases requires an RNA primer, and can proceed only 5' to 3'. When the RNA primer bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo (Goldstein (1990) Science 249:1129; Martin (1979) Lab. Invest. 23:86; Goldstein (1969) Proc. Natl. Acad. Sci. USA 64:155; Schneider (1976) Proc. Natl. Acad. Sci. USA, 73:3584; Harley (1990) Nature 345:458-460; Hastie (1990) Nature 346:866-868; Counter (1992) EMBO J. 11:1921-1929; Bodnar (1998) Science 279:349-52).

The length and integrity of telomeres is thus related to entry of a cell into a senescent stage. Moreover, the ability of a cell to maintain (or increase) telomere length may allow a cell to escape senescence.

The maintenance of telomeres is a function of a specific DNA polymerase known as telomerase reverse transcriptase (TERT). Telomerase is a ribonucleoprotein (RNP) that uses a portion of its RNA moiety as a template for telomere repeat DNA synthesis (Morin (1997) Eur. J. Cancer 33:750). Consistent with the relationship of telomeres and TERT to the proliferative capacity of a cell, telomerase activity can be detected in highly replicative cell types such as stem cells. It is also active in an extraordinarily diverse set of tumor tissues, but is active in normal somatic cell cultures or normal tissues adjacent to a tumor (U.S. Pat. Nos. 5,629,154; 5,489,508; 5,648,215; and 5,639,613; Morin (1989) Cell 59:521; Shay (1997) Eur. J. Cancer 33:787; Kim (1994) Science 266:2011). Moreover, a correlation between the level of telomerase activity in a tumor and the likely clinical outcome of the patient has been reported (U.S. Pat. No. 5,639,613; Langford (1997) Hum. Pathol. 28:416).

Telomerase activity has also been detected in human germ cells, proliferating stem or progenitor cells, and activated lymphocytes. In somatic stem or progenitor cells, and in activated lymphocytes, telomerase activity is typically either very low or only transiently expressed (Chiu (1996) Stem Cells 14:239; Bodnar (1996) Exp. Cell Res. 228:58; Taylor (1996) J. Invest. Dermatol. 106:759).

The preceding summary is intended to introduce the field of the present invention to the reader. The cited references in this application are not to be construed as admitted prior art.

SUMMARY OF THE INVENTION

This disclosure explains that telomerase reverse transcriptase (TERT) is an ideal target for treating human diseases relating to cellular proliferation and senescence, such as cancer. The cis-acting transcriptional control elements of the this invention enable identification of trans-acting transcription control factors. The discovery and characterization of a promoter specific for TERT expressing cells has provided an opportunity to develop important new disease therapies.

An embodiment of the invention is an isolated, synthetic, or recombinant polynucleotide comprising a promoter sequence. A desirable feature of the promoter is that it preferentially promotes transcription of the genetic element in cells expressing TERT, such as cancer cells and other cells that can undergo extensive replication, such as stem cells. In some cases, the promoter sequence comprises about 15, 50, 100, 150, 200, 250, 500, 1000, 2500 or 13,000 bases in SEQ ID NO:1 or SEQ ID NO:2, or a nucleic acid molecule that hybridizes to such a portion of SEQ ID NO:1 or SEQ ID NO:2 under stringent conditions. Prototype promoter polynucleotides are human telomerase reverse transcriptase (hTERT) promoter or a mouse telomerase reverse transcriptase (mTERT) promoter, and variants thereof with the desired cell specificity, such as may be determined according to the reporter assays provided in this invention. In some cases, the promoter is distinct from SEQ. ID NO:6 of WO98/14593 (hTERT), or SEQ. ID NO:5 of WO99/27113 (mTERT), by virtue of sequence variation or increased length in the promoter region. Any feature of upstream or intron sequence that affects the rate of transcription in a particular cell can affect performance of the promoter.

A number of exemplary recombinant plasmids are provided that have the characteristic of preferentially promoting transcription in cells expressing TERT. One example (pGRN175 or phTERT175) is a promoter from position −117 to position −36, numbered from the translation initiation site (base 13545) of SEQ. ID NO:1—i.e., bases 13428-13509 of SEQ. ID NO:1. Another example (pGRN176 or phTERT176) is a promoter from position −239 to position −36, numbered from the translation initiation site (base 13545) of SEQ. ID NO:1—i.e., bases 13306-13509 of SEQ. ID NO:1. Other examples include pGRN316, a promoter from position −239 to +1 (bases 13306-13545 of SEQ. ID NO:1) and pGRN 350, a promoter from position −117 to +1 (bases 13428-13545 of SEQ. ID NO:1). Thus, preferential promotion in cells expressing TERT can be attained with a minimal promoter that is no longer than about 82 bases in length.

Transcriptional regulatory sequences have been discovered within the promoters of this invention, which provide methods for regulating transcription. In another embodiment of the invention, transcription of an encoding region under control of a promoter is regulated by modulating a transcriptional regulatory element within the promoter. The transcriptional regulatory element is modulated by a factor that binds the regulatory sequence, exemplified by SP1, SRY, HNF-3β, HNF-5, TFIID-MBP, E2F c-Myb, and particularly c-Myc, which (as shown in Example 8) can in some circumstances be modulated using a ligand for the estrogen receptor. Since c-Myc binds to a regulatory sequence known as an E box, another embodiment of the invention is a method for expressing a polynucleotide in a cell, comprising transducing the cell with a vector in which the polynucleotide is operably linked to an hTERT promoter comprising an E box, and then treating the cell to increase binding of a transcriptional regulatory factor such as c-Myc to the E box. The invention also provides a method for identifying such transcriptional regulatory sequences and trans-acting factors.

Another embodiment of this invention is a promoter that preferentially promotes transcription in TERT expressing cells, operably linked to an encoding sequence—for example, an encoding region for TERT, or an encoding region that is heterologous to the promoter, operably linked by way of genetic recombination. The encoded protein can be of any nature. In one example, the encoded protein can be a toxin, or a protein like Herpes virus thymidine kinase that renders a cell more susceptible to toxic effects of a drug. Other suitable toxins are given later in the disclosure. In another example, the encoded protein can be a reporter gene detectable by a signal such as fluorescence, phosphorescence, or enzymatic activity.

An embodiment of this invention of particular interest is an oncolytic virus having a genome in which a promoter is operably linked to a genetic element essential for replication of the virus. This includes genes involved in any stage of the replicative cycle, including replication of the genome, assembly of intact viral particles, and any other critical step. The promoter preferentially promotes transcription of the genetic element in cells expressing TERT, thereby promoting replication of the virus. Replication of the virus in a cancer cell leads to lysis of the cancer cell. In general, oncolytic viruses are useful for treatment of any disease associated with expression of TERT in cells at the disease site.

Replication-conditional viruses of this invention include but are not limited to adenovirus of any subtype, wherein the adenovirus E1a region is placed under control of a promoter of this invention. Since a wide variety of cancer cells and some other types of hyperplasias overexpress TERT, oncolytic adenovirus replicates in affected cells, leading to their eradication. It is readily appreciated that other aspects of this invention can be incorporated into oncolytic viruses—such as an encoding region for a toxin or other protein that would compromise viability of the cancer cell. The viruses are selected by using candidate oncoviruses to infect a cell or a plurality of cells expressing TERT and not expressing TERT, and then choosing candidates on the basis of whether they preferentially kill the cells expressing TERT.

Other embodiments of the invention are polynucleotide sequence fragments obtained upstream from the hTERT encoding region, variants, homologs, and hybridizing polynucleotides. These products are of interest in part for cis-acting regulatory functions of transcription, including not only promoter activity, but also repressor activity, the binding of trans-acting regulatory factors, and other functions described in the disclosure. Further embodiments of this invention include cells and organisms introduced with the polynucleotides, vectors, and viruses of this invention; methods of treating medical conditions associated with elevated TERT expression, and pharmaceutical compositions for the treatment of such conditions.

A further understanding of the nature and advantages of the invention will be appreciated from the disclosure that follows.

DESCRIPTION OF THE DRAWINGS

FIG. 3 is a sequence alignment, comparing regions of the hTERT promoter (SEQ. ID NO:1) with that of mTERT (SEQ. ID NO:2). Regions of homology were used to identify regulatory elements. FIG. 3(A) shows the position of conserved cis-acting transcriptional regulatory motifs, including the E-box (the Myc/Max binding site, indicated by shading) and the SP1 sites (underlined). The lower panel illustrates the proximal sequences of the 2.5 kb hTERT and E-box reporter constructs, including the region deleted in the E-box reporter construct, as described in Example 8.

The cells tested were as follows: FIG. 4(A): BJ (foreskin fibroblast); IMR-90 (lung fibroblast); WI-38 (lung fibroblast); cells of non-malignant origin. FIG. 4(B): DAOY (medulloblastoma); HeLa (cervical carcinoma); HT1080 (fibrosarcoma). Other cells tested: A549 (lung carcinoma) AsPC-1 and BxPC-3 (adenocarcinoma, pancreas). The results show that the hTERT-regulated oncolytic virus specifically lyses cancer cells, in preference to cell lines that don't express telomerase reverse transcriptase at a substantial level. This is in contrast to oncolytic virus regulated by a constitutive promoter like CMV promoter, which lyses cells non-specifically.

FIG. 5 is a series of maps showing construction of oncolytic adenovirus, made conditionally replicative by placing the E1a replication under control of an hTERT promoter. The first construct comprises the Inverted Terminal Repeat (ITR) from the adenovirus (Ad2); followed by the hTERT medium-length promoter (pGRN176) operably linked to the adenovirus E1a region; followed by the rest of the adenovirus deleted for the E3 region (ΔE3). This construct was used in the virus infection experiments shown in FIG. 4. The second conditionally replicative adenovirus construct shown in the Figure comprises an additional sequence in between the hTERT promoter and the E1a region. The HI sequence is an artificial intron engineered from adenovirus and immunoglobulin intron splice sequences. The third adenovirus construct is similar, except that the E1a region used is longer at the 5' end by 51 nucleotides.

DETAILED DESCRIPTION

The invention provides novel isolated polynucleotides comprising cis-acting transcriptional control sequences of telomerase reverse transcriptase genes. The polynucleotides of the invention include those based on or derived from genomic sequences of untranscribed, transcribed and intron regions of TERT genes, including the human and mouse homolog. Cis-acting TERT transcriptional control sequences include those that regulate and modulate timing and rates of transcription of the TERT gene. The TERT promoter sequences of the invention include cis-acting elements such as promoters, enhancers, repressors, and polynucleotide sequences that can bind factors that influence transcription.

Isolating and Characterizing Human TERT Promoter Sequences

As described in Example 1, the hTERT promoter (SEQ ID NO:1) was obtained by sequencing an insert from a lambda phage isolated from a human genomic library. This lambda clone is designated λGφ5 and has been deposited at the ATCC, under Accession No. 98505. Lambda Gθ5 contains a 15.3 kilobase pair (kbp) insert including approximately 13,500 bases upstream from the hTERT coding sequence. These hTERT promoter sequences were further subcloned into plasmids. A Not1 fragment (SEQ ID NO:1) from λGφ5 containing the hTERT promoter sequences was subcloned in opposite orientations into the Not1 site of pUC derived plasmids (designated pGRN142 and pGRN143, respectively, and pGRN142 was sequenced.

In SEQ ID NO:1, the hTERT genomic insert begins at residue 44 and ends at residue 15375. The start of the cDNA from which it was derived begins at residue 13490. The hTERT ATG translation initiation codon starts at residue 13545. Untranscribed hTERT promoter sequences lie downstream of residue 44 and upstream of the encoding region, and may also reside in the first Intron. In immortal cells, a reporter gene driven by a sequence upstream of the TERT coding sequence drove expression as efficiently as the positive control (containing an SV40 early promoter and enhancer). Certain TERT promoter sequences of the invention also include intron sequences.

Figure 3B:
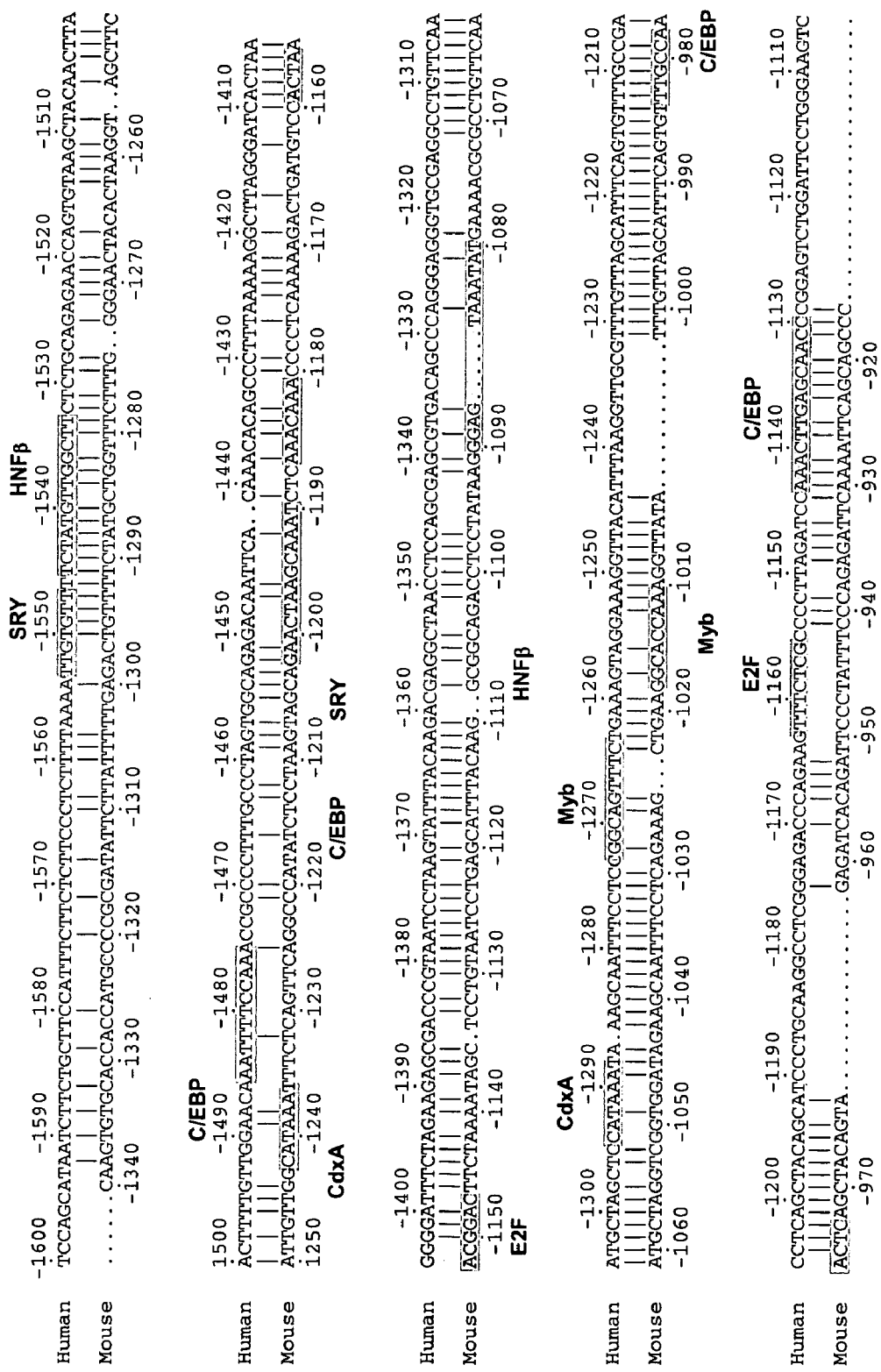
FIG. 3(B) shows the identification of other regulatory elements. The numbering shown is calculated from the translation initiation site.

Identification of Cis-Acting Transcriptional Regulatory Sequences in the Human and Mouse TERT Promoter To identify cis-acting transcriptional regulatory sequences in human TERT and mouse TERT sequences 5' to their respective TERT coding sequence, the human and mouse promoter sequences were analyzed for sequence identity. Alignment of the first 300 bases upstream of the human and mouse coding sequences indicated a number of conserved regions, and putative cis-acting transcriptional regulatory sequences were identified (FIG. 3(A)).

In particular, located at residues −34 to −29 upstream of the human TERT translation start site (ATG, A at 13545 of SEQ ID NO: 1) and at residues −32 to −27 upstream of the mouse TERT translation start site (ATG) are highly conserved motifs. They correspond to a cis-acting motif known to interact with c-Myc, the so-called "E-box" or "Myc/Max binding site." Specifically, they are highly conserved with respect to the core nucleotides that comprise the E-box, nucleotides flanking the E-box and position of the E-box relative to the translation start site. A second E-box was identified at residues −242 to −237 upstream of the human TERT translation start site. This second E-box was not conserved in the mouse promoter. These observations support the finding that the conserved Myc binding site, by interacting with c-Myc as a trans-acting transcriptional regulatory factor, plays a major role in TERT promoter regulation and telomerase expression.

Sequence alignment identified additional conserved cis-acting transcriptional regulatory elements in the TERT gene promoter. For example, two SP1 binding sites, located at residue −168 to −159 and residue −133 to −121 relative to the TERT translation start site were identified, which are highly conserved between the mouse and human TERT promoters. Binding sites (cis-acting sequences) for a number of other transcription factors, including the sex determining region Y gene product (SRY), hepatic nuclear factors 3-β and 5, TFIID-MBP, E2F and c-Myb were also found within this region of both the mouse and human promoters.

Further analysis of the human and mouse TERT promoter sequences indicated other regions of sequence conservation. In particular, a region with a high degree of sequence identity between human and mouse promoter was found between residue −1106 and residue −1602 upstream of the human TERT translation start site and residue −916 and residue −1340 upstream of the mouse TERT translation start site (FIG. 3(B)). Thus, the invention provides cis-acting sequences specific for the modulation of TERT transcription. In a preferred embodiment, the methods of the invention use these human and mouse TERT-specific transcriptional regulatory motifs to identify and isolate TERT-specific, and other, trans-acting transcriptional regulatory factors.

The invention also provides the reagents and methods for screening and isolating trans-acting TERT transcriptional regulatory factors. Alternative embodiments include novel in vitro and cell-based in vivo assay systems to screen for TERT promoter binding agents (trans-acting TERT transcriptional regulatory factors) using the nucleic acids of the invention.

c-Myc is a Potent Activator of TERT Gene Transcription

Use of recombinant constructs comprising TERT promoter sequences of the invention has, for the first time, demonstrated that c-Myc acts as a potent activator of telomerase activity by direct interaction with cis-acting regulatory sequences in the TERT promoter. c-Myc acts through the rapid up-regulation of hTERT gene expression (Example 8). Significantly, the studies demonstrate that transcriptional activation of the hTERT promoter by c-Myc can be abrogated by deletion or mutation of a single cis-acting regulatory sequence, the "Myc/Max binding site," within the hTERT promoter. Furthermore, the ability of an inducible c-Myc to enhance expression of hTERT is resistant to inhibition of protein synthesis.

TERT Promoter Used to Drive Heterologous Gene Sequences

The invention also provides constructs in which the TERT promoter sequences of the invention are operably linked to a heterologous gene (in a preferred embodiment, a structural gene). In this way the heterologous gene is transcribed in the same cells at the same time the natural TERT transcript would be expressed. Thus, when the construct is expressed in a transformed cell or transgenic (non-human) animal, the heterologous gene (and protein, if the gene is a coding sequence) is expressed in the same temporal pattern over the same cell range as the wild type, TERT promoter-driven TERT gene.

These constructs are useful for TERT promoter-based assays, for example, to identify biological modulators of TERT and telomerase activity. In alternative embodiments, the heterologous coding sequence operably linked to a TERT promoter of the invention is a marker gene (e.g., alkaline phosphatase, SEAP; β-galactosidase), a modified TERT structural gene or a TERT antisense, a therapeutic gene (e.g., a cytotoxic gene such as thymidine kinase).

In a further embodiment, cytopathic viruses are provided, in particular human cytopathic viruses, such as modified adenovirus or Herpes virus. Viruses, such as adenovirus or Herpes virus require essential virally encoded genes to proliferate and lyse specific cells. If any one of these essential viral genes were modified such that expression of the essential element would be driven by the TERT promoter, proliferation of the virus, and its cytopathic effects, would be restricted to telomerase-expressing cells, in particular tumor cells.

Definitions

The following terms are defined infra to provide additional guidance to one of skill in the practice of the invention.

The term "amplifying" as used herein incorporates its common usage and refers to the use of any suitable amplification methodology for generating or detecting recombinant or naturally expressed nucleic acid. For example, the invention provides methods and reagents (including specific oligonucleotide PCR primer pairs) for amplifying naturally expressed or recombinant nucleic acids of the invention in vivo or in vitro. An indication that two polynucleotides are "substantially identical" can be obtained by amplifying one of the polynucleotides with a pair of oligonucleotide primers or pool of degenerate primers (e.g., fragments of an TERT promoter sequence) and then using the product as a probe under stringent hybridization conditions to isolate the second sequence (e.g., the TERT promoter sequence) from a genomic library or to identify the second sequence in a Northern or Southern blot.

As used herein, the term "TERT promoter" includes any TERT genomic sequences capable of driving transcription in telomerase activity positive cells. Thus, TERT promoters of the invention include without limitation cis-acting transcriptional control elements and regulatory sequences that are involved in regulating or modulating the timing and/or rate of transcription of a TERT gene. For example, the TERT promoter of the invention comprises cis-acting transcriptional control elements, including enhancers, promoters, transcription terminators, origins of replication, chromosomal integration sequences, 5' and 3' untranslated regions, exons and introns, which are involved in transcriptional regulation. These cis-acting sequences typically interact with proteins or other biomolecules to carry out (turn on/off, regulate, modulate, etc.) transcription.

One of skill in the art will appreciate that the hTERT and mTERT promoter sequences provided herein are exemplary only, and that they may be used as a basis to produce numerous versions of TERT promoters, i.e., promoters that are capable of driving transcription in telomerase activity positive cells. For example, while it is shown herein that a sequence comprising 2447 nucleotides of the disclosed hTERT promoter can drive expression in this manner (pGRN350), one of skill in the art will appreciate that such activity may be obtained using longer or shorter promoter sequences. Furthermore, one of skill in the art will appreciate that promoter sequences that vary from those sequences provided herein by, for example, nucleotide additions, deletions or substitutions may also be used to obtain expression in telomerase activity positive cells. Such variants will share a specified minimum level of structural (sequence) similarity to the disclosed TERT promoter sequences, which similarity may be defined in terms of either sequence identity to the disclosed TERT promoter sequences, or the ability to hybridize to the disclosed sequences at specified levels of hybridization stringency. For example, variant TERT promoters include promoters that hybridize to the TERT promoters disclosed herein (at 37° C. in a buffer of 40% formamide, 1 M NaCl, and 1% SDS, followed by a wash in 1×SSC at 45° C.), and which are capable of driving transcription in telomerase activity positive cells. Other variant TERT promoters include promoters that share at least about 80%, 90%, 95%, 98% or 100% sequence identity with the disclosed TERT promoters. Sequence identity is calculated by first aligning the polynucleotide being examined with the reference counterpart, and then counting the number of residues shared between the sequences being compared as a percentage of the region under examination. No penalty is imposed for the presence of insertions or deletions, but insertions or deletions are permitted only where clearly required to readjust the alignment. The percentage is given in terms of residues in the sequence being examined that are identical to residues in the comparison or reference sequence.

The determination that a promoter is capable of driving transcription in telomerase activity positive cells can be routinely performed as described in Examples 2 and 5. Briefly, the promoter to be tested is operably linked to a coding region that encodes a detectable protein such as alkaline phosphatase or green fluorescent protein. This construct is then introduced into telomerase activity positive (TAP) and telomerase activity negative (TAN) cells. Detection of the detectable protein in the TAP cells but not in the TAN cells, or of an elevated level of the detectable protein in the TAP compared to the TAN cells (preferably at least a three-fold difference) indicates that the promoter is a TERT promoter.

A promoter is said to "preferentially promote transcription" in a cell having a particular phenotype if the level of transcription is at least about 3-fold higher in cells of that phenotype than cells that lack the phenotype. Promoters of this invention preferentially promote transcription in cells expressing TERT, including diseased cells where the disease is associated with overexpression of TERT, such as cancer. There is preferential transcription if the relative increase in cells expressing the stated phenotype is at least about 3-fold, 10-fold, 30-fold or 100-fold higher compared with cells that don't have the phenotype, in order of increasing preference. Promoters that show lower levels of specificity in an assay where just two types of cells are compared may be tested using a larger panel. One skilled in the art will know that TERT positive cells include various types of cancer cells, various types of progenitor cells and stem cells, and under certain conditions, B and T lymphocytes. Suitable negative controls include primary cultures and established cell lines of mature differentiated cells of most tissue types.

In alternative embodiments, the TERT promoter sequence comprises TERT sequences upstream of the translation start site (ATG), for example, in one embodiment, the hTERT promoter comprises residues 44 to 13545 of SEQ ID NO:1. Other embodiments include sequences starting within about one to 5 nucleotides of a translation start codon (for example in SEQ ID NO:1 or SEQ ID NO:2) and ending at about 50, 100, 150, 200, 250, 500, 1000, 2500 or 13500 nucleotides upstream of the translation start codon. Such embodiments can optionally include other regulatory sequences, such as, exon and/or intron sequences. Another embodiment includes TERT intron sequences with regulatory activity, as described in Example 2. hTERT promoters of the invention also include sequences substantially identical (as defined herein) to an exemplary hTERT promoter sequence of the invention, having the sequence set forth by SEQ ID NO:1. Similarly, mTERT promoters of the invention also include sequences substantially identical to an exemplary mTERT promoter sequence of the invention, having the sequence set forth by SEQ ID NO:2.

The term "heterologous" when used with reference to portions of a nucleic acid, indicates that the nucleic acid comprises two or more subsequences which are not found in the same relationship to each other in nature. For instance, the nucleic acid is typically recombinantly produced, having two or more sequences from unrelated genes arranged in a manner not found in nature; such as a promoter sequence of the invention operably linked to a polypeptide coding sequence that, when operably linked, does not reform the naturally occurring TERT gene. For example, the invention provides recombinant constructs (expression cassettes, vectors, viruses, and the like) comprising various combinations of promoters of the invention, or subsequences thereof, and heterologous coding sequences.

As used herein, "isolated," when referring to a molecule or composition, such as an hTERT promoter sequence, means that the molecule or composition is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined by analytical chemistry techniques such as polyacrylamide gel electrophoresis (PAGE), agarose gel electrophoresis or high pressure liquid chromatography (HPLC).

As used herein, the terms "nucleic acid" and "polynucleotide" are used interchangeably, and include oligonucleotides. They also refer to synthetic and/or non-naturally occurring nucleic acids (including nucleic acid analogues or modified backbone residues or linkages). The terms also refer to deoxyribonucleotide or ribonucleotide oligonucleotides in either single-or double-stranded form. The terms encompass nucleic acids containing known analogues of natural nucleotides. The term also encompasses nucleic acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (Strauss-Soukup (1997) Biochemistry 36:8692-8698), and benzyl-phosphonate linkages (Samstag (1996) Antisense Nucleic Acid Drug Dev 6:153-156).

As used herein, the term "operably linked" refers to a functional relationship between two or more nucleic acid segments. Typically, it refers to the functional relationship of a transcriptional regulatory sequence to a transcribed sequence. For example, a TERT promoter sequence of the invention, including any combination of cis-acting transcriptional control elements, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, "recombinant" refers to a polynucleotide synthesized or otherwise manipulated in vitro, to methods of using recombinant polynucleotides to produce gene products in cells or other biological systems, or to a polypeptide ("recombinant protein") encoded by a recombinant polynucleotide. "Recombinant means" also encompass the ligation of nucleic acids having coding or promoter sequences from different sources into an expression cassette or vector for expression of a fusion protein; or, inducible, constitutive expression of a protein (for example, a TERT promoter of the invention operably linked to a heterologous nucleotide, such as a polypeptide coding sequence).

As used herein, the "sequence" of a gene (unless specifically stated otherwise) or nucleic acid refers to the order of nucleotides in the polynucleotide, including either or both strands of a double-stranded DNA molecule—the sequence of both the coding strand and its complement, or of a single-stranded nucleic acid molecule. For example, in alternative embodiments, the promoter of the invention comprises untranscribed, untranslated, and intron TERT sequences, as set forth in the exemplary SEQ ID NO:1 and SEQ ID NO:2.

As used herein, the term "transcribable sequence" refers to any sequence which, when operably linked to a cis-acting transcriptional control element, such as the TERT promoters of the invention, and when placed in the appropriate conditions, is capable of being transcribed to generate RNA.

The terms "identical" or percent "identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement of a sequence. For example, in alternative embodiments, nucleic acids within the scope of the invention include those with a nucleotide sequence identity that is at least about 60%, at least about 75-80%, about 90%, and about 95% of the exemplary TERT promoter sequence set forth in SEQ ID NO:1 (including residues 44 to 13544 of SEQ ID NO:1) or SEQ ID NO:2, and the intron TERT sequences capable of driving a reporter gene in telomerase positive cells. Two sequences with these levels of identity are "substantially identical." Thus, if a sequence has the requisite sequence identity to a TERT promoter sequence or subsequence of the invention, it also is a TERT promoter sequence within the scope of the invention. Preferably, the percent identity exists over a region of the sequence that is at least about 25 nucleotides in length, more preferably over a region that is at least about 50-100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Alignment of sequences can be conducted by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pair-wise alignments to show relationship and percent sequence identity. It also plots a tree or dendrogram, showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pair-wise alignment of the two most similar sequences, producing a cluster of two aligned sequences. This cluster is then aligned to the next most related sequence or cluster of aligned sequences. Two clusters of sequences are aligned by a simple extension of the pair-wise alignment of two individual sequences. The final alignment is achieved by a series of progressive, pair-wise alignments. The program is run by designating specific sequences and their amino acid or nucleotide coordinates for regions of sequence comparison and by designating the program parameters. Using PILEUP, a reference sequence is compared to another sequence to determine the percent sequence identity relationship (whether the second sequence is substantially identical and within the scope of the invention) using the following parameters: default gap weight (3.00), default gap length weight (0.10), and weighted end gaps. PILEUP can be obtained from the GCG sequence analysis software package (Devereaux (1984) Nucl. Acids Res. 12:387-395).

Another example of algorithm that is suitable for determining percent sequence identity is the BLAST algorithm, which is described in Altschul (1990) J. Mol. Biol. 215:403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues, always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a word-length (W) of 11, an expectation (E) of 10, M=5, N=4, and a comparison of both strands. For amino acid sequences, the BLASTP program uses as default parameters a word-length (W) of 3, an expectation (E) of 10, and the BLOSUM62 scoring matrix (Henikoff (1989) Proc. Natl. Acad. Sci. USA 89:10915).

The BLAST algorithm also performs a statistical analysis of the similarity between two sequences (Karlin (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "selectively (or specifically) hybridizes to" refers to the binding, duplexing, or hybridizing of a molecule to a particular nucleotide sequence under stringent hybridization conditions when that sequence is present in a complex mixture (such as total cellular or library DNA or RNA), wherein the particular nucleotide sequence is detected at least twice background, preferably 10 times background. In one embodiment, a nucleic acid can be determined to be within the scope of the invention according to its ability to hybridize under stringent conditions to another nucleic acid (such as the exemplary sequences described herein).

The phrase "stringent hybridization conditions" refers to conditions under which a probe will primarily hybridize to its target subsequence, typically in a complex mixture of nucleic acid, but to no other sequences. Stringent conditions are sequence-dependent and will be different in different circumstances, depending on the length of the probe. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (≈10 to about 50 nucleotides) and at least about 60° C. for long probes (greater than about 50 nucleotides). Stringent conditions may also be achieved with the addition of destabilizing agents such as formamide. For selective or specific hybridization, a positive signal (identification of a nucleic acid of the invention) is about 5-10 times background hybridization. "Stringent" hybridization conditions that are used to identify substantially identical nucleic acids within the scope of the invention include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C., for long probes. For short probes, stringent hybridization conditions include hybridization in a buffer comprising 50% formamide, 5×SSC and 1% SDS at room temperature or hybridization in a buffer comprising 5×SSC and 1% SDS at 37° C.-42° C., both with a wash of 0.2×SSC and 0.1% SDS at 37° C. –42° C. However, as is apparent to one of ordinary skill in the art, hybridization conditions can be modified depending on sequence composition. Moderately stringent hybridization conditions include a hybridization in a buffer of 40% formamide, 1 M NaCl, and 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

General Techniques

The TERT promoter sequences of the invention and nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, bacterial, yeast, insect or mammalian systems. Alternatively, these nucleic acids can be chemically synthesized in vitro. Techniques for the manipulation of nucleic acids, such as subcloning into expression vectors, labeling probes, sequencing, and hybridization are well described in the scientific and patent literature. Molecular Cloning: A Laboratory Manual (2nd Ed.), Vols. 1-3, Cold Spring Harbor Laboratory, (1989) ("Sambrook"); Current Protocols In Molecular Biology, Ausubel, Ed. John Wiley & Sons, Inc., New York (1997) ("Ausubel"); Laboratory Techniques In Biochemistry And Molecular Biology: Hybridization With Nucleic Acid Probes, Part I. Theory and Nucleic Acid Preparation, Tijssen, ed. Elsevier, N.Y. (1993). Nucleic acids can be analyzed and quantified by any of a number of techniques, including NMR, spectrophotometry, radiography, electrophoresis, capillary electrophoresis, high pressure liquid chromatography (HPLC), thin layer chromatography (TLC), and hyperdiffusion chromatography, fluid or gel precipitin reactions, immunodiffusion (single or double), immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis, RT-PCR, quantitative PCR, other nucleic acid or target or signal amplification methods, radiolabeling, scintillation counting, and affinity chromatography.

Preparing hTERT Promoter Sequences

Certain embodiments of the invention are TERT promoters comprising genomic sequences 5' (upstream) of an hTERT or mTERT transcriptional start site, and intron sequences. TERT promoters contain cis-acting transcriptional regulatory elements involved in TERT message expression. It will be apparent that, in addition to the nucleic acid sequences provided in hTERT SEQ ID NO:1 or mTERT SEQ ID NO:2, additional TERT promoter sequences can be readily obtained using routine molecular biological techniques. For example, additional hTERT genomic (and promoter) sequence can be obtained by screening a human genomic library using an hTERT nucleic acid probe having a sequence or subsequence as set forth in SEQ ID NO:1 (a nucleic acid sequence is within the scope of the invention if it hybridizes under stringent conditions to an hTERT promoter sequence of the invention). Additional hTERT or mTERT genomic sequence can be readily identified by "chromosome walking" techniques, as described by Hauser (1998) Plant J 16:117-125; Min (1998) Biotechniques 24:398-400. Other useful methods for further characterization of TERT promoter sequences include those general methods described by Pang (1997) Biotechniques 22:1046-1048; Gobinda (1993) PCR Meth. Applic. 2:318; Triglia (1988) Nucleic Acids Res. 16:8186; Lagerstrom (1991) PCR Methods Applic. 1:111; Parker (1991) Nucleic Acids Res. 19:3055.

In some embodiments, the promoter sequence comprises at least about 15, 50, 100, 150, 200, 250, 500, 1000, 2500 or 13,000 bases in SEQ ID NO:1 or SEQ ID NO:2. Included is a nucleic acid molecule comprising a TERT promoter, including but not limited to hTERT or mTERT, optionally linked to a heterologous sequence. The promoter may comprise about 100 to about 200, 200 to about 400, 400 to about 900, or 900 to about 2500, or 2500 to about 5000 nucleotides upstream of a translational start site. In other embodiments, the promoter comprises a sequence that hybridizes with SEQ. ID NO:1 or 2. Exemplary are promoter sequences that preferentially promote transcription in cells expressing telomerase reverse transcriptase. Such sequences can be readily identified using the assays provided elsewhere in this disclosure and in the Examples, in which candidate promoter sequences are operably linked to the encoding region for a reporter protein, and then transfected into cells with known TERT activity to determine the specificity.

The invention provides oligonucleotide primers that can amplify all or any specific region within the TERT promoter sequence of the invention, including specific promoter and enhancer subsequences. The nucleic acids of the invention can also be generated or measured quantitatively using amplification techniques. Using the TERT promoter sequences of the invention (as in the exemplary hTERT SEQ ID NO:1 or mTERT SEQ ID NO:2), the skilled artisan can select and design suitable oligonucleotide amplification primers. Amplification methods include polymerase chain reaction (PCR Protocols, A Guide To Methods And Applications, ed. Innis, Academic Press, N.Y. (1990) and PCR Strategies (1995), ed. Innis, Academic Press, Inc., N.Y., ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. USA, 86:1173); and, self-sustained sequence replication (Guatelli (1990) Proc. Natl. Acad. Sci. USA, 87:1874); Q β-replicase amplification (Smith (1997) J.

Clin. Microbiol. 35:1477-1491, automated Q-β replicase amplification assay; Burg (1996) Mol. Cell. Probes 10:257-271) and other RNA polymerase mediated techniques (NASBA, Cangene, Mississauga, Ontario); Berger (1987) Methods Enzymol. 152:307-316, Sambrook, Ausubel, Mullis (1987) U.S. Pat. Nos. 4,683,195, and 4,683,202; Arnheim (1990) C&EN 36-47; Lomell J. Clin. Chem., 35:1826 (1989); Van Brunt (1990) Biotechnology, 8:291-294; Wu (1989) Gene 4:560; Sooknanan (1995) Biotechnology 13:563-564. Once amplified, TERT genomic DNA, TERT promoter sequences, and the like, can be cloned, if desired, into any of a variety of vectors using routine molecular biological methods; methods for cloning in vitro amplified nucleic acids are described in Wallace, U.S. Pat. No. 5,426,039.

The invention includes TERT promoter sequences that have been modified in a site-specific manner to alter, add to, or delete some or all of the promoter's functions. For example, specific base pairs can be modified to alter, increase or decrease the binding affinity to trans-acting transcriptional regulatory factors, thus modifying the relative level of transcriptional activation or repression. Modifications can also change secondary structures of specific subsequences, such as those associated with many cis-acting transcriptional elements. Site-specific mutations can be introduced into nucleic acids by a variety of conventional techniques, well described in the scientific and patent literature. Illustrative examples include site-directed mutagenesis by overlap extension polymerase chain reaction (OE-PCR), as in Urban (1997) Nucleic Acids Res. 25:2227-2228; Ke (1997) Nucleic Acids Res 25:3371-3372, and Chattopadhyay (1997) Biotechniques 22:1054-1056, describing PCR-based site-directed mutagenesis "megaprimer" method; Bohnsack (1997) Mol. Biotechnol. 7:181-188; Ailenberg (1997) Biotechniques 22:624-626, describing site-dire mutagenesis using a PCR-based staggered re-annealing method without restriction enzymes; Nicolas (1997) Biotechniques 22:430-434, site-directed mutagenesis using long primer-unique site elimination and exonuclease III. Modified TERT promoter sequences of the invention can be further produced by chemical modification methods. Belousov (1997) Nucleic Acids Res. 25:3440-3444; Frenkel (1995) Free Radic. Biol. Med. 19:373-380; Blommers (1994) Biochemistry 33:7886-7896.

The invention also provides antisense oligonucleotides capable of binding TERT promoter regions which, at least in part, modulate TERT transcription and telomerase activity. For example, antisense oligonucleotides that form triplexes with promoter regions inhibit the activity of that promoter. Joseph (1997) Nucleic Acids Res. 25:2182-2188; Alunni-Fabbroni (1996) Biochemistry 35:16361-16369; Olivas (1996) Nucleic Acids Res 24:1758-1764. Alternatively, antisense oligonucleotides that hybridize to the promoter sequence can be used to inhibit promoter activity.

For example, antisense polynucleotides of the invention can comprise an antisense sequence of at least 7 to 10 to about 20 or more nucleotides that specifically hybridize to a sequence complementary to the TERT promoter sequences of the invention. Alternatively, the antisense polynucleotide of the invention can be from about 10 to about 50 nucleotides in length or from about 14 to about 35 nucleotides in length. In other embodiments, they are less than about 100 nucleotides or less than about 200 nucleotides. In general, the antisense polynucleotide should be long enough to form a stable duplex (or triplex) but, if desired, short enough, depending on the mode of delivery, to be administered in vivo. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the nucleotides used in the antisense reagent (methylphosphonate backbone, peptide nucleic acid, phosphorothioate), among other factors. Methods relating to antisense polynucleotides, are also described in Antisense RNA And DNA, (1988), D. A. Melton, Ed., Cold Spring Harbor Laboratory, Cold Spring Harbor, N.Y.); Dagle (1991) Nucleic Acids Research 19:1805; Kim (1998) J. Controlled Release 53:175-182; for antisense therapy. Uhlmann (1990) Chem. Reviews 90:543-584; Poston (1998) J. Thorac. Cardiovasc. Surg. 116:386-396 (ex vivo gene therapy); Haller (1998) Kidney Int. 53:1550-1558; Nguyen (1998) Cancer Res 58:5673-7.

Identifying TERT Promoter Subsequences Bound by Transcriptional Regulatory Factors The invention provides means to identify and isolate trans-acting transcriptional regulatory factors that are involved in modulating the activity of the TERT promoter. Identification of cis-acting motifs by sequence identity comparison can be a useful initial means to identify promoter sequences bound by trans-acting factors. The hTERT promoter contains the motif known to bind to c-Myc (the "E-box" or "Myc/Max binding site"). Two SP1 binding sites are located starting at residue −168 and starting at residue −134. Other identified motifs include the sex determining region Y gene product (SRY), hepatic nuclear factor 3-beta (HNF-3β) and hepatic nuclear factor 5 (HNF-5), TFIID-MBP, E2F and c-Myb cis-acting transcriptional regulatory elements. To identify these motifs, a variety of comparison algorithms can be used. Karas (1996) Comput. Appl. Biosci. 12:441-6; Frech (1997) Pac Symp Biocomput. 7:151-62; Brzma (1998) Genome Res 8:1202-1215; Tsunoda (1998) Pac Symp Biocomput: 1998:252-63.

In addition to sequence identity analysis, TERT cis-acting transcriptional regulatory elements can be identified by functional assays, including promoter activity assays, DNase assays, binding assays (mobility shift assays), and oligonucleotide affinity column chromatography. After positive or tentative identification of a cis-acting binding site in a TERT promoter, these sequences are used to isolate the trans-acting transcriptional regulatory factor(s). In a preferred embodiment, the trans-acting factors are isolated using sequence-specific oligonucleotide affinity chromatography, the oligonucleotides comprising TERT sequences of the invention.

Another embodiment for identifying transcriptional regulatory motifs involves modifying putative cis-acting regulatory subsequences and assessing the change, if any, of the resultant TERT promoter to modulate transcription. The modification can be one or more residue deletions, residue substitutions, and chemical alterations of nucleotides. The (modified) promoter can be operably linked to TERT, a reporter gene, or any other transcribable sequence. The relative increase or decrease the modification has on transcriptional rates can be determined by measuring the ability of the unaltered TERT promoter to transcriptionally activate the reporter coding sequence under the same conditions as used to test the modified promoter. An increase or decrease in the ability of the modified TERT promoter to induce transcription as compared to the unmodified promoter construct identifies a cis-acting transcriptional regulatory sequence that is involved in the modulation of TERT promoter activity.

The reporter gene can encode a fluorescent or phosphorescent protein, or a protein possessing enzymatic activity. In alternative embodiments, the detectable protein is firefly luciferase, α-glucuronidase, α-galactosidase, chloramphenicol acetyl transferase, green fluorescent protein, enhanced green fluorescent protein, and the human secreted alkaline phosphatase. Another embodiment tests the ability of these cis-acting elements to bind soluble polypeptide trans-acting factors isolated from different cellular compartments, particularly trans-acting factors expressed in nuclei. For identification and isolation of factors that stimulate transcription, nuclear extracts from cells that express TERT are used.

Furthermore, once a cis-acting motif, or element, is identified, it can be used to identify and isolate trans-acting factors in a variety of cells and under different conditions (such as cell proliferation versus cell senescence). Accordingly, the invention provides a method for screening for trans-acting factors that modulate TERT promoter activity under a variety of conditions, developmental states, and cell types (including normal versus immortal versus malignant phenotypes). The cis-acting transcriptional regulatory sequences of the invention that modulate TERT promoter activity can also be used as oligonucleotides which, upon introduction into a cell, can bind trans-acting regulatory factors to modulate TERT transcription in vivo. This results in increased or decreased cell proliferative capacity for the treatment of various diseases and conditions.

High Throughput Screening of Small Molecule Modulators of TERT Transcription

The invention provides constructs and methods for screening modulators, in a preferred embodiment, small molecule modulators, of TERT promoter activity in vitro and in vivo. The invention incorporates all assays available to screen for small molecule modulators of TERT transcription. In a preferred embodiment, high throughput assays are adapted and used with the novel TERT promoter sequences and constructs provided by the invention. Schultz (1998) Bioorg Med Chem Lett 8:2409-2414; Weller (1997) Mol Divers. 3:61-70; Fernandes (1998) Curr Opin Chem Biol 2:597-603; Sittampalam (1997) Curr Opin Chem Biol 1:384-91.

In alternative embodiments, recombinant constructs contain hTERT promoter sequences driving a marker, such as an alkaline phosphatase marker gene (SEAP) or a §-galactosidase gene. Using a SEAP expressing construct of the invention, it was demonstrated that a TERT promoter fragment of approximately 2.5 kb is sufficient to activate and repress TERT transcription in response to proliferation and/or growth arrest stimuli in a model cell line, IDH4. Two cell clones, ID245-1 and ID245-16 whose SEAP profiles closely matched telomerase activity after TERT up-regulation by dexamethasone were selected and expanded for high throughput screening of small molecule activators of telomerase.

Treatment of Diseases Associated with Altered Telomerase Expression

The present invention provides TERT promoter sequences useful for the treatment of diseases and disease conditions. The recombinant and synthetic nucleic acids comprising TERT promoter, or TERT antisense complementary sequences, can be used to create or elevate telomerase activity in a cell, as well as to inhibit telomerase activity in cells in which it is not desired. In a preferred embodiment, human TERT promoter sequences or antisense sequences are used for the treatment of human diseases and disease conditions.

Identification of cis-acting transcriptional regulatory sequences by the invention further provides for the design of targeted sequences that, as oligonucleotides, can modify TERT promoter activity. In one embodiment, telomerase activity is created or elevated by binding significant amounts of a trans-acting transcriptional repressor or down-regulator with a nucleic acid that binds specifically to the repressor. In another embodiment, telomerase activity is down-regulated by antisense oligonucleotides binding to promoter sequences. Similarly, telomerase activity can be inhibited by binding significant amounts of a trans-acting transcriptional activator or up-regulator with a nucleic acid that binds specifically to the activator; or telomerase activity is up-regulated by antisense oligonucleotides binding to promoter sequences involved in telomerase repression. Thus, inhibiting, activating or otherwise altering a telomerase activity (telomerase catalytic activity, fidelity, processivity, telomere binding, etc.) in a cell can be used to change the proliferative capacity of the cell.

For example, reduction of telomerase activity in an immortal cell, such as a malignant tumor cell, can render the cell mortal. Conversely, increasing the telomerase activity in a cell line or a mortal cell (most human somatic cells) can increase the proliferative capacity of the cell. For example, expression of hTERT protein in dermal fibroblasts, thereby increasing telomere length, will result in increased fibroblast proliferative capacity. Such expression can slow or reverse age-related degenerative processes, such as the age-dependent slowing of wound closure (West (1994) Arch. Derm. 130:87). Thus, in one aspect, the present invention provides reagents and methods useful for treating diseases and conditions characterized by the presence, absence, or altered amount of human telomerase activity in a cell (where the diseases and conditions are susceptible to treatment using the compositions and methods disclosed herein). These diseases include, e.g. cancers, other diseases of cell proliferation (particularly, degenerative and aging processes and diseases of aging), immunological disorders, infertility (or fertility).

TERT Promoter Operably Linked to Cellular Toxins

In one embodiment, the TERT promoter of the invention is operably linked to a transcribable sequence that encodes a cellular toxin. Polypeptide toxins that can be recombinantly generated include ricin, abrin (Hughes (1996) Hum. Exp. Toxicol. 15:443-451), diphtheria, gelonin (Rosenblum (1996) Cancer Immunol. Immunother. 42:115-121), *Pseudomonas* exotoxin A, tumor necrosis factor alpha (TNF-α), *Crotalus durissus terrificus* toxin, *Crotalus adamenteus* toxin, *Naja naja* toxin, and *Naja mocambique* toxin. Rodriguez (1998) Prostate 34:259-269; Mauceri (1996) Cancer Res. 56:4311-4314. The cellular toxin can also be capable of inducing apoptosis, such as the ICE-family of cysteine proteases, the Bcl-2 family of proteins, bax, bclXs and caspases. Favrot (1998) Gene Ther. 5:728-739; McGill (1997) Front. Biosci. 2:D353-D379; McDonnell (1995) Semin. Cancer Biol. 6:53-60.

Alternatively, the sequence under the control of the TERT promoter can code for polypeptides having activity that is not itself toxic to a cell, but which renders the cell sensitive to an otherwise nontoxic drug, such as Herpes virus thymidine kinase (HSV-TK). The HSV-TK is innocuous but converts the anti-herpetic agent ganciclovir (GCV) to a toxic product that interferes with DNA replication in proliferating cells. Delaney (1996) J. Neurosci. 16:6908-6918; Heyman (1989) Proc. Natl. Acad. Sci. USA 86:2698-2702. The art describes numerous other suitable toxic or potentially toxic proteins and systems that may be applied in this embodiment.

The methods of the invention, in addition to enabling the specific killing of telomerase-positive cells, can also be used to prevent transformation of telomerase negative cells to a telomerase positive state. As shown in the examples below, an hTERT promoter sequence can be operably linked to a reporter gene such that activation of the promoter results in expression of the protein encoded by the reporter gene. If, instead of a reporter protein, the encoded protein is toxic to the cell, activation of the promoter leads to cell morbidity or death.

Oncolytic Viruses and Toxins for Treating Cancer

The present invention provides methods and compositions for reducing TERT promoter activity (and hence telomerase activity) in immortal cells and tumor cells for treating cancer. Cancer cells (malignant tumor cells) that express telomerase activity (telomerase-positive cells) can be mortalized by decreasing or inhibiting TERT promoter activity. Moreover, because measurable telomerase activity levels correlate with disease characteristics such as metastatic potential (U.S. Pat. Nos. 5,639,613; 5,648,215; 5,489,508; and Pandita (1996) Proc. Am. Ass. Cancer Res. 37:559), any reduction in TERT promoter activity could reduce the aggressive nature of a cancer to a more manageable disease state.

Taking advantage of this characteristic, in one embodiment of the invention, a TERT promoter sequence is operably linked to a gene encoding a toxin and introduced into a cell to kill the cell (such as ricin, diphtheria, gelonin, *Pseudomonas* toxin, abrin). If or when TERT transcriptional activators are expressed or activated in the cell, the toxin will be expressed, resulting in specific cell killing.

Alternatively, the TERT promoter-linked gene can encode a protein having activity that is not itself toxic to a cell, but which renders the cell sensitive to an otherwise nontoxic drug (such as Herpes virus thymidine kinase).

In another embodiment, the invention takes advantage of the fact that normal cytopathic viruses, in particular human cytopathic viruses, such as adenovirus or Herpes virus, require essential virally encoded genes to proliferate thereby lysing specific cells. Based on the description that follows, those skilled in the art will recognize that a number of different cytopathic viruses can be adapted according to this invention. Cytopathic viruses are well known in the art, and are described inter alia in publications by Coffey, Toda, Chase, and Kramm, infra. Genes essential for replication have been characterized in many such viruses. If an essential replication gene of any of these viruses is driven by the TERT promoter, proliferation of the virus and its cytopathic effects would be restricted to tumor cells and other telomerase expressing cells. For example, some essential genetic elements for replication of adenovirus are the E4, E1a, E1b, and E2 regions, or any of the late gene products. Essential genetic elements for replication of HSV-1 include ICP6 and ICP4.

Accordingly, the invention provides constructs and methods for killing telomerase positive cells (such as cancer cells) wherein TERT promoter sequences of the invention are operably linked to such essential replication genetic elements. For use in human cells, human cytopathic viruses modified with hTERT promoter sequences are preferred. Any one or more of the genes required for the replication and packaging of the virus could be modified to be driven by the TERT promoter. For instance, in one embodiment, expression of the E1a gene of adenovirus, which is required for the activation of expression of a cascade of adenoviral genes, is placed under the control of the hTERT promoter.

Thus, expression of E1a, and hence downstream replication of the virus, occurs only in those cells that express telomerase (such as tumor cells). Likewise, a recombinant adenovirus of the invention is designed so the adenoviral capsid genes are under the control of a TERT promoter. While this construct replicates its DNA in most cell types, it packages itself into active, infectious (and cytotoxic) virus only in those cells that express telomerase. Thus, when these constructs are used as cancer therapeutics, the conditionally replicative virus only infects and yields a productive infection in tumor cells (with no effect in "normal" cells that do not express telomerase). Infection of normal cells that do not express telomerase is expected to produce either no virus or abortive production of the virus, depending on which gene is driven by the TERT promoter. Thus, these recombinant viruses of the invention allow the natural, yet tumor specific, amplification of an oncolytic virus.

In alternative embodiments, many other elements are incorporated into a TERT promoter restricted oncolytic virus or a TERT promoter restricted replicative virus that is not lytic. Genes encoding suicide genes, marker genes, apoptotic genes or cell cycle regulators are incorporated in the TERT promoter restricted conditionally replicative recombinant virus. Expression of these elements in such a virus would assist the arrest of tumor growth. In one embodiment, elements to be included within these conditionally replicative viruses of the invention are structures that inhibit telomerase activity. These telomerase inhibitors could incorporate inhibitory oligonucleotides, dominant-negative inhibitors of TERT, or the gene for any agent that would disrupt or prevent TR/TERT assembly, interactions, or activity.

Other elements can also be included in the TERT promoter restricted vectors of the invention. For example, small inhibitory RNA molecules, preferably targeting cancer cells, such as RNA targeting telomerase activity can be synthesized in vivo using a recombinant adenovirus vector. Exemplary sequences are provided in U.S. Pat. No. 5,858,777 and GB 20890.4. RNA production from the adenovirus can be achieved by a variety of expression cassettes. For cell growth inhibition purposes, RNA polymerase III expression cassettes based on the structure of tRNA genes and other RNA polymerase III transcripts, including the U6 snRNA gene, as well as RNA polymerase II snRNP (U1, U2) transcripts are preferred due to their ability to produce high levels of transcripts.

The hTERT promoter restricted viruses of the invention can be designed to express inhibitory RNAs, as antisense molecules complementary to several regions of the hTR molecule, including the template region. The inhibitory RNAs can also mimic sequences and/or structures present in the RNA component of telomerase (e.g., hTR), including potential binding site(s) for TERT or other telomerase-associated proteins that might interact with the RNA component. Other elements can also be designed to generate inhibitory RNAs to target TERT mRNA by preventing its normal processing, folding, modification, transport and/or translation.

Other cytopathic viral vectors of the invention can be designed to generate RNA molecules with sequences necessary for cytoplasmic export and translation into peptides. The resulting polypeptides or peptides can be designed to target telomerase components or other molecules that are associated with telomerase thereby influencing telomerase catalytic activity. The peptides that inhibit telomerase will be produced at high level, paralleling the amount of RNA. For example, peptides could be designed to mimic the stretch of amino acids in hTERT involved in its binding to hTR, thereby acting as competitors in the assembly of a functional telomerase.

The TERT promoter restricted viral vectors of the invention can also be designed to generate peptides or polypeptides for any domain of TERT involved in interactions with other proteins and disrupt contacts that are essential for telomerase function. Other TERT promoter restricted viruses of the invention can be designed to generate polypeptides to bind to telomere complexes and prevent access and/or docking of telomerase or to generate immunogenic peptides, in part TERT peptides.

Other TERT promoter restricted viral vectors of the invention can be designed to generate polypeptides to mimic a variety of apoptosis inducing agents observed during programmed cell death and could result in the onset of apoptosis. TERT promoter restricted viruses do not necessarily need to be cytopathic. The TERT promoter conditionally restricted virus could be used to amplify any sequences or any element in any TERT expressing cell, such as a tumor cell.

Any of these embodiments can be provided with the conditionally replicative viruses of the invention. The TERT promoter constructs of the invention can also be used in gene therapy vectors to prevent telomerase activation and result in specific mortalization or death of telomerase-positive cells. Similarly, these gene therapy methods may be used for treating a genetic predilection for cancers.

Treatment of Other Conditions

The present invention also provides compositions and methods useful for treatment of diseases and disease conditions (in addition to cancers) characterized by under- or over-expression of telomerase or TERT gene products. Examples include diseases of cell proliferation, diseases resulting from cell senescence (particularly processes and diseases of aging), immunological disorders, infertility, and diseases of immune dysfunction. Certain diseases of aging are characterized by cell senescence-associated changes due to reduced telomere length (compared to younger cells), resulting from the absence (or much lower levels) of telomerase activity in the cell. Decreased telomere length and decreased replicative capacity contribute to these diseases. Telomerase activity (resulting in increased telomere length) can be up-regulated by increasing TERT promoter activity in the cell.

The present invention, by providing methods and compositions for modulating TERT promoter activity, also provides methods to treat infertility. Human germline cells (spermatogonia cells, their progenitors or descendants) are capable of indefinite proliferation and characterized by high telomerase activity. Abnormal or diminished levels of TERT gene products can result, in inadequate or abnormal production of spermatozoa, leading to infertility or disorders of reproduction. Accordingly, infertility associated with altered telomerase activity can be treated using the methods and compositions described herein to increase TERT promoter activity levels. Similarly, because inhibition of telomerase may negatively impact spermatogenesis, oogenesis, and sperm and egg viability, the compositions of the invention capable of inhibiting hTERT promoter activity can have contraceptive effects when used to reduce hTERT levels in germline cells.

In a further embodiment, the invention provides methods and composition useful for decreasing the proliferative potential of telomerase-positive cells such as activated lymphocytes and hematopoietic stem cells by reducing TERT promoter activity. Thus, the invention provides means for effecting immunosuppression. Conversely, the methods and reagents of the invention are useful in immunostimulation by increasing TERT promoter activity (resulting in increased proliferative potential) in immune cells, including hematopoietic stem cells (that express a low level of telomerase or no telomerase prior to therapeutic intervention).

Modulating TERT Promoter Activity

As is clear from the foregoing discussion, modulation of the level of TERT promoter transcriptional activity (and thus, the levels of telomerase or telomerase activity of a cell) can have a profound effect on the proliferative potential of the cell, and so has great utility in treatment of disease. This modulation can either be a decrease or an increase in TERT promoter activity. The promoter activity-modulatory nucleic acid molecules of the invention can act through a number of mechanisms. However, the invention is not limited to any particular mechanism of action.

For example, TERT promoter activity may be decreased or increased by single stranded antisense sequences that directly bind to TERT promoter sequences. This will result in decrease in affinity or inhibition of trans-acting transcriptional regulatory factors binding to critical TERT promoter sequences (TATA boxes, CAAT boxes, and the like). When the cis-acting element bound by a trans-acting factor has inhibitory activity, the binding of the oligonucleotide would result in up-regulation of TERT transcription. Conversely, if the promoter subsequence, when bound by a trans-acting factor, has up-regulating activity, the binding of the oligonucleotide would result in down-regulation of TERT transcription. In another embodiment, double-stranded oligonucleotides representing TERT promoter subsequences directly bind trans-acting transcriptional modulatory elements, thus preventing them from binding their corresponding cis-acting elements. In summary, TERT promoter activity may be increased or decreased through any of several mechanisms, or a combination of mechanisms. These include any means apparent to those of skill upon review of this disclosure.

The cis-acting transcriptional regulatory sequences of the invention can also be used as oligonucleotides which, upon introduction into a cell, can bind trans-acting regulatory factors to modulate TERT transcription in vivo. These oligonucleotides can be delivered to target cells through an appropriate delivery scheme or they can be synthesized in vivo by recombinant expression systems (vectors, viruses, and the like).

Oligonucleotides and Other Pharmaceutical Compositions

Antisense oligonucleotides which hybridize to TERT promoter sequences will inhibit the binding of trans-acting transcriptional regulatory agents to critical TERT promoter sequences. Furthermore, the result will be activation or repression of TERT transcriptional activity, depending on whether the promoter subsequence is down-regulatory or up-regulatory, respectively. Thus, the invention provides antisense oligonucleotides directed to the TERT promoter (cis-acting) binding sites for c-Myc (the "E-box" or "Myc/Max binding sites"), SP1, Y gene product (SRY), HNF-3β, HNF-5, TFIID-MBP, E2F, c-Myb, TATA boxes, CAAT boxes, and other regulatory elements.

TERT polynucleotides can be produced by direct chemical synthesis. Chemical synthesis will typically be used to produce oligonucleotides and polynucleotides containing nonstandard nucleotides (probes, primers and antisense oligonucleotides) although nucleic acids containing only standard nucleotides can also be prepared. Direct chemical synthesis of nucleic acids can be accomplished for example by the phosphotriester method of Narang (1979) Meth. Enzymol. 68:90; the phosphodiester method of Brown (1979) Meth. Enzymol. 68:109; the diethyl-phosphoramidite method of Beaucage (1981) Tetra. Lett. 22:1859; and the solid support method of U.S. Pat. No. 4,458,066. Chemical synthesis typically produces a single stranded oligonucleotide, which may be converted into double stranded DNA by hybridization with a complementary sequence, or by polymerization with a DNA polymerase and an oligonucleotide primer using the single strand as a template. One of skill will recognize that while chemical synthesis of DNA is often limited to sequences of less than about 100 or 150 bases, longer sequences may be obtained by the ligation of shorter sequences or by more elaborate synthetic methods. It will be appreciated that the polynucleotides and oligonucleotides of the invention can be made using nonstandard bases (other than adenine, cytidine, guanine, thymine, and uridine) or nonstandard backbone structures to provide desirable properties (increased nuclease-resistance, tighter binding, stability or a desired Tm). Techniques for rendering oligonucleotides nuclease-resistant include those described in PCT publication WO 94/12633. A wide variety of useful modified oligonucleotides may be produced, including oligonucleotides having a peptide nucleic acid (PNA) backbone (Nielsen (1991) Science 254:1497) or incorporating 2'-O-methyl ribonucleotides, phosphorothioate nucleotides, methyl phosphonate nucleotides, phosphotriester nucleotides, phosphorothioate nucleotides, and phosphoramidates. Still other useful oligonucleotides may contain alkyl and halogen-substituted sugar moieties comprising one of the following at the 2' position: OH, SH, $SCH_3$, F, OCN, $OCH_3OCH_3$, $OCH_3O(CH_2)nCH_3$, $O(CH_2)nNH_2$ or $O(CH_2)nCH_3$ where n is from 1 to about 10; C1 to C10 lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; amino-alkylamino; polyalkylamino; substituted silyl; an RNA cleaving group; a cholesteryl group; a folate group; a reporter group; an intercalator; a group for improving the pharmacokinetic properties of an oligonucleotide; or a group for improving the pharmacodynamic properties of an oligonucleotide and other substituents having similar properties. Folate, cholesterol or other groups which facilitate oligonucleotide uptake, such as lipid analogs, may be conjugated directly or via a linker at the 2' position of any nucleoside or at the 3' or 5' position of the 3'-terminal or 5'-terminal nucleoside, respectively. One or more such conjugates may be used. Oligonucleotides may also have sugar mimetics such as cyclobutyls in place of the pentofuranosyl group. Other embodiments may include at least one modified base form or "universal base" such as inosine, or inclusion of other nonstandard bases such as queosine and wybutosine as well as acetyl-, methyl-, thio- and similarly modified forms of adenine, cytidine, guanine, thymine, and uridine which are not as easily recognized by endogenous endonucleases. The invention further provides oligonucleotides having backbone analogues such as phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or $CH_2$—NH—O—$CH_2$, $CH_2$—N($CH_3$)—$OCH_2$, $CH_2$—O—N($CH_3$)-$CH_2$ and O—N($CH_3$)—$CH_2$—$CH_2$ backbones (where phosphodiester is O—P—O—$CH_2$), or mixtures of the same. Also useful are oligonucleotides having morpholino backbone structures (U.S. Pat. No. 5,034,506).

While the invention is not limited by any particular mechanism, oligonucleotides of the invention can also bind to double-stranded or duplex TERT promoter sequences. They can bind in a folded region, forming a triple helix, or "triplex" nucleic acid. Triple helix formation results in inhibition of TERT promoter activity by, disrupting the secondary structure of the promoter sequence, resulting in a new conformation which the trans-acting factor cannot bind with sufficient affinity to have a transcriptional-modifying effect. Alternatively, triple helix formation (induced by the binding of the antisense oligonucleotide of the invention) compromises the ability of the double helix to open sufficiently for the binding of polymerases, transcription factors, or regulatory trans-acting molecules to occur. Triplex oligonucleotide and polynucleotide construction is described in Cheng (1988) J. Biol. Chem. 263:15110; Ferrin (1991) Science 354:1494; Ramdas (1989) J. Biol. Chem. 264: 17395; Strobel (1991) Science 254:1639; Rigas (1986) Proc. Natl. Acad. Sci. U.S.A. 83: 9591) Carr, 1994, Molecular and Immunological Approaches, Futura Publishing Co, Mt Kisco N.Y.; Rininsland (1997) Proc. Natl. Acad. Sci. USA 94:5854; Perkins (1998) Biochemistry 37:11315-11322.

The therapeutic nucleic acids and methods of the invention involve the administration of oligonucleotides or polynucleotides that function to inhibit or stimulate TERT promoter activity under in vivo physiological conditions. In one embodiment, these nucleic acids are single stranded antisense sequences capable of binding to promoter sequences. In an alternative embodiment, they are double stranded nucleic acids capable of binding trans-acting transcriptional regulatory factors. They should be sufficiently stable under physiological conditions for a period of time to obtain a therapeutic effect. Modified nucleic acids can be useful in imparting such stability, as well as for targeting delivery of the oligonucleotide to the desired tissue, organ, or cell. Oligo- and poly-nucleotides can be delivered directly as a drug in a suitable pharmaceutical formulation, or indirectly by means of introducing a nucleic acid expression system that can recombinantly generate the hTERT promoter modulating oligonucleotides into a cell. In one embodiment, oligonucleotides directly bind to cis-acting sequences or, alternatively, bind to trans-acting regulatory factors. One embodiment exploits the fact that the TERT promoter is only relatively active in a very limited range of cell types, including, significantly, cancer cells.

Oligonucleotides or expression vectors can be administered by liposomes, immunoliposomes, ballistics, direct uptake into cells, and the like. For treatment of disease the oligonucleotides of the invention are administered to a patient in a therapeutically effective amount, which is an amount sufficient to ameliorate the symptoms of the disease or modulate hTERT promoter activity (thereby affecting telomerase activity) in the target cell. Methods useful for delivery of oligonucleotides for therapeutic purposes are described in U.S. Pat. No. 5,272,065. Telomerase activity can be measured by TRAP assay or other suitable assay of telomerase biological function, as discussed in detail in other publications.

The invention provides pharmaceutical compositions that comprise TERT promoter-containing nucleic acids (polynucleotides, expression vectors, gene therapy constructs) alone or in combination with at least one other agent, such as a stabilizing compound, diluent, carrier, cell targeting agent, or another active ingredient or agent. The therapeutic agents of the invention may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipients, adjuvants, and/or pharmaceutically acceptable carriers.

The pharmaceutical compositions of the invention can be administered by any means. Methods of parenteral delivery include topical, intra-arterial, intramuscular (IM), subcutaneous (SC), intramedullary, intrathecal, intraventricular, intravenous (IV), intraperitoneal (IP), or intranasal administration. Further details on techniques for formulation and administration may be found in the latest edition of Remington's Pharmaceutical Sciences (Maack Publishing Co, Easton Pa.); PCT publication WO 93/23572.

Pharmaceutical compositions of the invention include TERT-containing nucleic acids in an effective amount to achieve the intended purpose. "Therapeutically effective amount" or "pharmacologically effective amount" are well recognized phrases and refer to that amount of an agent effective to produce the intended pharmacological result. For example, a therapeutically effective amount is an amount sufficient to treat a disease or condition or ameliorate the symptoms of the disease being treated. Useful assays to ascertain an effective amount for a given application includes measuring the effect on endogenous TERT promoter activity and telomerase activity in a target cell. The amount actually administered will be dependent upon the individual to which treatment is to be applied, and will preferably be an optimized amount such that the desired effect is achieved without significant side effects. The therapeutically effective dose can be estimated initially either in cell culture assays or in any appropriate animal model. The animal model is also used to estimate appropriate dosage ranges and routes of administration in humans. Thus, the determination of a therapeutically effective dose is well within the capability of those skilled in the art.

Cells Lines and Animals with Modified Promoter Sequences

Most vertebrate cells senesce after a finite number of divisions in culture (~50 to 100 divisions). Certain variant cells, however, are able to divide indefinitely in culture (e.g., HeLa cells, 293 cells) and, for this reason, are useful for research and industrial applications. Usually these immortal cell lines are derived from spontaneously arising tumors, or by transformation by exposure to an oncogene, radiation or a tumor-inducing virus or chemical. Unfortunately, a limited selection of cell lines, especially human cell lines representing differentiated cell function, is available. Moreover, many immortal cell lines presently available are characterized by chromosomal abnormalities (aneuploidy, gene rearrangements, or mutations). Further, many long-established cell lines are relatively undifferentiated. Thus, there is a need for the TERT promoter activating compositions and methods of the invention to generate new immortal cell lines, especially using cells of human origin, where hTERT promoter activating compositions and methods are preferred.

The "immortalized cells" of the invention are not limited to those that proliferate indefinitely, but also include cells with increased proliferative capacity compared to similar cells whose TERT promoter has not been up-regulated. Depending on the cell type, increased proliferative capacity may mean proliferation for at least about 50, about 100, about 150, about 200, or about 400 or more generations, or for at least about 3, about 6, about 12, about 18, about 24 or about 36 or more months in culture.

Uses for cells with increased proliferative capacity include the production of natural proteins and recombinant proteins (therapeutic polypeptides such as erythropoietin, human growth hormone, insulin, and the like), or antibodies, for which a stable, genetically normal cell line is preferred. Another use is for replacement of diseased or damaged cells or tissue. For example, autologous immune cells immortalized using an TERT promoter sequence of the invention can be used for cell replacement in a patient after aggressive cancer therapy, such as whole body irradiation. Another use for immortalized cells is for ex vivo production of "artificial" tissues or organs for therapeutic use. Another use for such cells is for screening or validation of drugs, such as telomerase-inhibiting drugs, or for use in production of vaccines or biological reagents. Additional uses of the cells of the invention will be apparent to those of skill.

The invention also provides non-human transgenic animals comprising heterologous TERT or recombinant constructs comprising endogenous TERT promoter. In a preferred embodiment, the transgenic animals of the invention comprise a TERT promoter driving a heterologous gene, such as a reporter gene coding sequence. In a preferred embodiment, an hTERT promoter of the invention is operably linked to a reporter gene in a transgenic mouse. Alternatively, an mTERT promoter is operably linked to a reporter gene in a transgenic mouse. These transgenic animals are very useful as in vivo animal models to screen for modulators of TERT transcriptional activity. The introduction of hTERT, mTERT or other TERT promoters into animals to generate transgenic models is also used to assess the consequences of mutations or deletions to the transcriptional regulatory regions.

In one embodiment, the endogenous TERT gene in these mice is still functional and wild-type (native) telomerase activity can still exist. A TERT promoter of the invention is used to drive a high level expression of an exogenous TERT construct, the endogenously produced mTERT protein can be competitively replaced with the introduced, exogenous TERT protein. This transgenic animal (retaining a functional endogenous telomerase activity) is preferred in situations where it is desirable to retain "normal," endogenous telomerase function and telomere structure. In other situations, where it is desirable that all telomerase activity is by the introduced exogenous TERT protein, a mTERT knockout line can be used Promoter function, and in a preferred embodiment, hTERT promoter function, can be assessed with these transgenic animals. Alterations of TERT promoters can be constructed that drive TERT or a reporter gene to assess their function and expression pattern and characteristics (the invention also provides constructs and animals and methods for gene expression driven by a TERT promoter by transient transfection).

In one embodiment, the TERT promoters and reagents of the invention are used to create mouse cells and transgenic animals in which the endogenous TERT promoter is deleted, modified, supplemented or inhibited. For example, TERT promoter sequences can be deleted, modified or inhibited on either one or both alleles. The cells or animals can be reconstituted with a wild-type or modified TERT promoter, or, in a preferred embodiment, an exogenous TERT in the form of hTERT.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene/promoter to be suppressed. To prevent expression of endogenous promoter, simple mutations that alter or disrupt the promoter can be suitable. To up-regulate expression, a native TERT promoter can be substituted with a heterologous or mutated TERT promoter that induces higher levels of transcription, or with multiple copies of transgene TERT promoters. Also, "gene trap insertion" can be used to disrupt a host gene, and mouse embryonic stem (ES) cells can be used to produce knockout transgenic animals, as described herein and in Holzschu (1997) Transgenic Res 6: 97-106.

Vectors specifically designed for integration by homologous recombination comprising TERT promoter sequences are also provided by the invention. Important factors for optimizing homologous recombination include the degree of sequence identity and length of homology to chromosomal sequences. The specific sequence mediating homologous recombination is also important, because integration occurs much more easily in transcriptionally active DNA. Methods and materials for constructing homologous targeting constructs are described by Mansour (1988) Nature 336: 348; Bradley (1992) Bio/Technology 10:534; U.S. Pat. Nos. 5,627,059; 5,487,992; 5,631,153; and 5,464,764.

In a preferred embodiment, cell and transgenic animal models express TERT promoter (particularly, hTERT promoter) operably linked to a reporter gene. The cell or animal can be a TERT promoter "knockout" or it can retain endogenous TERT promoter activity. The insertion of the TERT promoter-containing exogenous sequence is typically by homologous recombination between complementary nucleic acid sequences. Thus, the exogenous sequence, which is typically an hTERT or mTERT promoter of this invention, is some portion of the target gene to be modified, such as exon, intron or transcriptional regulatory sequences, or any genomic sequence which is able to affect the level of the target gene's expression; or a combination thereof. The construct can also be introduced into other locations in the genome. Gene targeting via homologous recombination in pluripotential embryonic stem cells allows one to modify precisely the genomic sequence of interest.

In another embodiment, the introduced TERT promoter sequence (modified or wild type) can replace or disrupt an endogenous TERT promoter sequence. A newly introduced TERT promoter sequence can be engineered to have greater or lesser transcriptional activity, be responsive to new trans-acting transcriptional modulating agents, and the like.

Disruption of an endogenous TERT promoter sequence typically will decrease or abrogate ("knockout") the transcription of TERT. In one embodiment, the TERT promoter "knockout" is prepared by deletion or disruption by homologous recombination of the endogenous hTERT promoter. Homologous recombination and other means to alter (and "knockout") expression of endogenous sequences is described in Moynahan (1996) Hum. Mol. Genet. 5:875; Moynahan (1996) Hum. Mol. Genet. 5:875; Baudin (1993) Nucl. Acids Res. 21:3329; Wach (1994) Yeast 10:1793; Rothstein (1991) Methods Enzymol. 194:281; Anderson (1995) Methods Cell Biol. 48:31; Pettitt (1996) Development 122:4149-4157; Ramirez-Solis (1993) Methods Enzymol. 225:855; Thomas (1987) Cell 51:503; Couldrey (1998) Dev. Dyn. 212:284-292). Holzschu (1997) Transgenic Res 6:97-106; U.S. Pat. Nos. 5,464,764; 5,631,153; 5,487,992; 5,627,059, and 5,272,071; WO 91/09955; WO 93/09222; WO 96/29411; WO 95/31560; WO 91/12650. Vectors useful in TERT gene therapy can be viral or nonviral. They may comprise other regulatory or processing sequences. Lyddiatt (1998) Curr Opin Biotechnol 9:177-85.

The invention provides for delivery of the expression systems into cells or tissues in vitro or ex vivo. For ex vivo therapy, vectors may be introduced into cells taken from the patient and clonally propagated for autologous transplant back into the same patient (U.S. Pat. Nos. 5,399,493 and 5,437,994. Cells that can be targeted for TERT promoter gene therapy aimed at increasing the telomerase activity of a target cell include, but are not limited to, embryonic stem or germ cells, particularly primate or human cells, hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

The exogenous sequence is typically inserted in a construct, usually also with a marker gene to aid in the detection of the knockout construct and/or a selection gene. The knockout construct is inserted in a cell, typically an embryonic stem (ES) cell, usually by homologous recombination. The resultant transformed cell can be a single gene knockout (one haplotype) or a double gene (homozygous) knockout. The knockout construct can be integrated into one or several locations in the cell's genome due to the random nature of homologous recombination events; however, the recombination does occur between regions of sequence complementarity. Typically, less than one to five percent of the ES cells that take up the knockout construct will actually integrate exogenous DNA in these regions of complementarity; thus, identification and selection of cells with the desired phenotype is usually necessary and a selection or marker sequence is usually incorporated into the construct for this purpose. Cells which have incorporated the construct are selected for prior to inserting the genetically manipulated cell into a developing embryo; for example, the cells are subjected to positive selection (using G418, for example, to select for neomycin-resistance) and negative selection (using, for example, FIAU to exclude cells lacking thymidine kinase). Selection and marker techniques include antibiotic resistance selection or β-galactosidase marker expression as described elsewhere in this disclosure.

After selection of manipulated cells with the desired phenotype, such as complete or partial inability to express endogenous TERT promoter, or, expression of the exogenous TERT promoter (as hTERT promoter activity) the cells are inserted into a mouse embryo. Insertion can be accomplished by a variety of techniques, such as microinjection, in which about 10 to 30 cells are collected into a micropipet and injected into embryos that are at the proper stage of development to integrate the ES cell into the developing embryonic blastocyst, at about the eight cell stage, which for mice is about 3.5 days after fertilization. The embryos are obtained by perfusing the uterus of pregnant females. After the ES cell has been introduced into the embryo, it is implanted into the uterus of a pseudopregnant foster mother, which is typically prepared by mating with vascectomized males of the same species. In mice, the optimal time to implant is about two to three days pseudopregnant. Offspring are screened for integration of the TERT nucleic acid sequences and the modified promoter activity phenotype. Offspring that have the desired phenotype are crossed to each other to generate a homozygous knockout. If it is unclear whether germline cells of the offspring have modified promoter, they can be crossed with a parental or other strain and the offspring screened for heterozygosity of the desired trait. The heterozygotes can be crossed with each other to produce mice homozygous for modified TERT genomic sequence. Bijvoet (1998) Hum. Mol. Genet. 7:53-62; Moreadith (1997) J. Mol. Med. 75:208-216; Tojo (1995) Cytotechnology 19:161-165; Mudgett (1995) Methods Mol. Biol. 48:167-184; Longo (1997) Transgenic Res. 6:321-328; U.S. Pat. No. 5,616,491 (Mak, et al.); U.S. Pat. Nos. 5,464,764; 5,631,153; 5,487, 992; 5,627,059; 5,272,071; and, WO 91/09955, WO 93/09222, WO 96/29411, WO 95/31560, and WO 91/12650. Thus, the invention provides for the use of the TERT promoter sequence-containing reagents of the invention to produce "knockout" mouse cells and animals, transgenic animals, and their progeny. These cells and animals can be further reconstituted with wild type or modified endogenous mTERT promoter or exogenous TERT promoter, such as hTERT.

The present invention further provides methods and reagents for karyotype analysis, gene amplification detection, or other chromosomal analysis using probes comprising the TERT promoter sequences of the invention. In various embodiments, amplifications (change in copy number), deletions, insertions, substitutions, or changes in the chromosomal location (translocations) of TERT promoter containing genes are detected. These can be correlated with the presence of a pathological condition or a predisposition to developing a pathological condition (such as cancer). Thus, this information can be used in a diagnostic or prognostic manner. For instance, a translocation event could indicate that activation of TERT expression occurs in some cases by replacing all or part of the TERT promoter with another promoter element that directs TERT transcription in an inappropriate manner. Furthermore, the methods and reagents of the invention can be used to inhibit this inappropriate TERT activation.

Determining the chromosomal location of TERT promoter sequence may also be useful for analysis of TERT gene repression in normal somatic cells, for instance, whether the location is part of non-expressing heterochromatin. Nuclease hypersensitivity assays for distinguishing heterochromatin and euchromatin are described in Wu (1979) Cell 16:797; Groudine (1982) Cell 30:131; Gross (1988) Ann. Rev. Biochem. 57:159. Methods for analyzing karyotype are discussed in Pinkel (1988) Proc. Natl. Acad. Sci. USA 85:9138; EPO Pub. No. 430,402; Choo, ed., Methods In Molecular Biology Vol. 33: In Situ Hybridization Protocols, Humana Press, Totowa, N.J., 1994; Kallioniemi (1992) Science 258:818).

TERT Promoter Binding Proteins and Transcriptional Regulatory Factors

In addition to the novel TERT promoter sequences and identification of the cis-acting transcriptional regulatory sequences contained therein, the invention provides for novel in vitro and cell-based in vivo assay systems to screen for TERT promoter binding proteins (trans-acting transcriptional regulatory factors) using the nucleic acids of the invention. Many assays are available that screen for nucleic acid binding proteins and all can be adapted and used with the novel TERT sequences provided by the invention.

One embodiment of the invention provides a method of screening and isolating a TERT promoter binding compound by contacting a TERT promoter sequence of the invention (particularly, an identified cis-acting regulatory sequence) with a test compound and measuring the ability of the test compound to bind the selected nucleic acid. The test compound, can be any agent capable of specifically binding to a TERT promoter activity, including compounds available in combinatorial libraries, a cell extract, a nuclear extract, a protein or peptide. If a TERT transcriptional activating protein is the goal of the search, a cell with telomerase activity is typically chosen.

Various techniques can be used to identify polypeptides which specifically bind to TERT promoter; for example, mobility shift DNA-binding assays, methylation and uracil interference assays, DNase and hydroxyl radical footprinting analysis, fluorescence polarization, and UV crosslinking or chemical cross-linkers. For a general overview, see Ausubel (chapter 12, DNA-Protein Interactions). One technique for isolating co-associating proteins, including nucleic acid and DNA/RNA binding proteins, includes use of UV crosslinking or chemical cross-linkers, including cleavable cross-linkers dithiobis (succinimidylpropionate) and 3,3'-dithiobis (sulfosuccinimidyl-propionate). McLaughlin (1996) Am. J. Hum. Genet. 59:561-569; Tang (1996) Biochemistry 35:8216-8225; Lingner (1996) Proc. Natl. Acad. Sci. USA 93:10712; Chodosh (1986) Mol. Cell. Biol 6:4723-4733. In many cases, there is a high likelihood that a specific protein (or a related protein) may bind to an hTERT promoter sequence, such as a Myc, NF-kappa B, EF2, Sp1, AP-1 or CAAT box binding site. In these scenarios, where an antibody may already be available or one can be easily generated, co-immunoprecipitation analysis can be used to identify and isolate TERT promoter-binding, trans-acting factors. The trans-acting factor can be characterized by peptide sequence analysis. Once identified, the function of the protein can be confirmed, for example, by competition experiments, factor depletion experiments using an antibody specific for the factor, or by competition with a mutant factor.

Alternatively, TERT promoter-affinity columns can be generated to screen for potential TERT binding proteins. In a variation of this assay, TERT promoter subsequences are biotinylated, reacted with a solution suspected of containing a binding protein, and then reacted with a strepavidin affinity column to isolate the nucleic acid or binding protein complex (Grabowski (1986) Science 233:1294-1299; Chodosh (1986) supra). The promoter-binding protein can then be conventionally eluted and isolated. Mobility shift DNA-protein binding assay using no denaturing polyacrylamide gel electrophoresis (PAGE) is an extremely rapid and sensitive method for detecting specific polypeptide binding to DNA (Chodosh (1986) supra, Carthew (1985) Cell 43:439-448; Trejo (1997). J. Biol. Chem. 272:27411-27421; Bayliss (1997) Nucleic Acids Res. 25:3984-3990).

Interference assays and DNase and hydroxyl radical footprinting can be used to identify specific residues in the nucleic acid protein-binding site. Bi (1997) J. Biol. Chem. 272:26562-26572; Karaoglu (1991) Nucleic Acids Res. 19:5293-5300. Fluorescence polarization is a powerful technique for characterizing macromolecular associations and can provide equilibrium determinations of protein-DNA and protein-protein interactions. This technique is particularly useful (and better suited than electrophoretic methods) to study low affinity protein-protein interactions. Lundblad (1996) Mol. Endocrinol. 10:607-612.

Proteins identified by these techniques can be further separated on the basis of their size, net surface charge, hydrophobicity and affinity for ligands. In addition, antibodies raised against such proteins can be conjugated to column matrices and the proteins immunopurified according to well known methods. Scopes, R. K., Protein Purification: Principles and Practice, 2nd ed., Springer Verlag, (1987).

Transcriptional regulatory sequences identified by comparison of hTERT and mTERT sequences include the for trans-acting factors c-Myc, SP1, SRY, HNF-3β, HNF-5, TFIID-MBP, E2F and c-Myb. Table 1 shows other transcriptional regulatory sequences that have been identified upstream from the TERT encoding region by comparison of the hTERT sequence with known regulatory motifs. These elements are of interest in regulating transcription in the cell types where the factors that bind to these elements are present.

TABLE 1

Putative Recognition Elements Upstream from the hTERT Encoding Region

| Site Name | Position (relative to translation start) | FLANKING-RECOGNITION SEQUENCE-FLANKING (embedded in SEQ. ID NO: 1) |
|---|---|---|
| AP-2 CS5/Rev | -2995 | GGGCA-GGGCAGGC-ACGAG |
| HiNF-A RS | -2975 | ATTTT-ATTTAGCTATTT-TATTT |
| EcR-consensus (2) | -2889 | TCTTG-GCTCACTGCAA-CCTCC |
| Sp1-IE-3.1 | -2719 | GTGAT-CCGCCC-ACCTC |
| ApoE B1 | -2717 | GATCC-GCCCACCTC-AGCCT |
| HiNF-A RS | -2659 | GGCCT-ATTTAACCATTT-TAAAA |
| EcR-consensus (2) | -2598 | ATGGA-GTTCAATTTCC-CCTTT |
| AP-1 CS3/Rev | -2584 | CCCCT-TTACTCA-GGAGT |
| C/EBP CS1 | -2555 | ATATT-TTCTGTAAT-TCTTC |
| E2A CS | -2462 | CAGGG-GCAGCTG-GGAGG |
| Yi-consensus | -2316 | TCCAT-CCCTCCTACT-CTACT |
| C/EBP CS2 | -2313 | ATCCC-TCCTACTC-TACTG |
| EcR-consensus (2)/Rev | -2302 | TCTAC-TGGGATTGAGC-CCCTT |
| AP-2 CS4 | -2278 | TATCC-CCCCCAGGG-GCAGA |
| AP-2 CS4 | -2277 | ATCCC-CCCCAGGGG-CAGAG |
| PEA3 RS | -2241 | TGTGG-AGGAAG-GAATG |
| PEA3 CS | -2241 | TGTGG-AGGAAG-GAATG |
| Keratinocyte enhancer/Rev | -2178 | GTTGG-TTTGTTT-GTTTT |
| HNF-5 CS | -2176 | TGGTT-TGTTTGT-TTTGT |
| Keratinocyte enhancer/Rev | -2174 | GTTTG-TTTGTTT-TGTTT |
| Keratinocyte enhancer/Rev | -2169 | TTTGT-TTTGTTT-TGAGA |
| C/EBP CS1/Rey | -2103 | CTTGG-CTTACTGCA-GCCTC |
| INF.1 | -2075 | GGTTC-AAGTGA-TTCTC |
| GCN4 CS2 | -2074 | GTTCA-AGTGATTCTC-CTGCT |
| Sp1-IE-4/5 | -2028 | AGGCA-CCCGCC-ACCAT |
| AP-2 CS4/Rev | -1983 | AGACG-GGGGTGGGG-TGGGG |
| AP-2 CS5/Rev | -1957 | ATGTT-GGCCAGGC-TGGTC |
| E2A CS | -1888 | GGATT-ACAGGTG-TGAGC |
| PEA3 RS | -1824 | GAGGT-AGGAAG-CTCAC |
| PEA3 CS | -1824 | GAGGT-AGGAAG-CTCAC |
| NFI-NFI | -1788 | TTTTA-AGCCAAT-GATAG |
| CTF/NF-1a | -1788 | TTTTA-AGCCAAT-GATAG |
| CTF/NF-1b | -1788 | TTTTA-AGCCAAT-GATAG |
| PEA1 RS | -1730 | TGTGA-TGACTAA-GACAT |
| AP-1 CS3 | -1730 | TGTGA-TGACTAA-GACAT |
| AP-1 CS4 | -1730 | TGTGA-TGACTAA-GACAT |
| PEA3-uPA/Rev | -1630 | AGGCG-TTTCCT-CGCCA |
| C/EBP CS1/Rev | -1605 | TGTTA-ATTACTCCA-GCATA |
| NF-E1 CS1 | -1594 | CCAGC-ATAATCTT-CTGCT |
| Sp1-IE-3.1 | -1474 | CCAAA-CCGCCC-CTTTG |
| HNF-5 site | -1442 | AATTC-ACAAACA-CAGCC |
| NFkB CS4 | -1404 | ACTAA-GGGGATTTC-TAGAA |
| SIF-consensus | -1384 | AGCGA-CCCGTA-ATCCT |
| AP-2 CS5 | -1319 | AGGGT-GCGAGGCC-TGTTC |
| PEA3-uPA/Rev | -1280 | AGCAA-TTTCCT-CCGGC |
| PEA3 CS | -1256 | AAAGT-AGGAAA-GGTTA |
| HNF-5 CS | -1215 | TTCAG-TGTTTGC-CGACC |
| HSTF CS2 | -1169 | GAGAC-CCAGAAGTTTCTCG-CCCCT |
| AP-2 CS5 | -970 | CCCGA-GGCTGCCC-TCCAC |
| Sp1 CS2 | -950 | TGTGC-GGGCGG-GATGT |
| SP1 CS3 | -950 | TGTGC-GGGCGG-GATGT |
| E1A-F CS | -946 | CGGGC-GGGATGT-GACCA |
| Sp1-IE-3.1 | -807 | CGGGA-CCGCCC-CGGTG |
| AP-1 CS3 | -794 | GTGGG-TGATTAA-CAGAT |
| AP-2 CS5 | -657 | GTCCC-GCGTGCCC-GTCCA |
| SIF-consensus | -652 | GCGTG-CCCGTC-CAGGG |
| AP-2 CS4 | -620 | GTTCG-TCCCCAGCCG-CGTCT |
| GCF-consensus/Rev | -552 | CCCGA-CGCCCCGCGT-CCGGA |
| AP-2 CS5 | -531 | CTGGA-GGCAGCCC-TGGGT |
| Sp1-NPY | -452 | CATGG-CCCCTCC-CTCGG |
| Yi-consensus | -435 | GTTAC-CCCACAGCCT-AGGCC |

TABLE 1-continued

Putative Recognition Elements Upstream from the hTERT Encoding Region

| Site Name | Position (relative to translation start) | FLANKING-RECOGNITION SEQUENCE-FLANKING (embedded in SEQ. ID NO: 1) |
|---|---|---|
| AP-2 CS4/Rev | -358 | GCGGC-GCGCGGGCGG-GGAAG |
| Sp1 CS2 | -354 | CGCGC-GGGCGG-GGAAG |
| SP1 CS3 | -354 | CGCGC-GGGCGG-GGAAG |
| Sp1-IE-3.1 | -323 | CGGGT-CCGCCC-GGAGC |
| E2A CS | -314 | CCGGA-GCAGCTG-CGCTG |
| AP-2 CS5/Rev | -298 | GTCGG-GGCCAGGC-CGGGC |
| AP-2 CS5 | -297 | TCGGG-GCCAGGCC-GGGCT |
| AP-2 CS5/Rev | -289 | AGGCC-GGGCTCCC-AGTGG |
| c-Myc binding site | -242 | CTTCC-CACGTG-GCGGA |
| AP-2 CS5/Rev | -217 | GACCC-GGGCACCC-GTCCT |
| SIF-consensus | -212 | GGGCA-CCCGTC-CTGCC |
| Sp1-ras1.1 | -188 | TTCCA-GCTCCGCCTC-CTCCG |
| GC-box (1)/Rev | -188 | TTCCA-GCTCCGCCTC-CTCCG |
| Sp1 CS1/Rev | -168 | CGCGG-ACCCCGCCCC-GTCCC |
| SP1-IE3/2/Rev | -168 | CGCGG-ACCCCGCCCC-GTCCC |
| GC-box (1)/Rev | -168 | CGCGG-ACCCCGCCCC-GTCCC |
| Sp1-junD | -166 | CGGAC-CCCGCCCC-GTCCC |
| Sp1-IE-3.1 | -165 | GGACC-CCGCCC-CGTCC |
| SIF-consensus | -161 | CCCGC-CCCGTC-CCGAC |
| Sp1-NPY | -151 | CCCGA-CCCCTCC-CGGGT |
| Sp1-NPY | -127 | CCAGC-CCCCTCC-GGGCC |
| Sp1-NPY | -108 | CCCAG-CCCCTCC-CCTTC |
| GCF-consensus/Rev | -88 | TCCGC-GGCCCGCCC-TCTCC |
| Yi-consensus | -85 | GCGGC-CCCGCCCTCT-CCTCG |
| Sp1-IE-3.1 | -84 | CGGCC-CCGCCC-TCTCC |
| c-Myc binding site | -34 | CTGCG-CACGTG-GGAAG |
| AP-2 CS5/Rev | -13 | GCCCC-GGCCACCC-CCGCG |

The examples and detailed elaboration provided in this disclosure are for illustrative purposes, and are not intended to limit the invention. Modifications can be made by those skilled in the art that are included within the spirit of this application and scope of the appended claims.

EXAMPLES

Example 1

Cloning of λGφ5 and Characterization of hTERT Genomic Sequences

The following example details the cloning of the human hTERT promoter.

A human genomic DNA library was screened by PCR and hybridization to identify a genomic clone containing hTERT RNA coding sequences. The library was a human fibroblast genomic library made using DNA from WI38 lung fibroblast cells (Stratagene, Cat # 946204). In this fibroblast library, partial Sau3AI fragments were ligated into the XhoI site of a commercial phage cloning vector, Lambda FIX®. Vector (Stratagene, San Diego, Calif.), with insert sizes ranging from approximately 9 kilobases (kb) to 22 kb.

The genomic library was divided into pools of 150,000 phage each. Each pool screened by nested PCR, with the outer primer pair TCP1.52 & TCP1.57; inner pair TCP1.49 & TCP1.50. These primer pairs span a putative intron in the genomic DNA of hTERT and ensured the PCR product was derived from a genomic source and not from contamination by the hTERT cDNA clone. Positive pools were further subdivided until a pool of 2000 phage was obtained. This pool was plated at low density and screened via hybridization with a DNA fragment encompassing a subset of hTERT cDNA, generated by restriction digest with SphI and EcoRV.

Two positive clones were isolated and rescreened via nested PCR. At rescreening, both clones were positive by PCR. One of the lambda phage clones (designated "Gphi5" or "λGφ5") was digested with NotI, revealing an insert size of approximately 20 kb. Subsequent mapping indicated the insert size was 15 kb and that phage λGφ5 contains approximately 13 kb of DNA upstream from the transcriptional start site (upstream from the cDNA sequence).

Figure 1:
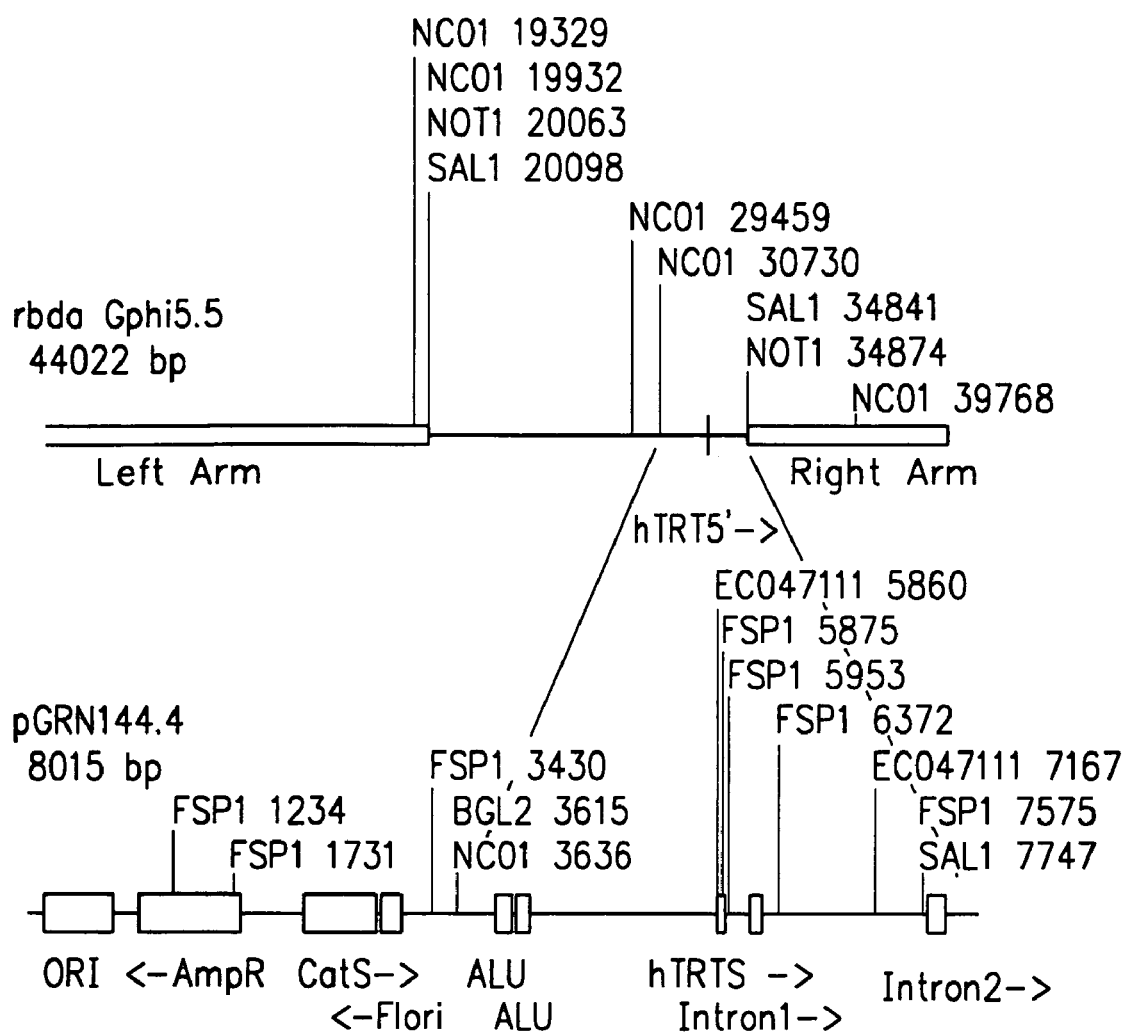
FIG. 1 is a restriction map of lambda phage clone λGφ5, used for obtaining the sequence about 15 kilobases upstream from the translation initiation site. This region includes the hTERT promoter.

FIG. 1 shows the structure of Phage λGφ5, mapped by restriction enzyme digestion and DNA sequencing.

Isolating, Subcloning and Sequencing the Genomic hTERT Insert

The phage DNA was digested with NcoI. This fragment was cloned into the plasmid pBBS167. The resulting subclones were screened by PCR to identify those containing sequences corresponding to the 5' region of the hTERT cDNA. A subclone (plasmid "pGRN140") containing a 9 kb NcoI fragment (with hTERT gene sequence and about 4 to 5 kb of lambda vector sequence) was partially sequenced to determine the orientation of the insert. pGRN140 was digested using SalI to remove lambda vector sequences, the resulting plasmid (with removed lambda sequences) designated pGRN144. The pGRN144 insert was then sequenced.

A NotI fragment from λGφ5 (containing the complete approximately 15 kbp genomic insert including the hTERT gene promoter region) was inserted in the NotI site of plasmid pBBS185. Two plasmids were isolated with their respective inserts oriented in opposite directions. One resulted in the insert oriented with the hTERT open reading frame (ORF) in the same orientation as the plasmid's Lac promoter, designated pGRN 142; the second, pGRN 143.

SEQ. ID NO:1 is a listing of the sequence data obtained from plasmid pGRN 142. Nucleotides 1-43 and 15376-15418 are plasmid sequence. Thus, the genomic insert begins at residue 44 and ends at residue 15375. The beginning of the cloned cDNA fragment corresponds to residue 13490. There are Alu sequence elements located≈1700 base pairs upstream. The sequence of the hTERT insert of pGRN 142 can now be obtained from GenBank (http://www.ncbi.nlm.nih.gov/) under Accession PGRN142.INS AF121948.

Numbering of hTERT residues for plasmids in the following examples begins from the translation initiation codon, according to standard practice in the field. The hTERT ATG codon (the translation initiation site) begins at residue 13545 of SEQ. ID NO:1. Thus, position −1, the first upstream residue, corresponds to nucleotide 13544 in SEQ. ID NO:1.

Example 2

TERT Promoter-Driven Reporter Constructs

This example describes the construction of plasmids in which reporter genes are operably linked to hTERT promoter sequences of the invention. This also illustrates how the TERT promoter sequence of the invention can analogously be operatively linked to heterologous sequences, such as polypeptide coding sequences, for expression in cells and tissues in vitro and in vivo and transgenic animals. As will be evident to one skilled in the art, techniques such as those illustrated in these examples can be used to test other candidate sequences for ability to specifically promote transcription in cells expressing TERT.

hTERT-linked reporter vectors of the invention have numerous uses, including identification of specific cis-acting sequences and trans-acting transcriptional regulatory factors. Importantly, these hTERT-containing reporter constructs can be used for the screening of agents capable of modulating (i.e., activating or inhibiting) hTERT transcription. These studies can be conducted in vitro and in vivo.

A number of reporter genes, such as firefly luciferase, β-glucuronidase, β-galactosidase, chloramphenicol acetyl transferase, and GFP are known and can be operably linked to hTERT promoter. In this example, the human secreted alkaline phosphatase (SEAP; ClonTech) was used. The SEAP reporter gene encodes a truncated form of the placental enzyme which lacks the membrane anchoring domain, thereby allowing the protein to be secreted efficiently from transfected cells. Levels of SEAP activity detected in the culture medium have been shown to be directly proportional to changes in intracellular concentrations of SEAP mRNA and protein. The chemiluminescence-based SEAP assay is about 10-fold more sensitive than similar assays using firefly luciferase as the reporter enzyme. The SEAP activity can also be assayed with a fluorescent substrate, which provides sensitivity comparable to luciferase. Berger (1988) Gene 66:1; Cullen (1992) Meth. Enzymol. 216:362; Yang (1997) Biotechniques 23:1110-1114.

hTERT 5' Upstream and Intron Sequences have "Promoter" Activity

Experiments with reporter constructs comprising various hTERT sequences of the invention identified cis-acting regions with "promoter" transcriptional activating activity in both 5' upstream and intron sequences. In brief, four constructs, pGRN148, pGRN150, "pSEAP2 basic" (no promoter sequences=negative control), and "pSEAP2 control" (contains the SV40 early promoter and enhancer) were constructed and transfected in triplicate into mortal and immortal cells.

Figure 2:
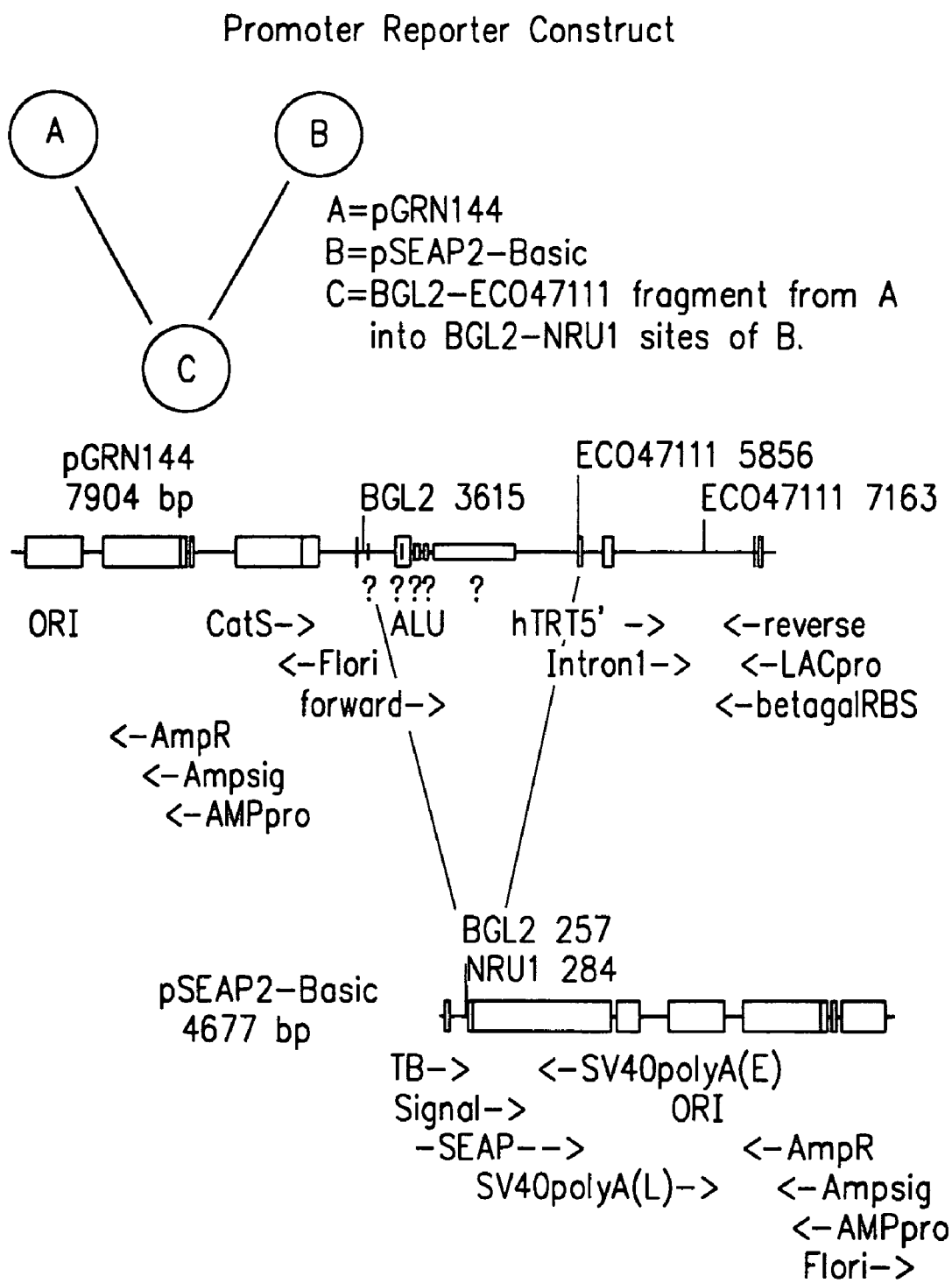
FIG. 2 is a map showing features of an hTERT promoter-reporter plasmid, Reporter plasmids have been used to demonstrate that the promoter specifically promotes transcription in cells expressing TERT, including cancer cells.

FIG. 2 shows the plan for construction of plasmid pGRN148. Briefly, a BgI2-Eco47III fragment from pGRN144 (described above) was digested and cloned into the BgIII-NruI site of pSeap2Basic (ClonTech, San Diego, Calif.). A second reporter-promoter, plasmid pGRN150 was made by inserting the BgIII-FspI fragment from pGRN144 into the BgIII-NruI sites of pSEAP2. Plasmid pGRN173 was constructed by using the EcoRV-StuI fragment from pGRN144. This makes a promoter reporter plasmid that contains the promoter region of hTERT from approximately 2.5 kb upstream from the start of the hTERT ORF to just after the first intron within the coding region. The initiating Met was mutated to Leu, so that the second ATG following the promoter region would be the initiating ATG of the SEAP ORF.

Use of the intron sequence allows identification of regulatory sequences that may be present in the intron (the invention provides transcriptional regulatory sequences from any portion of the hTERT genomic sequence). In addition to the hTERT derived pSEAP reporter constructs, a positive control vector and a negative control vector were used. The negative control (pSEAP2-Basic) is necessary to determine the background signal associated with the DNA backbone of the vector. A positive control is necessary to confirm transfection and expression of exogenous DNA and to verify the presence of active SEAP in the culture media. The positive control is the pSEAP2-Control vector (ClonTech) which contains the SEAP structural gene under transcriptional control of the SV40 promoter and enhancer.

Three constructs, the control, pGRN148 (which include hTERT 5' promoter sequences) and pGRN150, were transfected into a mortal cell line, BJ cells, a human foreskin fibroblast line, Feng (1995) Science 269:1236; and an immortal cell line, the human embryonic kidney line 293; Graham (1977) J. Gen. Virol. 36:59. All transfections were done in parallel with the two control plasmids.

In immortal cells, pGRN148 and pGRN150 constructs appear to drive SEAP expression as efficiently as the pSEAP2 positive control (containing the SV40 early promoter and enhancer). In contrast, in mortal cells only the pSEAP2 control gave detectable activity. Similar results were obtained using another normal cell line (RPE, or retinal pigmental epithelial cells; Aronson (1983) In vitro 19:642-650). In RPE cells transfected with pGRN150, the hTERT promoter region was inactive while the pSEAP2 control plasmid was active. These results indicate that, as expected, hTERT promoter sequences are active in tumor cells but not in mortal cells.

Identification of the Tissue Specificity Elements of the hTERT Promoter

The hTERT DNA promoter sequences were cloned into the pSEAP2-Basic transcription reporter vector (ClonTech) to generate the plasmids pGRN 148, 150, 175, 176, 181, 184, 261, 262, and 319. Summarized below are details of the promoter plasmid construction (nucleotide numbers refer to the number of nucleotides upstream of the translation initiation site at 13545 of SEQ ID NO:1):

pEGFP-1. *Vector from ClonTech containing the Enhanced Green Fluorescent Protein.

pGRN140. *NCO1 fragment containing hTERT upstream sequences and the first intron of hTERT from λGφ5 into the NCO1 site of a pBBS167 (variant of pUC19 cloning vector with MCS, e.g. ATGACCATGATTACGAATTC- GAGCTCGGTACCCGGGGATCCTCTA-GAGTCGACCTGCAGGCATGCC CATGGCAGGC-CTCGCGCGCGAGATCTCGGGCCCAATCGATGCCGC-GGCGATATCGCTCGAGGAAG CTTGGCACTGGCC (SEQ ID NO:3), and a chloramphenicol sensitive gene between the F1ori and the Amp gene in the opposite orientation from the Amp gene). The fragment is oriented so that the hTERT sequences are in the same direction as the Lac promoter.

pGRN144. described above; SalI deletion of pGRN140 to remove phage (lambda) sequences.

pGRN148: *BGL2-ECO47III fragment from pGRN144 containing hTERT upstream sequences (from position −51 to −2482) into the BGL2-NRU1 sites of pSEAP2-Basic to make a hTERT promoter/reporter plasmid.

pGRN150: *BGL2-FSP1 fragment from pGRN144 containing 2447 nt of hTERT upstream sequences (from position −36 to −2482) into the BGL2-NRU1 sites of pSEAP2 to make a hTERT promoter/reporter plasmid.

pGRN175: *APA1(Klenow blunt)-SRF1 religation of pGRN150 to delete most of the hTERT upstream sequences. This makes a promoter/reporter plasmid that uses 82 nucleotides of hTERT upstream sequences (from position −36 to −117).

pGRN176: *PML1-SRF1 religation of pGRN150 to delete most of the hTERT upstream sequences. This makes a promoter/reporter plasmid that uses 204 nucleotides of hTERT upstream sequences (from position −36 to −239).

pGRN181: *APA1 digestion and religation of pGRN150 to delete all APA1 sites but one. This makes a promoter/reporter plasmid that comprises from −36 to −114 and −1076 to −2482 of the hTERT upstream sequences.

pGRN184: *XBA1(partial, Klenow fill)-ECOR1 digest and religation of pGRN150 to make a deletion of the hTERT promoter sequences. This makes a promoter/reporter plasmid that expresses a region from −1391 to −2484 of the hTERT upstream sequences.

pGRN213. *FSP1 fragment containing the CatS gene and the F1 ORI plus part of the AmpR gene into the FSP1 sites of pSEAP2-Basic such that the orientation reconstructs the AmpR gene.

pGRN244: *SAL1-NOT1 fragment from pSEAP2-Basic containing the SEAP region into the SAL1-NOT1 sites of pEGFP-1. This modification adds a selectable marker to the vector.

pGRN245: *SAL1-NOT1 fragment from pGRN176 containing the hTERT-promoter/SEAP region into the SAL1-NOT1 sites of pEGFP-1. This modification adds a dominant selectable marker to the vector.

pGRN246: *SAL1-NOT1 fragment from pGRN176 containing the hTERT-promoter/SEAP region into the SAL1-NOT1 sites of pEGFP-1. This modification adds a dominant selectable marker to the vector.

pGRN248 *SAL1-NOT1 fragment from pGRN175 containing the hTERT promoter/SEAP region into the SalI-NotI sites of pEGFP-1. This modification adds a dominant selectable marker to the vector.

pGRN259. *in vitro mutagenesis using RA94 (CCCG-GCCACCCCGCGAattCGCGCGCTC CCCGCTGC) (SEQ ID NO:4) to introduce an EcoRI site at the initiating met of hTERT in pGRN144. This provides hTERT sequences from +1 to −2482 that can be cloned into a vector using EcoRI and BglII.

pGRN260. *in vitro mutagenesis using RA91 (TTG-TACTGAGAGTGCACCATATGCGGTGTG catgcTACG-TAAGAGGTTCCAACTTTCACCATAAT) (SEQ ID NO:5) to delete several sites from the Chloramphenicol region of pGRN213 to create a variant, more useful, MCS. This creates a Mutagenesis version of pSEAP2-Basic with more unique cloning sites in its MCS.

pGRN261: *BGL2-ECOR1 fragment from pGRN259 containing hTERT upstream sequences into the BGL2-ECOR1 sites of pSEAP2-Basic. This makes a promoter/reporter expression plasmid that contains from +1 to −2482 of the hTERT upstream sequences.

pGRN262: *BGL2-ECOR1 fragment from pGRN259 containing hTERT upstream sequences into the BGL2-ECOR1 sites of pGRN260. This makes a promoter/reporter expression and mutagenesis plasmid that contains from +1 to −2482 of the hTERT upstream sequences.

pGRN294. *BbsI-XhoI fragment from pGRN142 containing hTERT upstream sequences from −1667 to −3278 into the BbsI-XhoI sites of pGRN259. This makes a vector containing the genomic upstream region for hTERT from +1 to −3278 that can be cloned with EcoRI and XhoI.

pGRN295: *ECOR1-XHO1 fragment from pGRN294 containing from +1 to −3282 of hTERT upstream sequences into the ECOR1-XHO1 sites of pGRN260. This makes a SEAP promoter/reporter/mutagenesis plasmid.

pGRN296: *ECOR1-XHO1 fragment from pGRN294 containing from +1 to −3282 of the hTERT upstream sequences into the ECOR1-XHO1 sites of pSEAP2-Basic. This makes a SEAP promoter/reporter plasmid.

pGRN297. *RA96 (AATTGCGAAGCTTACG) (SEQ ID NO:6) and RA97 (AATTCGTA AGCTTCGC) (SEQ ID NO:7) annealed to make an oligo linker into the ECOR1 sites of pGRN259 replacing the ECOR1 fragment of the intron-exon region of pGRN259.

pGRN299: *XHO1-HIND3 fragment from pGRN298 containing from +1 to −3282 of the hTERT upstream sequences into the XHO1-HIND3 sites of pGL2-Basic. This makes a Luciferase promoter/reporter plasmid with about 3.3 Kb of hTERT promoter sequences.

pGRN300: *XHO1-SAC1 fragment from pGRN142 containing hTERT upstream sequences into the XHO1-SAC1 sites of pGRN299 such that the resulting construct contains from +1 to −5124 of the hTERT upstream sequences. This creates an hTERT promoter/reporter construct using Luciferase as a reporter.

pGRN310: *SAC1 fragment from pGRN142 containing hTERT upstream sequences into the SAC1 site of pGRN300 such that the resulting construct contains +1 to −7984 of the hTERT upstream sequences. This creates an hTERT promoter/reporter construct using Luciferase as a reporter.

pGRN311. *SPE1 fragment from pGRN142 containing from −4773 to −13501 of the hTERT upstream sequences into the SPE1 site of pGRN300 such that the orientation reconstructs the genomic region. This makes a Luciferase promoter reporter plasmid that contains the entire pGRN142 upstream genomic region of hTERT plus a 365 bp region of genomic DNA from the middle of the 13.5 Kb genomic region repeated upstream of the T7 promoter.

pGRN312: *BGL2-FSP1 fragment from pGRN144 into the BGL2-HIND3 (Klenow filled) sites of pGL2-Basic. This makes a Luciferase promoter/reporter version of pGRN150.

pGRN313: *KPN1-NOT1 digested pGRN311 blunted with T4 polymerase and religated. This makes a Luciferase promoter/reporter plasmid using from +1 to −13501 of the hTERT upstream sequences.

pGRN316: *oligo RA101 (5'- TAGGTACCGAGCTCT-TACGCGTGC TAGCCCCACGTGGCGGA GGGACTGGGGACCCGGGCA-3') (SEQ ID NO:8) used for in vitro mutagenesis to delete the genomic sequence from pGRN262 between the SRF1 site and the first PML1 site. This makes a promoter-reporter plasmid containing hTERT upstream sequences from +1 to −239.

pGRN317: *oligo RA100 (5'-TAGGTACCGAGCTCT-TACGCGTGCTAGCCCCTCGCTGG CGTCCCT GCAC-CCTGGGAGCGC-3') (SEQ ID NO:9) used for in vitro mutagenesis to delete the genomic sequence from pGRN262 between the SRF1 site and next to the last APA1 site. This makes a promoter-reporter plasmid containing hTERT upstream sequences from +1 to −397.

pGRN319: *RA107 (5'-CGTCCTGCTGCGCACtcaG-GAAGCCCTGGCCCC-3') (SEQ ID NO:10) used for in vitro mutagenesis to inactivate the 'B' class E-box just proximal to the hTERT initiating met in pGRN262. This changes the CACGTG (SEQ ID NO:11) to CACTCA (SEQ ID NO:12). Also COD1941 (5'-GATGAATGCTCATGAT-TCC (SEQ ID NO:13) was used to switch from CatR to CatS introducing a BSPH1 site and COD2866 (5'-CAG-CATCTTTTACTTTCACCAGCGTTTCTGGGTG CGCAAAA ACAGGAAGGCAAAATGCC-3') (SEQ ID NO:14) was used to select from AmpS to AmpR introducing an FSP1 site. In summary, pGRN319 carries a mutation in the E-box.

pGRN350: *RA104 (5'-TAGGTACCGAGCTCT-TACGCGTGCTAGCCCCTCCCAGCCCCTC CCCT TCCTTTCCGCGGC-3') (SEQ ID NO:15) used for in vitro mutagenesis to delete the genomic sequence from pGRN262 between the SRF1 site and the last APA1 site before the ATG of the hTERT open reading frame (orf). This makes a promoter-reporter plasmid containing hTERT upstream sequences from +1 to −117.

pGRN351: *SAC2 fragment from pGRN319 into the SAC2 sites of pGRN350 such that the SEAP orf is recreated. This makes a "deactivated E-box" version of pGRN350.

pGRN352: *RA122 (5'-GACCGCGCTTCCCACt-caGCGGAG GGACTGGGG-3') (SEQ ID NO:16) used for in vitro mutagenesis to "deactivate" the penultimate class "B" E-box before the translation start site of hTERT.

The pSEAP2-Basic plasmid lacks eukaryotic promoter and enhancer sequences. This vector contains the SV40 late polyadenylation signal inserted downstream of the SEAP coding sequences to ensure proper and efficient processing of the transcript in eukaryotic cells. It also contains a synthetic transcription blocker (TB), composed of adjacent polyadenylation and transcription pause sites to reduce background transcription. As noted above, the SEAP reporter gene encodes a truncated form of the placental enzyme which lacks the membrane anchoring domain, thereby allowing the protein to be efficiently secreted from transfected cells.

Levels of SEAP activity detected in the culture medium have been shown to be directly proportional to changes in intracellular concentrations of SEAP mRNA. The chemiluminescent SEAP substrate CSPD™ (ClonTech) was used to detect secreted SEAP. Use of this substrate enables monitoring of the expression of the SEAP reporter gene through simple, sensitive, non-radioactive assays of secreted phosphatase activity. This chemiluminescent assay can detect as little as 10-13 g of SEAP protein. The assay is linear over a 104 fold range of enzyme concentrations. This makes the assay (and these vectors) particularly well-suited for comparative analyses.

In addition to the hTERT derived pSEAP reporter constructs, a positive control vector (pSEAP2-Control vector) and a negative control vector (pSEAP2-Basic) were used. The promoter constructs (pGRN 150, 175, 176) and the control vectors were transfected into immortal (HEK 293) and mortal (BJ fibroblast, RPE, HUVEC) cells 48-72 hours after transfection. The culture media was collected and assayed for SEAP activity. The SEAP activity was detected using the chemiluminescent assay from CLONTECH, Great EscAPe™ SEAP Chemiluminescence Kit, according to the manufacturer's protocol. The transfections were performed in triplicate. The culture media from each transfection was collected after 48-72 hours and assayed in triplicate. The background values obtained by transfection of the negative control (pSEAP2-Basic) vector was subtracted from the values obtained with the test constructs. The average of nine measurements was used and plotted for each of the constructs.

Experimental Results in Immortal and Mortal Cell Lines

The results of the assays show that while the hTERT promoter constructs are capable of driving the expression of the reporter SEAP gene in immortal cells, the same constructs are silent in all mortal cells tested. The pSEAP2-Control vector however is active in all cell types regardless of their mortal or immortal status and the pSEAP2-Basic vector is silent in all cells assayed.

hTERT Promoter Driving Thymidine Kinase Expression In vitro

The invention provides constructs comprising heterologous coding sequences operably linked to hTERT promoter sequences. In one embodiment, hTERT coding sequences are operably linked to Herpes simplex virus thymidine kinase ("HSV-TK") coding sequences. HSV-TK is an enzyme that is capable of converting innocuous prodrugs, e.g. ganciclovir, into toxic metabolites that interfere with the cellular replication of proliferating cells (such as cancer cells, which have active hTERT promoter activity). Controlling thymidine kinase (TK) expression by subordinating it to the hTERT promoter restricts TK expression to cells where the hTERT promoter is normally active. This prevents TK expression in "normal" cells, where the hTERT promoter is usually silent.

The ability of the hTERT promoter to specifically drive the expression of the TK gene in tumor cells was tested using a variety of constructs: One construct, designated pGRN266, contains an EcoRI-FseI PCR fragment with the TK gene cloned into the EcoRI-FseI sites of pGRN263. pGRN263, containing approximately 2.5 kb of hTERT promoter sequence, is similar to pGRN150, but contains a neomycin gene as selection marker. pGRN267 contains an EcoRI-FseI PCR fragment with the TK gene cloned into the EcoRI-FseI sites of pGRN264. pGRN264, containing approximately 210 bp of hTERT promoter sequence, is similar to pGRN176, but contains a neomycin gene as selection marker. pGRN268 contains an EcoRI-XbaI PCR fragment with the TK gene cloned into the EcoRI-XbaI (unmethylated) sites of pGRN265. pGRN265, containing approximately 90 bp of hTERT promoter sequence, is similar to pGRN175, but contains a neomycin gene as selection marker.

These hTERT promoter/TK constructs, pGRN266, pGRN267 and pGRN268, were re-introduced into mammalian cells and TK/+ stable clones (and/or mass populations) were selected. Ganciclovir treatment in vitro of the TK/+ cells resulted in selective destruction of all tumor lines tested, including 143B, 293, HT1080, Bxpc-3, DAOY and NIH3T3. Significantly, ganciclovir treatment had no effect on normal BJ cells. This clearly demonstrates the tumor-specificity of all three hTERT promoter fragments used in these experiments.

Example 3

Direct In vivo hTERT Promoter Suicide Gene Therapy

The invention provides reagents and methods for treating diseases involving unwanted cell proliferation by in vivo gene therapy. To demonstrate the efficacy of this aspect of the invention, the reagents of the invention were used to treat cancer (of human origin) in an art-accepted animal model. A human cancer cell, the osteosarcoma cell line 143B, which normally expresses the telomerase gene, was transfected with a plasmid containing the TK gene driven by the hTERT promoter.

Specifically, sequences −36 to −2482 upstream of the translation start site of SEQ ID NO:1 were used to drive the TK gene. The plasmid also contained the neomycin phosphotransferase gene. After transfection of cells with the plasmid, G418 resistant clones expressing TK were selected. Two hundred thousand of the parental or TK expressing 143B cells were injected subcutaneously in the flank of Balb/c nude (nu/nu) mice to establish tumors. Four to 11 days after tumor implantation the mice were injected IP with 75 mg/kg ganciclovir (GCV) or saline twice daily. Tumor growth was monitored every 3-4 days. When GCV was administered either at 4 or at 11 days post tumor implantation to these tumor bearing animals, TK mediated cell lysis and retarded tumor growth was observed. Such inhibition of tumor cell growth is not observed when saline is administered or if the parental 143B tumor (143BP) is treated with either saline or GCV. Forty-five days after tumor implantation, only the animals implanted with the TK+ 143B clone and treated with GCV showed 100% survival. In the other groups all but one animal died from massive tumor burden.

These data indicate that the hTERT promoter is sufficient to drive TK gene expression both in vivo. It also shows that the reagents and methods of the invention can be used to promote tumor regression in vivo in subjects (including humans) carrying pre-established tumors.

Example 4

Oncolytic Viruses Under Control of the hTERT Promoter

As discussed earlier the invention provides "conditionally replicating" oncolytic virus constructs in which hTERT promoter sequences of the invention are operably linked to essential virally encoded genes. Use of hTERT promoter sequences of the invention ensures the virus will only be productively expressed in cells with telomerase activity. Thus, constructs can be used therapeutically to lyse only cells that express telomerase, such as immortal or cancer cells. Proliferation of the virus and its cytopathic effects is thus restricted to tumor cells. Details of the construction of an exemplary hTERT promoter driven, conditionally replicating oncolytic virus follows. In this embodiment, the hTERT promoter replaces the normal E1a promoter to create a virus which will only replicate in telomerase expressing cells.

Plasmid pBR/ITR/549-ClaI containing nucleotides 1-356 (Ad2 ITR and packaging signals) and 549-920 (a portion of the E1a coding sequence) of Adenovirus 2 (Ad2) linked using a polylinker was built using standard molecular biology procedures in the bacterial plasmid pBR322. In pBR/ITR/TB+phTERT176-E1A and pBR/ITR/TB+phTERT316-E1A, the normal E1a promoter (Ad2 357-548) has been replaced with the hTERT promoter. Ad2 sequences from 916-10680 are added to these plasmids to recreate the expression elements of the 5' end of the virus.

These plasmids (pBR/ITR/TB+phTERT176-10680 and pBR/ITR/TB+phTERT316-10680) are transfected into a telomerase expressing human cell line along with an adenoviral DNA fragment containing Ad2 sequences 10681-35937. Recombinant plaques are scored and selected 7-21 days post transduction. The hTERT promoter E1a containing Ad2 is propagated and produced for use employing standard schemes for recombinant Ad2 amplification and manufacturing. (Graham and Prevec, 1991, in Methods in Molecular Biology, Chapter 11, Ed E. J. Murray, The Human Press Inc., Clifton, N.J.; Kanegae et al., Jpn J Med Sci Biol, 1994, 47(3):157-66). Because the E1a gene is driven by the hTERT promoter, which is not normally expressed by most somatic cells, recombinant Ad2 genome will only replicate and be packaged into virus particles in cells expressing telomerase.

Example 5 hTERT Promoter Sequences Driving an Alkaline Phosphatase Reporter Gene for High Throughput Screening The invention provides constructs and promoter-based assays to identify small molecule activators and/or repressors of hTERT and telomerase activity. To this end, fragments of the hTERT promoter were cloned into plasmids expressing a secreted form of alkaline phosphatase and a selection marker. The SEAP constructs (pGRN244, pGRN245, pGRN246 and pGRN248) were re-introduced into normal human cells and into immortal cell lines. After selection of stable clones having integrated the hTERT promoter/SEAP constructs, RT-PCR was used to determine the levels of SEAP mRNAs. In 293 cells, the levels of SEAP mRNA were elevated and comparable to the levels of endogenous hTERT, whereas in BJ cells, the levels of SEAP mRNA were virtually undetectable and closely matched the levels of the endogenous hTERT in these cells.

These results indicate that hTERT promoter/SEAP constructs can be used to engineer cells suitable for promoter-based assays and to screen for chemical and/or biological activators and/or repressors of telomerase in normal and tumor cells. pGRN244, pGRN245, pGRN246 and pGRN248 were re-introduced into BJ and 293 cells. SEAP activity and mRNA levels were determined in these cells as criteria for clone selection. Several 293 and BJ lines were selected and two BJ/pGRN245 clones were expanded for high throughput screening. These constructs were also introduced into IDH4 cells, which are immortal lung fibroblasts that express the SV40 large T antigen under the control of the dexamethasone-inducible MMTV promoter. IDH4 cells are telomerase positive and proliferate in the presence of dexamethasone. However, these cells can be induced into a senescent, telomerase negative stage after dexamethasone removal. Upon re-addition of dexamethasone, the cells return to an immortal phenotype and re-activate telomerase.

pGRN244, pGRN245, pGRN246 and pGRN248 were transfected into IDH4 cells. SEAP activity was shown to parallel telomerase activity in the different clones, whereas no significant fluctuation of SEAP activity was observed with the control plasmid. These results indicate that a fragment of approximately 2.5 kb of hTERT promoter sequence (pGRN245) contains sufficient sequence elements to support both activation and repression in response to proliferation and/or growth arrest stimuli that control telomerase activity in IDH4 cells. Two clones, ID245-1 and ID245-16 whose SEAP profile closely matched telomerase activity during drug treatment, were selected and expanded for high throughput screening of small molecule activators of telomerase.

Example 6 hTERT Promoter Sequences Driving a β-galactosidase Reporter Gene to Identify Biological Regulators of hTERT and Telomerase Activity The invention also provides constructs and promoter-based assays to identify biological modulators of hTERT and telomerase activity. An exemplary construct of this aspect of the invention is pGRN353 containing a BglII-HindIII fragment from pGRN297 with approximately 2.5 kb of hTERT promoter sequences cloned into the BglII-HindIII sites of β-gal-Basic (ClonTech). pGRN353 or similar constructs are re-introduced into BJ cells by co-transfection with a plasmid containing a hygromycin gene as selection marker. Clonal cell lines and/or mass populations are established and used to screen retroviral based cDNA libraries for genes or fragments of genes that can activate the hTERT promoter. pGRN353 or similar constructs are also re-introduced into 143B and 293 cells to screen retroviral libraries to identify sequences that can repress the hTERT promoter.

Example 7

Identifying Trans-Acting Transcriptional Regulatory Elements

The promoter-reporter (and other) vectors of the invention are also used to identify trans-acting transcriptional regulatory elements. As noted supra, plasmids in which reporter genes are operably linked to hTERT promoter sequences are extremely useful for identification of trans-acting transcriptional modulatory agents and for the screening of potential hTERT promoter-modulating drugs (including biological agents and small molecules). Both transient and stable transfection techniques can be used. In one embodiment, stable transformants of pGRN148 are made in telomerase negative and telomerase positive cells by cotransfection with a eukaryotic selectable marker (such as neo), according to Ausubel, supra.

The resulting cell lines are used for screening of putative telomerase trans-acting transcriptional modulatory agents, for example, by comparing hTERT-promoter-driven expression in the presence and absence of the test compound (the putative trans-acting transcriptional modulating agent). Additional promoter-reporter vectors (including the constructs described herein, as variations thereof) are similarly used to identify and isolate trans-acting factors binding to cis-acting transcriptional regulatory elements, such as, Myc, Sp1, TATA box binding protein, AP-1, CREB, CAAT binding factor and factors binding to hormone response elements (e.g., GRE). The identification and isolation of such trans-acting regulatory sequences provide for further methods and reagents for modulating the transcription and translation of telomerase.

Example 8 c-Myc Acts as a Potent Activator of the TERT Promoter by Direct Interaction with Cis-Acting Regulatory Sequences Use of recombinant constructs comprising TERT promoter sequences of the invention has, for the first time, demonstrated that c-Myc acts as a potent activator of telomerase activity by direct interaction with cis-acting regulatory sequences in the TERT promoter. Significantly, the studies of the invention also show that transcriptional activation of the hTERT promoter by c-Myc can be abrogated by deletion or mutation of a single cis-acting regulatory sequence, the "Myc/Max binding site."

To determine whether experimental induction of c-Myc can lead to the de novo activation of telomerase in primary human cells, pre-senescent IMR90 cultures engineered to express the mouse ecotropic receptor (Serrano et al. (1997) Cell 88, 593-602) were transduced with either the pBABE retroviral vector or one encoding a hormone inducible c-Myc-Estrogen Receptor (cMycER) fusion protein (Eilers et al., 1989 Nature 340, 66-68; Littlewood (1995) Nucl. Acids Res. 23, 1686-1690). IMR90 cult do not possess detectable telomerase activity or TERT gene expression (Nakamura et al., 1997; Meyerson et al., 1997).

Retroviral Infection The mouse ecotropic receptor was transduced into IMR90 fibroblasts and all subsequent transductions with ecotropic retrovirus were carried out according to Serrano et al. (1997). pBABE-MycER and pBABE vector control viruses were harvested from stable expressing _2 cell lines.

Cell Culture: IMR90 cells were grown in Dulbecco's Modified Eagle Medium (DMEM) (Gibco/BRL) supplemented with 10% fetal bovine serum (FBS), 0.29 mg/mL L-glutamine, 0.03% penicillin and streptomycin, and 25 µg/mL gentamycin sulfate. For the Myc induction studies in IMR90 cells, MycER transduced cells were exposed to 2 µM 4-OHT for 24, 48 and 72 hours. For the promoter studies NIH 3T3 cells were exposed to 1 µM 4-OHT for 24 and 72 hours. In all cases uninduced controls were treated with an equivalent volume of ethanol, the solvent for 4-OHT.

Telomerase Assays: Telomerase activity was measured by a modified telomerase repeat amplification protocol using the TRAPeze™ telomerase detection kit (Oncor, Gaithersburg, Md.) (Kim et al., 1994). Genomic DNA was obtained from vector control or MycER transduced IMR90 fibroblasts. TRAP assays were performed on lysates equivalent to 1000 cells for all samples, with 293T cell lysates serving as a positive control for telomerase activity. PCR internal controls from each experiment were amplified equally. Inactivation of lysate was for 5 minutes at 85° C. prior to the TRAP assay.

In the MycER system, the Myc moiety exists in a latent form bound in a complex with HSP-90 through its ER fusion (Eilers et al., 1989; Littlewood et al., 1995). Upon treatment with 4-hydroxy-tamoxifen (4-OHT), the MycER protein is liberated from HSP-90, resulting in a Myc over-expression phenotype (Eilers et al., 1989; Littlewood et al., 1995). Employing this cell culture system, 4-OHT treatment of MycER-transduced IMR90 cultures resulted in the marked and sustained activation of telomerase to a level at or above that detected in lysates derived from an equivalent number of telomerase-positive 293T tumor cells, as assayed by the sensitive TRAP assay. In contrast, untreated MycER-transduced or 4-OHT-treated pBABE-transduced IMR90 cultures remained telomerase negative. Western blot analysis confirmed abundant MycER protein levels in the MycER-transduced cultures in the presence or absence of 4-OHT.

Notably, enforced expression of oncogenes such as H-Ras, and cellular modulators of the Rb and p53 pathways (E7, cyclin D1, Mdm2, dominant-negative p53) have not been found to be capable of influencing telomerase activity in IMR90 cells (Wang et al., 1998).

c-Myc Enhancement of hTERT Transcription Requires the Presence of a Cis-Acting Promoter Element: the Proximal Myc-Binding E-Box hTERT Reporter Construction: The pGRN150 (E box deleted), pGRN261 (2.5 kbp hTERT reporter) are described above. NIH 3T3 cells were grown in Dulbecco's Modified Eagle Medium (DMEM) (Gibco/BRL) supplemented with 10% fetal bovine serum (FBS), 0.29 mg/mL L-glutamine, 0.03% penicillin and streptomycin, and 25 µg/mL gentamycin sulfate. NIH 3T3 cells were transfected using Lipo-Fectamine™ reagent (Life Sciences) with 100 ng of a promoter reporter, and 200 ng of pCMX-β-Galactosidase which served as an internal control for transfection efficiency. Transfected cells were allowed to recover for 6 hours in complete DMEM and then treated with 1 µM 4-OHT or ethanol for 36 hours prior to analysis of secreted alkaline phosphatase activity using the Great EscAPe™ assay (Clon-Tech). β-galactosidase activity was assayed by incubation of whole cell extracts with 400 µg/ml ONPG in buffer containing 60 mM Na2HPO4, 40 mM NaH2PO4, 10 mM KCl and 1 mM MgSO4 and relative transfection efficiencies determined by reading absorbance at 415 nm.

Expression of endogenous hTERT following exposure to 4-OHT (or solvent alone) was measured at various times in the presence of 1 µM cyclohexamide in IMR90 fibroblasts transduced with MycER. Reverse transcription of RNA derived from each sample followed by PCR and Southern blotting of the amplified products was carried out as described above. Glyceraldehyde-6-phosphate dehydrogenase (GAPDH) was amplified from the same reverse transcription products as an internal semi-quantitative control and visualized by ethidium bromide staining. Low level expression of hTERT mRNA was detected in uninduced samples after very long exposures; however, the level of hTERT mRNA did not change over time in the uninduced samples.

The activity of the hTERT promoter was dramatically enhanced by c-Myc-ER in NIH 3T3 cells. The ability of c-Myc-ER to enhance hTERT promoter activity was dependent upon sequences in the hTERT promoter that included an evolutionarily conserved Myc binding site (E-box).

To determine whether the increased telomerase activity induced by activation of c-Myc-ER was a result of increased transcription of the hTERT gene we initially examined the effect of 4-OHT induction of c-Myc-ER activity upon hTERT promoter sequences placed upstream of the secreted alkaline phosphatase reporter gene. The hTERT promoter contains two putative Myc-binding sites positioned at −242 and −34 relative to the ATG initiation codon.

NIH 3T3 cells engineered to express c-Myc-ER stably were transfected with constructs containing a secreted alkaline phosphatase reporter under the control of a 2.5 kb fragment of the hTERT promoter, a 2.5 kb fragment of the hTERT promoter lacking the proximal E-box, or a promoterless reporter construct. The basal activity of the wild-type hTERT promoter and that of the hTERT promoter lacking the proximal E-box were equivalent and approximately 3 fold higher than the activity of the promoterless reporter. Induction of c-Myc-ER activity with 1 µM 4-OHT enhanced the activity of the 2.5 kb hTERT promoter approximately 10 fold. By contrast, the activity of the promoter lacking the proximal E-box was not significantly affected by induction of c-Myc-ER. Similarly, the promoterless reporter was not affected by induction of c-Myc-ER. Clearly, this shows that transcription of a heterologous encoding region can be regulated by modulating a transcriptional regulatory element such as c-Myc within the promoter region, which in turn is modulated by a ligand for the estrogen receptor.

To further confirm the role of the proximal E-box in regulating the hTERT promoter we tested the effect of changing the E-box from CACGTG to CACTCA. The mutation in the E-box reduced the promoter activity due to 4-OHT stimulation to the equivalent of the E-box deletion and 10-fold below the wild-type promoter. This demonstrates that c-Myc-ER is not able to significantly activate an hTERT promoter with an attenuated E-box at −34 and that the E-box at −242 is not able to significantly mediate c-Myc activation. These results suggest that the ability of c-Myc to stimulate the hTERT promoter is mediated via the −34 E-box.

hTERT is a Direct Target of c-Myc Regulated Transcription

To confirm the ability of c-Myc to stimulate transcription of the hTERT gene directly, we assayed for hTERT gene expression in MycER-transduced cultures of IMR90 cells 0, 1, 3 and 9 hours following the addition of 4-OHT. The cultures were treated with cyclohexamide for 30 minutes prior to addition of 4-OHT to prevent de novo protein synthesis. hTERT expression was undetectable at the zero hour time point for the Myc transduced cultures. Pretreatment of these cells with cyclohexamide alone had no effect on expression of hTERT mRNA. Induction of the c-Myc-ER activity by treatment with 2 M 4-OHT in the presence of 1 cyclohexamide led to a rapid increase in expression of hTERT message.

hTERT expression was detected by 1 hour post-induction, and increased 3 and 9 hours post induction. By contrast, cells treated with solvent alone were not induced to express hTERT. Furthermore, the expression level of GAPDH was similar at all time points in cells treated with 4-OHT or solvent alone. These observations strongly suggest that Myc acts directly upon the hTERT promoter to enhance transcription of the hTERT gene.

Lack of Equivalence of Myc and TERT in Cellular Transformation.

To further explore the functional implications of Myc induction of telomerase activity in primary cells, we examined whether TERT could substitute for c-Myc as an immortalizing agent in the rat embryonic fibroblast (REF) cooperation assay. In this assay, co-transfection of Myc and activated RAS (H-RASG12V) effects the malignant transformation of early passage REFs. This cooperative activity can be quantified by monitoring the number of transformed foci appearing in the monolayer 7 to 10 days post-transfection. In two separate experiments, various combinations of the expression constructs encoding c-Myc, H-RASG12V, TERT, or vector control were introduced into early passage REFs. Strong cooperative activity was observed in the RAS and Myc co-transfections as evidenced by an average of 34 foci per 10 cm plate; while Ras alone generated between 0 and 3 foci per plate; consistent with previous findings that an immortalizing agent and activated RAS are required for efficient transformation of primary rodent cells (Land et al., 1983). By contrast, co-transfection of TERT and RAS did not generate transformed foci counts above that scored for the RAS alone controls. These results indicate that expression of hTERT is insufficient to account for the immortalizing function of Myc in a rat embryonic fibroblast (REF) cooperation assay.

Effect of c-Myc-ER on the activity of the hTERT promoter in NIH3T3 cells was determined by detection of secreted alkaline phosphatase activity. Cells were treated with 4-OHT for 36 hours. Uninduced cells were treated with solvent alone for 36 hours. The detected secreted alkaline phosphatase activity was corrected for transfection efficiency in each case using β-galactosidase.

Example 9

Cloning of Mouse TERT Promoter

The following example details the cloning of the mouse mTERT promoter.

mTERT Construction: A hybridization probe (nucleotides 1586-1970) of the mTERT cDNA (pGRN188) was used to identify a recombinant phage (mTERT1) from a 129SV mouse genomic phage library (Stratagene). An 8 kb HindIII fragment of mTERT1 that hybridized to the 1586-1970 probe was subcloned into pBluescript™ II KS+(Stratagene) to generate clone B2.18. The regions encompassing the initiator and promoter were sequenced.

The mTERT upstream sequence is listed in SEQ. ID NO:2 The sequence can be obtained on GenBank under Accession B2.18 AF121949.

FIG. 3 shows the alignment of homologous portions of the human and mouse promoter sequences. The sequences were aligned using the GAP program from the Wisconsin GCG package, using a value of 48 for gap creation and a value of 3 for gap extension. Using a small portion of the coding region (≈450 bases) was found to improve the initial alignment.

Conservation of Human and Mouse TERT Promoters

To determine whether the ability of c-Myc to enhance telomerase activity was mediated through increased transcription of the hTERT gene, we compared the sequences of the human and mouse TERT promoters. Alignment of the first 300 bases of the human and mouse promoters indicates a number of conserved regions. In particular, the Myc/Max binding site (E-box) located at −34 of the human promoter and at −32 of the mouse promoter, are highly conserved. A second E-box was identified at −242 of the human promoter; however, this site was not conserved in the mouse promoter. These observations raised the possibility that the conserved Myc binding site in particular might play a role in the regulation of hTERT expression by c-Myc

Example 10

Exemplary Oncolytic Virus

Based on the principles illustrated in Example 4, the following experiment was done as a model for an oncolytic virus based on the Ad2 type adenovirus. A construct was made in which the adenovirus E1a replication gene was placed under control of the hTERT promoter, which should activate transcription in telomerase-expressing cancer cells. As a positive control, a similar construct was made in which E1a was placed under control of the CMV promoter, which should activate transcription in any cell.

Reagents were obtained as follows. pBR322, restriction enzymes: NEB, Beverly, Mass. Adenovirus Type 2 (Ad2), tissue culture reagents: Gibco/BRL, Grand Island, N.Y. Profection Mammalian Transfection Systems: Promega, Madison, Wis. Tumor and Normal Cell lines: ATCC, Manassas, Va., except BJ line, which was obtained from J. Smith, U. of Texas Southwestern Medical Center.

Briefly, a pBR322-based plasmid was constructed which contains the Adenovirus Type 2 genome with deletions from 356-548 nt (E1a promoter region) and 27971-30937 nt (E3). A multiple cloning region was inserted at the point of deletion of the E1a promoter, and hTERT promoter (−239 to −36 nt) or CMV promoter (−524 to −9 nt) was subsequently cloned. Numbering of the CMV sequence is in accordance with Akrigg et al., Virus Res 2:107, 1985. Numbering of the Ad2 sequence is in accordance with "DNA Tumor Viruses: Molecular Biology of Tumor Viruses", J. Tooze ed., Cold Spring Harbor Laboratory, N.Y.

These plasmid DNAs were digested with SnaBI to liberate ITRs, then phenol-chloroform extracted, precipitated and transfected into 293A cells for propagation of the virus. Several rounds of plaque purifications were performed using A549 cells, and a final isolate was expanded on these same cells. Viruses were titered by plaque assay on 293A cells, and tested for the presence of 5' WT Ad sequences by PCR. DNA was isolated from viruses by HIRT extraction.

The hTERT promoter construct was designated Adph-TERT-E1dIE3. The CMV promoter construct was designated AdCMV-E1dIE3.

Figure 4:
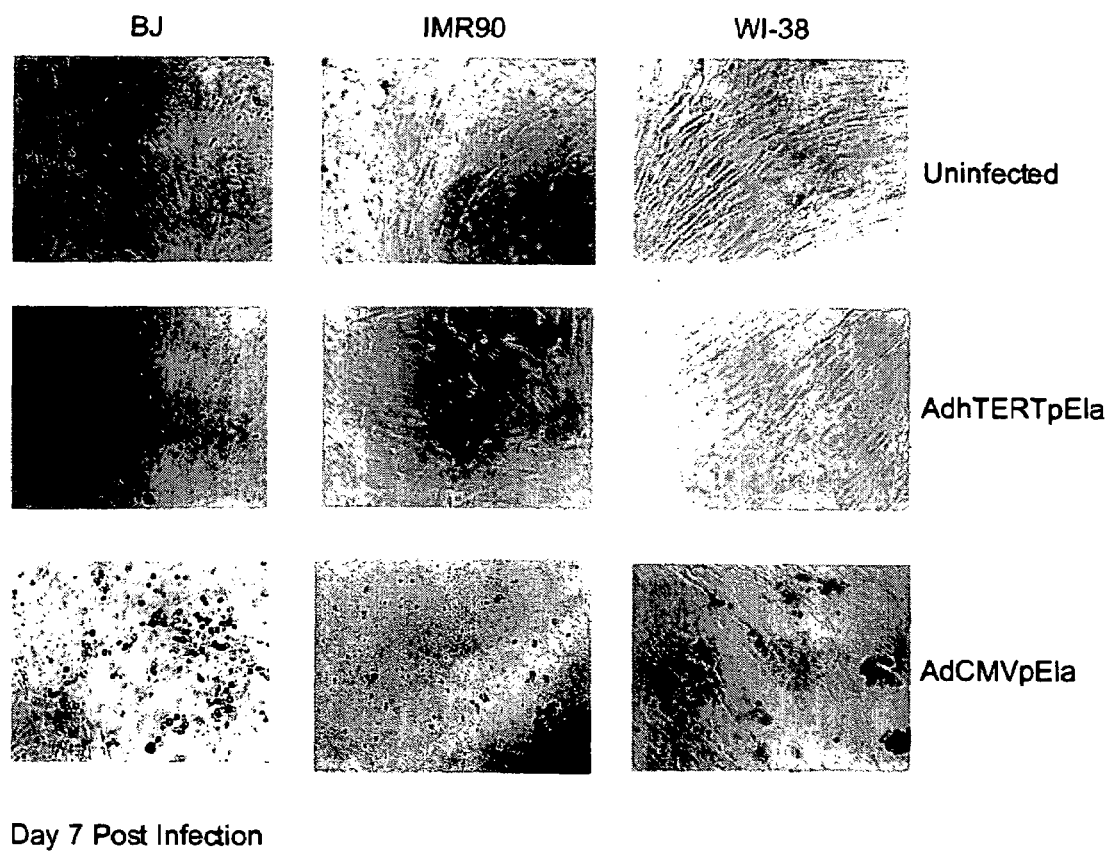
FIG. 4 is a half tone reproduction of cell lines photographed 7 days after infection with oncolytic virus. Top row: uninfected cells (negative control). Middle row: cells infected with oncolytic adenovirus, in which replication gene E1a is operably linked to the hTERT promoter. Bottom row: cells infected with adenovirus in which E1a is operably linked to the CMV promoter (positive control).
Figure 4:
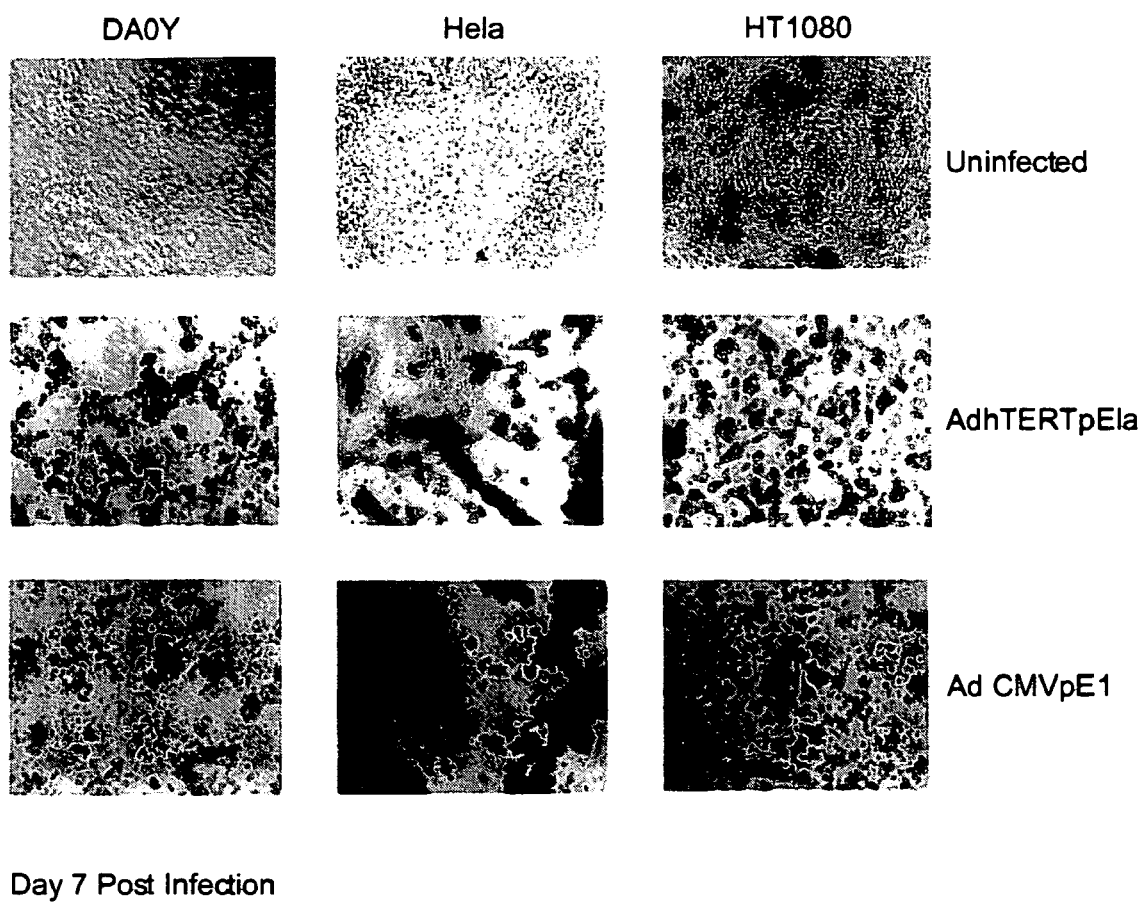

FIG. 4 shows the effect of these viruses on normal and cancer-derived cell lines. Each cell line was plated at 5×10 in a 48-well format and infected at an MOI=20, ≈24 h post plating. The cells were then cultured over a period of 17-48 days, and fed every fourth day. The pictures shown in the Figure were taken 7 days after infection. The top row shows the results of cells that were not virally infected (negative control). The middle row shows the results of cells infected with oncolytic adenovirus, in which replication gene E1a is operably linked to the hTERT promoter. The bottom row shows the results of cells infected with adenovirus in which E1a is operably linked to the CMV promoter (positive control). Results are summarized in Table 2:

TABLE 2

Effect of Oncolytic Virus on Cancerous and Non-cancerous Cells

| Cell Line | Origin | Culture Conditions | | Uninfected cell Lysis | Lysis by Ad-phTERT-E1dIE3 | Lysis by Ad-CMV-E1dIE3 |
|---|---|---|---|---|---|---|
| BJ | foreskin fibroblast | 90% DMEM/M199 + 10% FBS | FIG. 4 (A) | NO | NO | YES |
| IMR | lung fibroblast | 90% DMEM/M199 + 10% FBS | FIG. 4 (A) | NO | NO | YES |

TABLE 2-continued

Effect of Oncolytic Virus on Cancerous and Non-cancerous Cells

| Cell Line | Origin | Culture Conditions | | Uninfected cell Lysis | Lysis by Ad-phTERT-E1dIE3 | Lysis by Ad-CMV-E1dIE3 |
|---|---|---|---|---|---|---|
| WI-38 | lung fibroblast | 90% DMEM/M199 + 10% FBS + 5 μg mL gentamicin | FIG. 4 (A) | NO | NO | YES |
| A549 | lung carcinoma | 90% RPMI + 10% FBS | FIG. 4 (B) | NO | YES | YES |
| AsPC-1 | adenocarcinoma, pancreas | 90% RPMI + 10% FBS | FIG. 4 (B) | NO | YES | YES |
| BxPC-3 | adenocarcinoma, pancreas | 90% EMEM + 10% FBS | FIG. 4 (B) | NO | YES | YES |
| DAOY | medulloblastoma | 90% EMEM + 10% FBS | FIG. 4 (C) | NO | YES | YES |
| HeLa: | cervical carcinoma | 90% EMEM + 10% FBS | FIG. 4 (C) | NO | YES | YES |
| HT1080 | fibrosarcoma | 90% EMEM + 10% FBS | FIG. 4 (C) | NO | YES | YES |

All cell lines tested were efficiently lysed by AdCMV-E1dIE3 by day 17 post-infection. All tumor lines were lysed by AdphTERT-E1dIE3 in a similar, but slightly delayed time-frame, while normal lines showed no signs of cytopathic effect and remained healthy out to 6 weeks post-infection.

In a parallel experiment, each cell line was infected with an adenovirus containing the gene encoding the green fluorescent protein as a visual marker (MOI=100), to determine relative transduction efficiency of these cells by adenovirus vectors. The cell lines exhibited a wide range of transduction efficiencies (~1-2% to 100%). Even cells that are transduced poorly can be efficiently eradicated with the hTERT controlled adenovirus.

Together, the results confirm that a oncolytic virus can be constructed by placing a genetic element essential for replication of the virus under control of an hTERT promoter. Replication and lysis occurs in cancer cells, but not in differentiated non-malignant cells.

FIG. 5 is a map of the oncolytic adenovirus used in the infection experiment shown in FIG. 4. It comprises the Inverted Terminal Repeat (ITR) from the adenovirus (Ad2); followed by the hTERT medium-length promoter (ph-TERT176) operably linked to the adenovirus E1a region; followed by the rest of the adenovirus deleted for the E3 region (ΔE3). Shown underneath are some modified constructs. The middle construct comprises an additional sequence in between the hTERT promoter and the E1a region. The HI sequence is an artificial intron engineered from adenovirus and immunoglobulin intron splice donor and acceptor sequences. It is thought that placing an intron in the hTERT promoter adenovirus replication gene cassette will promote processing and transport of heteronuclear RNA, thereby facilitating formation of the replicated viral particles. The third adenovirus construct is similar, except that the E1a region used is longer at the 5' end by 51 nucleotides. It is thought that this may also promote more efficient conditional replication of the oncolytic virus.

REFERENCES

1. Bello-Fernandez. (1993). Proc Natl Acad Sci USA. 90,7804-8.
2. Bishop (1991). C.S.H. Symp. Quant. Biol. 56, 99-107.
3. Bodnar (1996). Expt. Cell Res. 228, 58-64.
4. Bodnar (1998). Science 279,349-52.
5. Chase (1998) Nature Biotechnol. 16, 444-448.
6. Coffey (1998) Science 282:1332-1334
7. Counter (1992). EMBO J. 11, 1921-1929.
8. Eilers (1989). Nature 340, 66-68.
9. Eilers (1991). EMBO J. 10,133-41.
10. Fujimoto. (1997). Biochem. & Biophys. Res. Comm. 241, 775-781.
11. Galaktionov (1996). Nature 382, 511-7
12. Grandori (1996). EMBO J. 15,4344-57
13. Grandori (1997). TIBS 22, 177-181.
14. Greenberg, (1998) Oncogene 16,1723-30.
15. Harley (1990). Nature 345, 458-460.
16. Harrington. (1997). Genes Dev. 11, 3109-3115.
17. Hastie (1990) Nature 346, 866-868.
18. Hiyama (1995). Nature Med. 1, 249-255.
19. Kilian (1997). Hum. Mol. Genet. 6, 2011-2019.
20. Kim, (1994) Science 266, 2011-2015.
21. Kiyono (1998). Nature 396, 84-88.
22. Klingelhutz (1996) Nature 380, 79-82.
23. Kramm (1997) Hum. Gene Ther.8, 2057-2068.
24. Land (1983) Nature 304, 596-602.
25. Lee (1997) Proc Natl Acad Sci USA 94,12886-91.
26. Marhin (1997) Oncogene 14, 2825-34.
27. Meyerson (1997) Cell 90, 785-795.
28. Nakamura (1997) Science 277, 955-959.
29. Nakayama (1998) Nature Genet. 18, 65-68.
30. Reed (1986) Proc. Natl. Acad. Sci USA 83, 3982-3986.
31. Schreiber-Agus (1995) Cell 80, 777-786.
32. Smith (1998) Science 282,1484-7.
33. Toda (1998) Human Gene Therapy 9, 2177-2185.
34. van Steensel (1997) Nature 385,740-3.
35. Vaziri (1998) Curr. Biol. 8, 279-282.
36. Wagner. (1993) Cell Growth Differ. 4,879-83.
37. Wang. (1998) Genes Dev. 12, 1769-74.
38. Wright. (1995) Trends Cell Biol. 5, 293-297.
39. Xu (1997) Oncogene 15, 2589-2596.

BIOLOGICAL DEPOSIT

The lambda clone designated λGφ5 (from which SEQ. ID NO:1 was determined) was deposited under terms of the Budapest Treaty with the American Type Culture Collection (ATCC), 10801 University Blvd., Manassas, Va. 20110-2209 U.S.A., on Aug. 14, 1997, under Accession No. 98505.

SEQUENCE LISTING

SEQ. ID NO:1 (hTERT gene sequence in GenBank Accession AF121948)
SEQ. ID NO:2 (mTERT sequence, GenBank Accession AF121949)

The invention claimed is:

1. A method for identifying a compound that modulates the activity of a telomerase reverse transcriptase promoter, comprising:
   a) combining a compound with a polynucleotide comprising the sequence from position −239 to position +1 relative to the translation initiation site of SEQ ID NO: 1 (nucleotides 13306-13545 of SEQ ID NO: 1); and
   b) identifying a compound that binds said polynucleotide and modulates the activity of said promoter.

2. The method of claim 1, wherein the compound is a protein.

3. The method of claim 1, wherein the compound identified increases the activity of said promoter.

4. The method of claim 1, wherein the compound identified decreases the activity of said promoter.

* * * * *

UNITED STATES PATENT AND TRADEMARK OFFICE
CERTIFICATE OF CORRECTION

| | | |
|---|---|---|
| PATENT NO. | : 7,378,244 B2 | Page 1 of 1 |
| APPLICATION NO. | : 11/411604 | |
| DATED | : May 27, 2008 | |
| INVENTOR(S) | : Gregg B. Morin et al. | |

It is certified that error appears in the above-identified patent and that said Letters Patent is hereby corrected as shown below:

Item [54] and col. 1, lines 1-3,
In the title, "PROMOTERS" is misspelled and the title should read, --TELOMERASE PROMOTER SEQUENCES FOR SCREENING TELOMERASE MODULATORS--

Signed and Sealed this

Fifth Day of August, 2008

JON W. DUDAS
*Director of the United States Patent and Trademark Office*